(12) United States Patent
Fischer et al.

(10) Patent No.: US 11,648,001 B2
(45) Date of Patent: May 16, 2023

(54) MECHANICAL MESH FIXATION DEVICE AND CURVILINEAR TACK SYSTEM

(71) Applicant: THE TRUSTEES OF THE UNIVERSITY OF PENNSYLVANIA, Philadelphia, PA (US)

(72) Inventors: John P. Fischer, Philadelphia, PA (US); Jonathan Sanchez, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 324 days.

(21) Appl. No.: 16/119,276

(22) Filed: Aug. 31, 2018

(65) Prior Publication Data

US 2019/0059871 A1  Feb. 28, 2019

Related U.S. Application Data

(60) Provisional application No. 62/552,813, filed on Aug. 31, 2017.

(51) Int. Cl.
 *A61B 17/068* (2006.01)
 *A61F 2/00* (2006.01)
 (Continued)

(52) U.S. Cl.
 CPC ........ *A61B 17/04* (2013.01); *A61B 17/00491* (2013.01); *A61B 17/064* (2013.01);
 (Continued)

(58) Field of Classification Search
 CPC ........... A61B 2017/0647; A61F 2/0063; A61F 2002/0072
 See application file for complete search history.

(56) References Cited

U.S. PATENT DOCUMENTS 5,544,664 A * 8/1996 Benderev ........... A61B 17/0401
128/898
5,830,221 A * 11/1998 Stein .................... A61B 17/068
606/157

(Continued)

FOREIGN PATENT DOCUMENTS

EP         1 595 504 A1    11/2005
WO    WO 2007/059199 A2    5/2007
WO    WO 2010/099327 A1    9/2010

OTHER PUBLICATIONS

U.S. Appl. No. 15/076,204 (US 2017/0319319), filed Mar. 12, 2016 (Nov. 9, 2017).

(Continued)

*Primary Examiner* — Sarah A Simpson
*Assistant Examiner* — Lindsey Bachman
(74) *Attorney, Agent, or Firm* — Baker Botts L.L.P.

(57) ABSTRACT

Devices and methods for affixing reinforcing material to a fascial incision in an abdominal wall to reinforce and augment closures thereof. The device includes first and second arms, each having a proximal end and a distal end extending away from a housing with a length therebetween. The distal end of the first arm is spaced from the distal end of the second arm such that the first and second arms are engageable with reinforcing material on opposing sides of a fascial incision. One or more fixation elements are deployable from the distal end of at least one of the first and second arms to affix the reinforcing material on opposing sides of the fascial incision.

17 Claims, 84 Drawing Sheets

(51) Int. Cl.
  *A61B 17/04*   (2006.01)
  *A61B 50/33*   (2016.01)
  *A61B 17/00*   (2006.01)
  *A61B 50/20*   (2016.01)
  *A61B 17/064*  (2006.01)
  *A61B 50/22*   (2016.01)
  *A61B 50/30*   (2016.01)

(52) U.S. Cl.
  CPC ............ *A61B 17/068* (2013.01); *A61B 50/20* (2016.02); *A61B 50/22* (2016.02); *A61B 50/33* (2016.02); *A61F 2/0063* (2013.01); *A61B 2017/00473* (2013.01); *A61B 2017/0409* (2013.01); *A61B 2017/0412* (2013.01); *A61B 2017/0495* (2013.01); *A61B 2017/0647* (2013.01); *A61B 2050/3008* (2016.02); *A61F 2002/0072* (2013.01)

(56) References Cited

U.S. PATENT DOCUMENTS

| | | | |
|---|---|---|---|
| 6,334,446 B1* | 1/2002 | Beyar | A61B 17/0401 128/898 |
| 6,387,041 B1* | 5/2002 | Harari | A61B 17/0401 600/30 |
| 2004/0176785 A1 | 9/2004 | Hermann et al. | |
| 2005/0049638 A1* | 3/2005 | Mandelbaum | A61B 17/08 606/215 |
| 2007/0038220 A1* | 2/2007 | Shipp | A61B 17/064 606/326 |
| 2007/0185506 A1* | 8/2007 | Jackson | A61F 2/0063 606/151 |
| 2008/0167520 A1* | 7/2008 | Benderev | A61B 17/0401 600/37 |
| 2008/0188874 A1* | 8/2008 | Henderson | A61B 17/00234 606/151 |
| 2009/0204130 A1 | 8/2009 | Kantsevoy et al. | |
| 2010/0312357 A1 | 12/2010 | Levin et al. | |
| 2011/0040311 A1 | 2/2011 | Levin et al. | |
| 2011/0054500 A1 | 3/2011 | Ofek et al. | |
| 2012/0149976 A1* | 6/2012 | Wirbisky | A61F 2/0036 600/37 |
| 2012/0184805 A1* | 7/2012 | Pulliam | A61B 17/0625 600/37 |
| 2012/0209401 A1 | 8/2012 | Euteneuer et al. | |
| 2013/0018395 A1 | 1/2013 | Friedlander et al. | |
| 2016/0120631 A1* | 5/2016 | Murphy | A61F 2/0063 606/151 |
| 2017/0172551 A1* | 6/2017 | Rao | A61B 17/0057 |

OTHER PUBLICATIONS

U.S. Appl. No. 16/151,926, filed Oct. 4, 2018.
U.S. Appl. No. 15/076,204, Oct. 25, 2018 Issue Fee Payment.
U.S. Appl. No. 15/076,204, Sep. 24, 2018 Notice of Allowance.
U.S. Appl. No. 15/076,204, Aug. 2, 2018 Response to Non-Final Office Action.
U.S. Appl. No. 15/076,204, Jul. 20, 2018 Applicant Initiated Interview Summary.
U.S. Appl. No. 15/076,204, May 3, 2018 Non-Final Office Action.
U.S. Appl. No. 15/076,204, Apr. 11, 2018 Applicant Initiated Interview Summary.
U.S. Appl. No. 15/076,204, Apr. 10, 2018 Amendment and Request for Continued Examination (RCE).
U.S. Appl. No. 15/076,204, Feb. 23, 2018 Final Office Action.
U.S. Appl. No. 15/076,204, Dec. 18, 2017 Response to Non-Final Office Action.
U.S. Appl. No. 15/076,204, Nov. 24, 2017 Non-Final Office Action.
U.S. Appl. No. 15/076,204, Nov. 6, 2017 Response to Restriction Requirement.
U.S. Appl. No. 15/076,204, Sep. 29, 2017 Restriction Requirement.
International Search Report and Written Opinion dated Jul. 26, 2016 in International Application No. PCT/US2016/020685.
Supplementary Partial European Search Report dated Oct. 18, 2018 in EP Application No. 16759493.

* cited by examiner

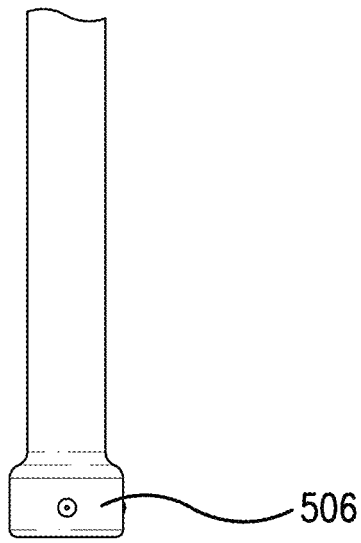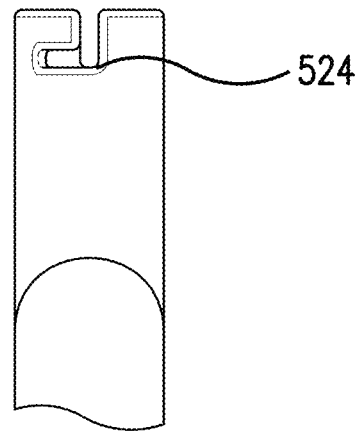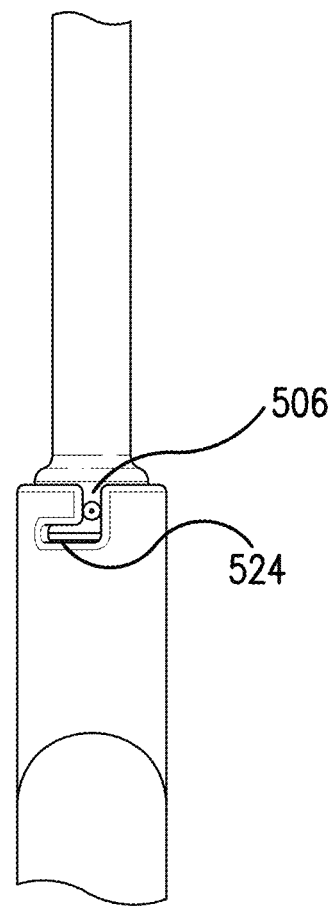
FIG. 5I  FIG. 5J

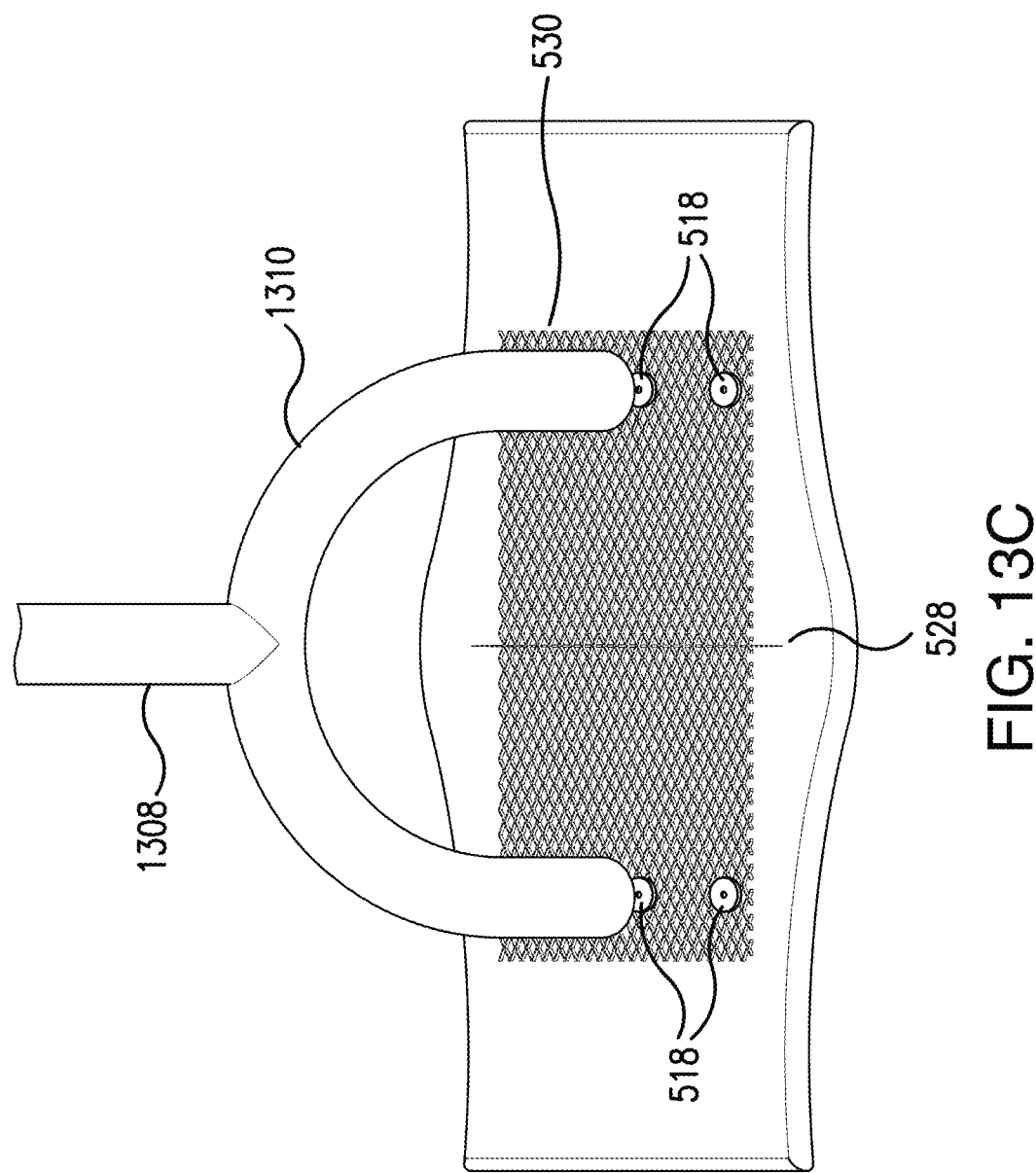

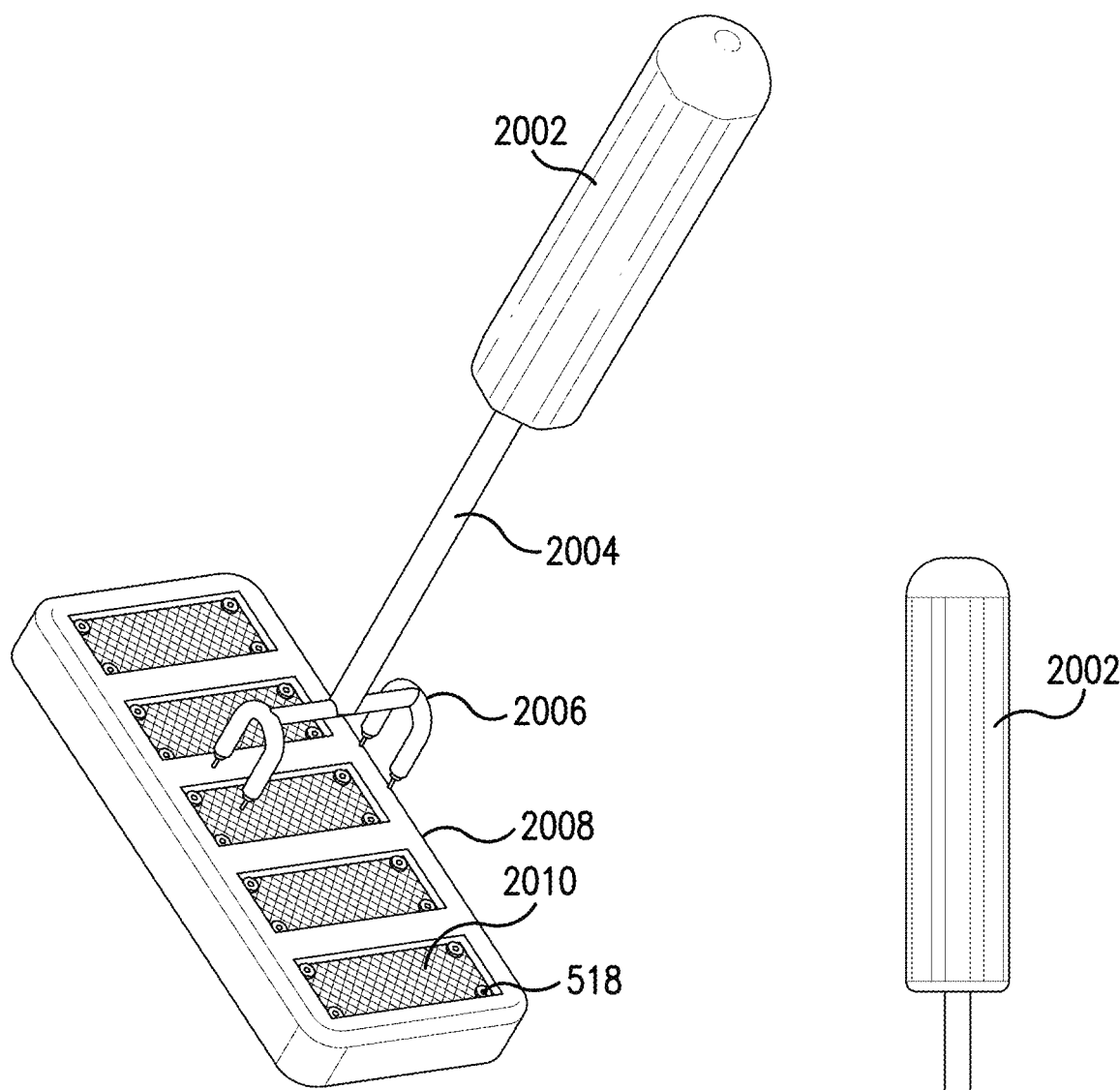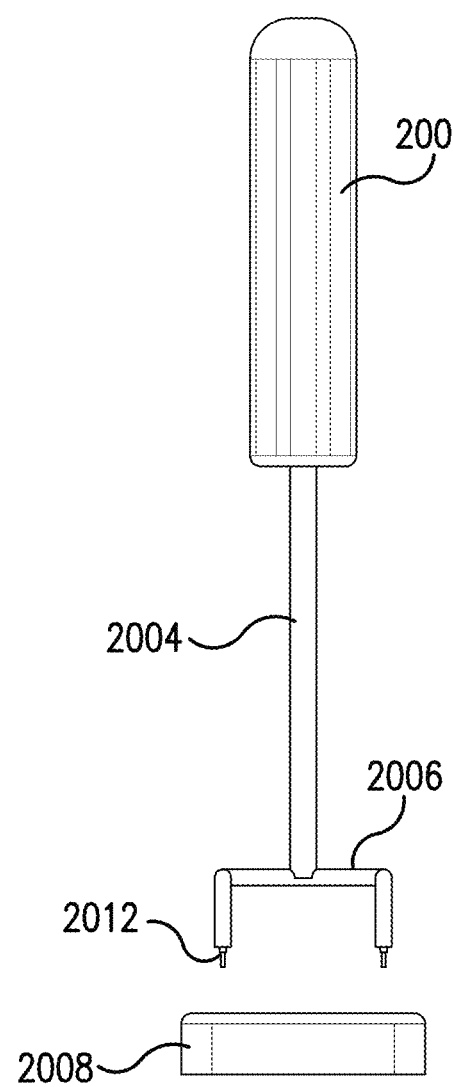
FIG. 20A
FIG. 20B

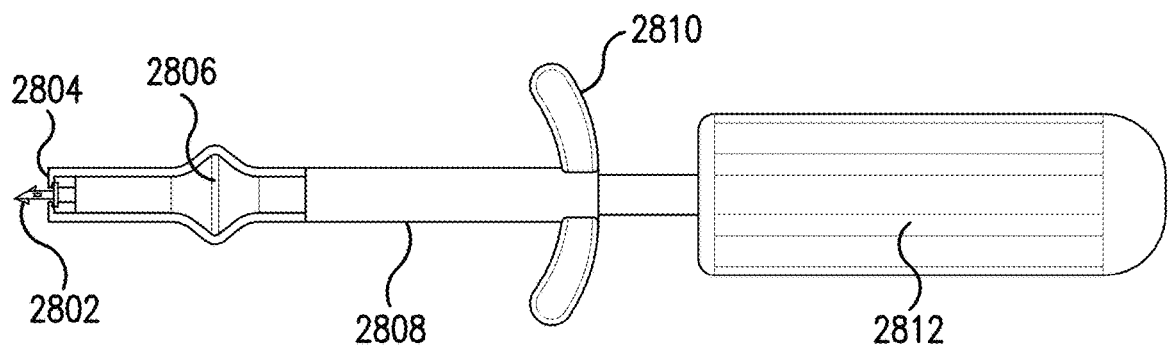
FIG. 28A
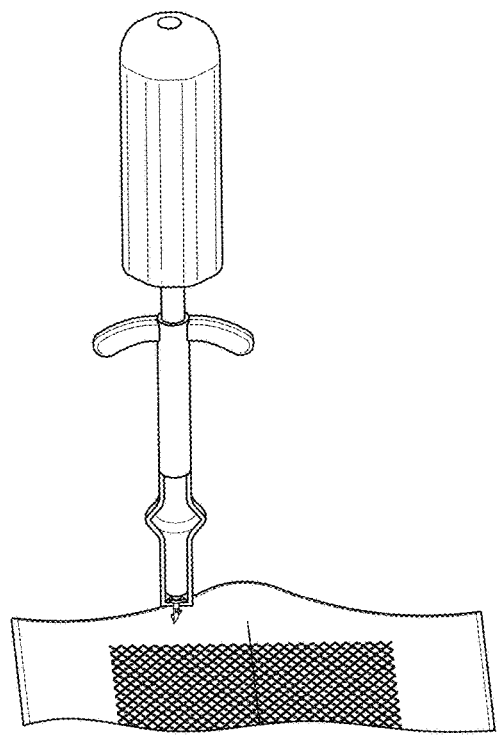
FIG. 28B
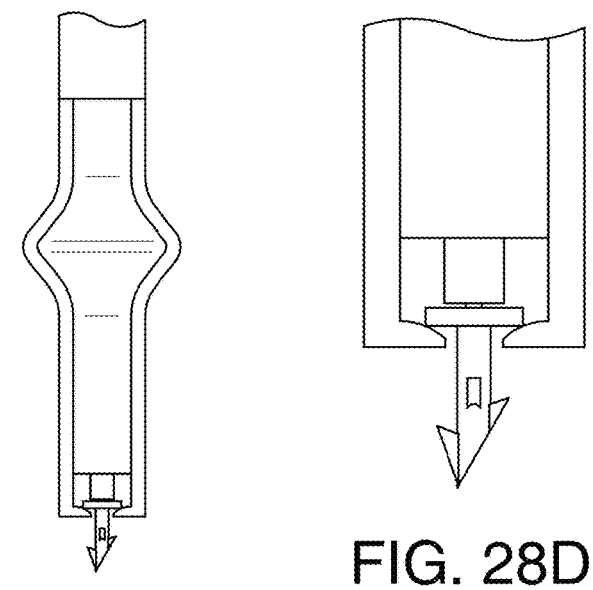
FIG. 28C
FIG. 28D

MECHANICAL MESH FIXATION DEVICE AND CURVILINEAR TACK SYSTEM

CROSS-REFERENCE TO RELATED APPLICATIONS

This application claims priority to U.S. Provisional Application No. 62/552,813, filed Aug. 31, 2017, the content of which is incorporated by reference herein in its entirety.

BACKGROUND

Incisional hernia (IH) is a protrusion of intra-abdominal contents, often intestines, through the abdominal wall, which can be the result of a failed or disrupted fascial closure after surgical incision through the abdominal fascia. The incidence of hernia can be approximately 13% and can be as high as 70% following incisions to the abdominal wall in certain high risk patient populations, and the cost burden for hernia is significant. There are more than 150,000 incisional hernias per year, resulting in costs greater than with more than $7 billion. Further, hernias can be debilitating for patients and associated with a significant decrease in quality of life.

One strategy to prevent IH is to use prophylactic mesh onlay augmentation (PMA) at the index abdominal surgery procedure to reinforce the fascia of before herniation actually occurs. PMA can be implemented to reduce risk and morbidity, and contain cost in high risk patients undergoing abdominal fascial incisions. However, a simple, reliable, and precise mechanism and system to provide PMA is needed. Current challenges of widespread PMA adoption include the added operative, technical challenges related to mesh anchoring and fixation, variability in technique, and uncertain biomechanical benefit and mesh tensioning. Although suturing or fastening the mesh by hand can be effective, this can add operative time and may be subject to user technical ability. Person-to-person variability, added operative time, and biomechanical benefit are thus issues affecting adoption of this technique.

Traditionally, IH is treated after it occurs and is typically reinforced with a mesh to reduce subsequent recurrence. Surgical techniques traditionally affix a surgical mesh using surgical tacks. Traditionally, surgeons position the mesh onto the fascia and affix the mesh to the fascia separately, often using a positioning device and a fixation device. Traditional mesh positioning device and traditional mesh fixation device are two distinct tools that the surgeon must use in order to complete the procedure. Additionally, traditional mesh fixation device deploys single tacks on an individual basis, resulting in a time-consuming process. Traditional mesh fixation devices also deploys straight tack, which provide no lateral tension in the mesh and can often penetrate and injure organs beneath the fascia. Thus a device is needed to rapidly and securely affix surgical reinforcing materials during onlay reinforcement of fascial closures for both the prevention and treatment of incisional hernia.

SUMMARY

The disclosed subject matter provides devices and methods for securely affixing surgical reinforcing materials during onlay reinforcement of fascial closures.

According to one aspect of the disclosed subject matter, a method for affixing a reinforcing material to a fascial incision in an abdominal wall to reinforce and augment closures thereof is provided. The method includes positioning a reinforcing material over the fascial incision and engaging the reinforcing material with an applicator having first and second arms. Each arm includes a proximal end proximate a handle and a distal end that engages the reinforcing material. The distal end of the first arm is spaced from the distal end of the second arm such that the applicator engages with the reinforcing material on opposing sides of the fascial incision. The reinforcing material is affixed to the fascia with tacks by applying force to the tacks with the distal ends of the first and second arms such that the tacks penetrate the fascia on opposing sides of the fascial incision.

The method can include applying lateral tension to the reinforcing material by increasing a distance between opposing sides of the reinforcing material from a first distance to a second distance. In certain embodiments, the lateral tension can be applied by increasing a distance between the distal end of the first arm and the distal end of the second arm from a first distance to a second distance after engaging the reinforcing material with the applicator. In certain embodiments, the applicator can include a spreading mechanism that can control the distance between the distal ends of the first and second arms.

In accordance with another aspect of the disclosed subject matter, a device for affixing a reinforcing material to a fascial incision in an abdominal wall to reinforce and augment closures thereof is provided. The device includes first and second arms, each having a proximal end and a distal end extending away from a housing with a length therebetween. The distal end of the first arm is spaced from the distal end of the second arm such that the first and second arms are engageable with a reinforcing material on opposing sides of a fascial incision. The device further includes one or more fixation elements deployable from the distal end of at least one of the first and second arms to affix the reinforcing material on opposing sides of the fascial incision.

In certain embodiments, the one or more fixation elements can include a plurality of tacks configured to penetrate reinforcing material and fascia to affix the reinforcing material. In certain embodiments, the first and second arms can engage with the reinforcing material on opposing sides of a fascial incision simultaneously. In certain embodiments, the device can include a spreading mechanism mounted to the first arm and at least one of the second arm or the housing. The spreading mechanism can adjust a distance between the distal ends of the first and second arms.

In accordance with another aspect of the disclosed subject matter, a system for affixing reinforcing material to a fascial incision in an abdominal wall to reinforce and augment closures thereof is provided.

BRIEF DESCRIPTION OF THE DRAWINGS

Further features, the nature, and various advantages of the disclosed subject matter will be more apparent from the following detailed description and the accompanying drawings in which:

FIGS. 13A-13C illustrate different views of an exemplary tacker gun with tacks pre-loaded in the barrel of the tacker gun in accordance with an exemplary embodiment of the disclosed subject matter.

FIGS. 20A-20H illustrate different views of a mesh applicator in accordance with an exemplary embodiment of the disclosed subject matter.

FIGS. 28A-D illustrate diagrams of different views of a manual tacker with a tack retainer in accordance with an exemplary embodiment of the disclosed subject matter.

Figure 1A:
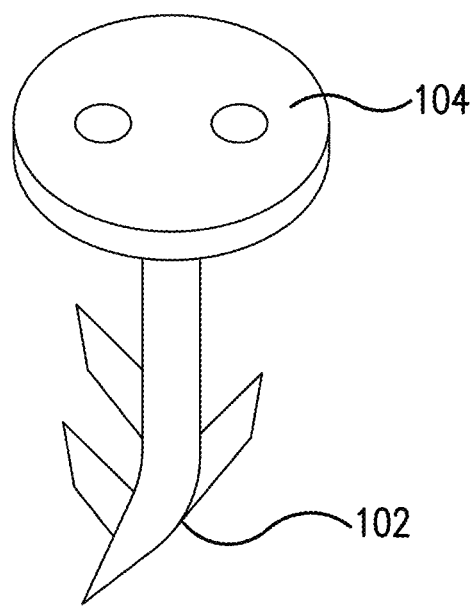
FIGS. 1A and 1B illustrate diagrams of a curvilinear tack with a mating interface in accordance with an exemplary embodiment of the disclosed subject matter.

Throughout the drawings, the same reference numerals and characters, unless otherwise stated, are used to denote like features, elements, components or portions of the illustrated embodiments. Moreover, while the disclosed subject matter will now be described in detail with reference to the figures, it is done so in connection with the illustrative embodiments.

DETAILED DESCRIPTION

The disclosed subject matter relates generally to methods and systems used to perform tissue reinforcement using mesh on-lay fixation to the abdominal wall fascia. In particular, the disclosed subject matter provides a mechanical mesh fixation device that can rapidly and securely fix surgical mesh using affixation elements, such as surgical tacks and adhesive materials.

In accordance with some embodiments, the disclosed subject matter provides a single point and a multi-point mesh affixation device. The disclosed device can include a handle, tack engagement adapters, and tacks. The disclosed tacks can be linear or curvilinear and can be used to affix mesh or other reinforcing materials. The disclosed tacks can be contained in a tray and can be engaged individually and/or can be multiple tacks can be engaged simultaneously at a time. In some embodiments, the disclosed tacks can be contained in the shaft of the affixation device and can be reloaded automatically. In some embodiments, the tacks can be contained in a cartridge and loaded as needed. The disclosed adapter can include springs to allow for tack affixation on uneven surfaces and/or a spreading mechanism to allow the tacks to be moved apart from each other. The disclosed device can also include a tensiometer feature that allows users to control and/or adjust the tension in the mesh, hereinafter also referred to as pre-tensioning the mesh.

In accordance with some embodiments, the disclosed affixation device can include a mesh positioning component. The mesh positioning component can allow the user to grasp onto the mesh, position it, and affix the mesh with a single device. The mesh positioning component can provide the user with improved control over the placement of the mesh and the tacks than traditional mesh positioning devices.

In accordance with some embodiments, the disclosed affixation device can include two U-shaped adapters and tacks that can be attached to a mesh strip. The disclosed U-shaped adapter splits the adapter so as to engage multiple (e.g., two) tacks simultaneously at once, as opposed to traditional devices that can only engage one tack at a time. The pair of U-shaped adapters can engage multiple (e.g., four) tacks simultaneously by inserting the pins on the adapters into the tacks. The disclosed tacks can be attached to a mesh strip such that the mesh strip and the tacks can be applied simultaneously to the fascia. The disclosed mesh strip can be held and/or stored in a mesh tray affixed to the tacks and can be pre-tensioned inside of the tray in order to prevent the surgeon from tensioning the mesh during the procedure.

In accordance with some embodiments, the disclosed subject matter provides a tacker gun device. The disclosed tacker gun device can include a trigger, a barrel, a U-shaped adapter, and tacks. In some embodiments, the disclosed tacks can be housed in the barrel of the tacker gun. In some embodiments, the disclosed tacks can be housed in the U-shaped adapter. In some embodiments, the disclosed U-shaped adapter can be detachable and can be detached from the rest of the tacker gun. The disclosed U-shaped adapter can include a spreading mechanism to allow the tacks to be moved apart from each other manually by applying pressure onto the tacker gun and/or by using a dial or other mechanisms as discussed further herein. Turning the dial can change the distance between the tacker gun's arms, which can consequently change the tension in the mesh. Such mesh tensioning can also be caused by a turnbuckle, as described below in connection with a manual tacker tensiometer by which the user can adjust the pressure to be applied. In some embodiments, the disclosed affixation device can also include a double barrel design in lieu of a single barrel and a U-shaped adapter.

In accordance with some embodiments, the disclosed subject matter provides a mesh applicator. The disclosed mesh applicator device can include a handle, application wheel, and a surgical mesh. The disclosed mesh application can include an application wheel that can be rolled to release the self-adhesive mesh attached to the wheel. The application wheel can house the self-adhesive mesh in order to prevent the mesh from adhering onto any unwanted surface during the application process and to adhere only to the surface of the fascia as intended.

Description will now be made to various embodiments of this aspect of the disclosed subject matter for purpose of illustration and not limitation. Although the embodiments described herein are described primarily with reference to abdominal fascial augmentation for hernia repair and/or hernia prevention through fascial reinforcement, one of skill in the art would appreciate that the subject matter disclosed herein can also be applied to a variety of other procedures. For example, in addition to being used to treat and augment hernia fascia closures, the disclosed subject matter can be utilized for any surgery that requires for mesh reinforcement.

Figure 1B:
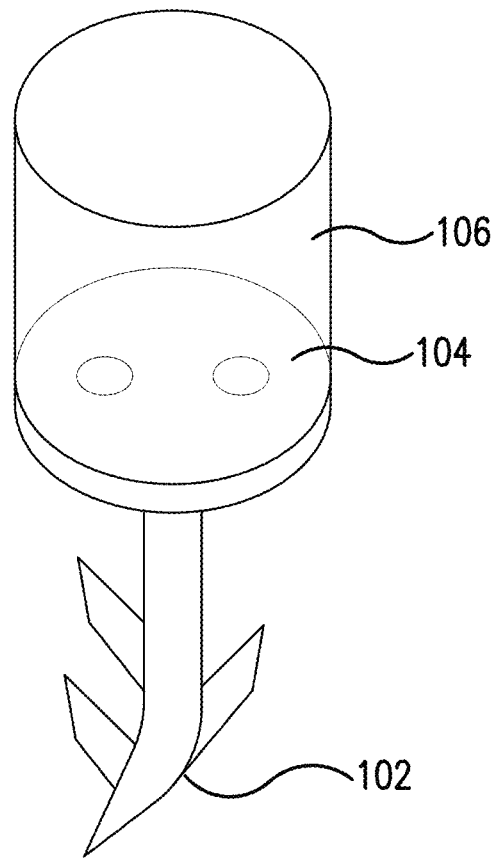

FIGS. 1A and 1B illustrate an exemplary curvilinear tack with a mating interface. The example embodiment depicted by FIG. 1A illustrates a curvilinear tack 102 having an outward curve and a mating interface 104. The mating interface 104 can include at least one hole that can be used to attach the tack to a mesh fixation device. FIG. 1B depicts an exemplary curvilinear tack 102 housed in a tray. The tack 102 can include an outward curve and a mating interface 104. The tray in which the tack is housed can include chamfered holes 106 to align a mating piece of the tack to the mating interface 104. The chamfered holes 106 can assist the mating piece in aligning with and/or connecting to the mating interface.

Figure 1C:
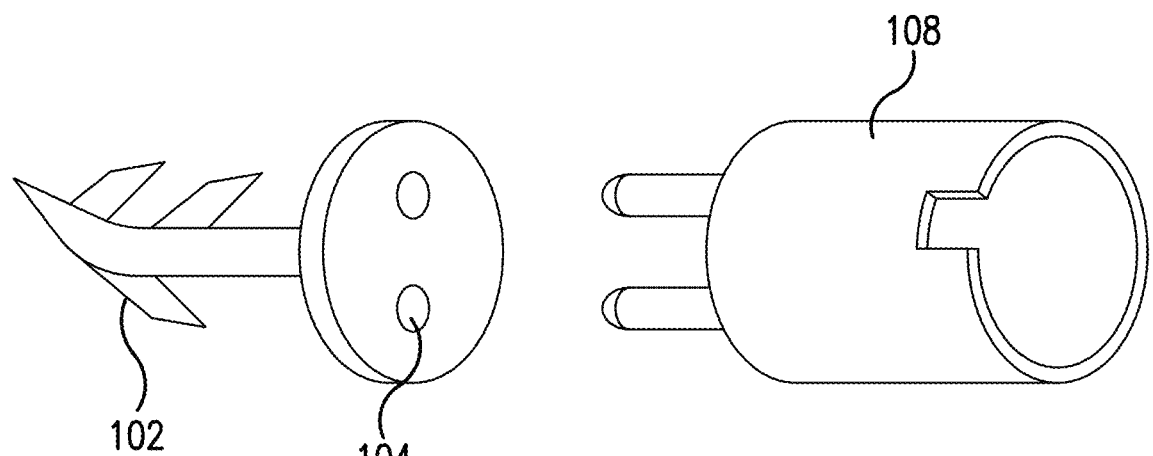
FIG. 1C illustrates a diagram of a curvilinear tack with a mating interface and a mating piece in accordance with an exemplary embodiment of the disclosed subject matter.

FIG. 1C illustrates an exemplary curvilinear tack 102 and a mating piece 108. In particular, FIG. 1C depicts an exemplary mating of the curvilinear tack 102 to a mesh affixation device. According to the exemplary embodiment depicted in FIG. 1C, the mating piece 108 can engage the mating interface 104 by inserting at least one pin into the at least one hole in the mating interface 104. The engagement of the mating piece 108 and the mating interface 104 can connect the tack to the mesh fixation device. In some other embodiments, a telescoping head and/or lip can grab onto the head of the tack and then can be retracted once the tack is affixed into the fascia in place of the mating piece 108 engaging the mating interface 104 using a pin.

Figure 1D:
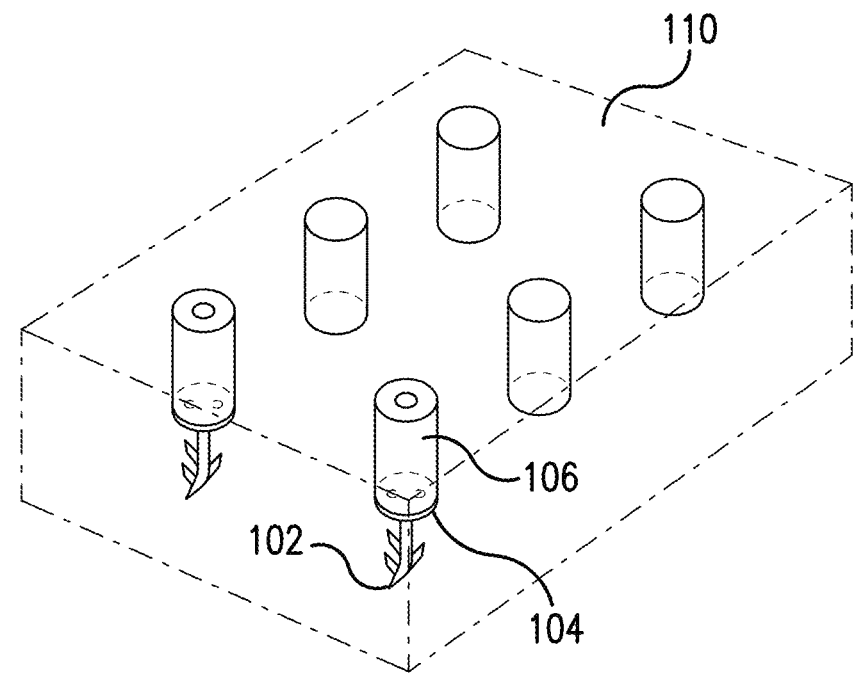
FIG. 1D illustrates a diagram of a tray housing multiple curvilinear tacks with mating interfaces in accordance with an exemplary embodiment of the disclosed subject matter.

FIG. 1D illustrates an exemplary curvilinear tack housed in a tray. As illustrated by FIG. 1D, the tray 110 can contain multiple (e.g., six) tacks stored for an affixation device to pick up and/or engage with. The mating interface 104 of the curvilinear tack 102 can face upward to be configured to engage with the mating piece. The tacks can be contained in individual chamfered holes 106 that can provide the mating interface 104 with the ability to be aligned with a mating piece.

Figure 2:
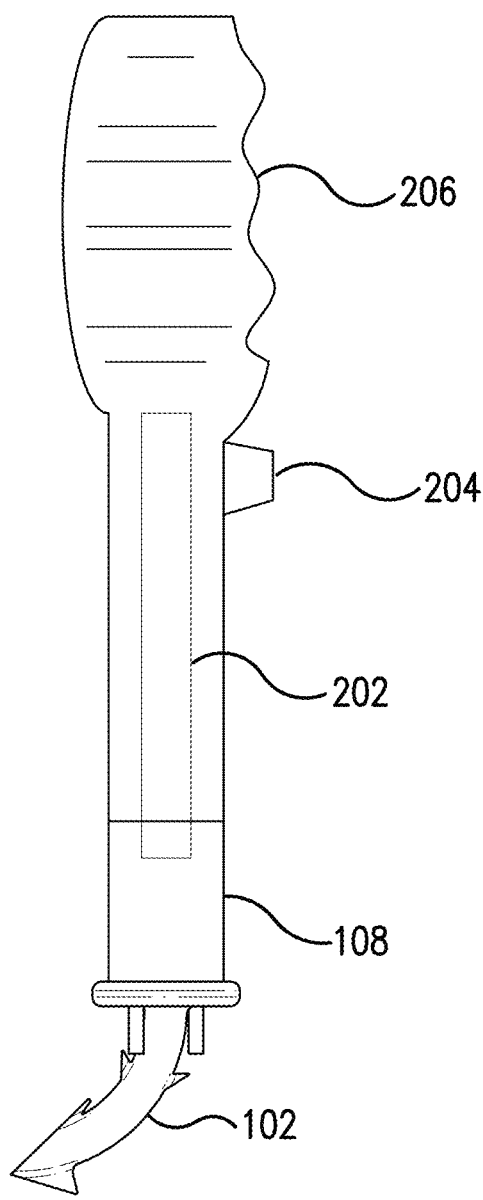
FIG. 2 illustrates a diagram of a mesh fixation device in accordance with an exemplary embodiment of the disclosed subject matter.

FIG. 2 illustrates an exemplary mesh fixation device. The exemplary embodiment depicted by FIG. 2 illustrates a curvilinear tack 102, a mating piece 108, a release mechanism 202 for the mating piece, a release button 204, and a handle 206. The mating piece 108 can engage the curvilinear tack 102. The release mechanism 202 can employ a spring to release and deploy the tacks 102. The release button 204 can be depressed to activate the release mechanism 202. The fixation component system, including the tack 102 and the mating piece 108, can be disposable. The release mechanism 202, release button 204, and handle 206 can be re-used with multiple tacks.

Figure 3:
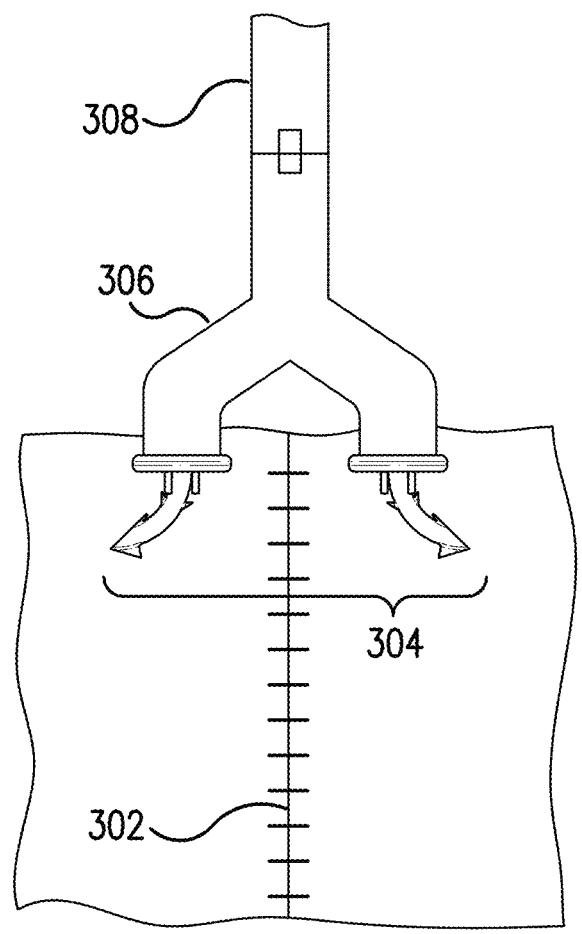
FIG. 3 illustrates a diagram of a Y-shaped adapter for a mesh fixation device in accordance with an exemplary embodiment of the disclosed subject matter.

FIG. 3 illustrates an exemplary Y-shaped adapter for a mesh fixation device. The exemplary embodiment depicted in FIG. 3 illustrates a mesh fixation device being applied to a surgical mesh placed on the fascial incision. The surgical mesh can cover the suture 302 applied to the fascial incision. The device 308 can employ a Y-shaped adapter 306 to deploy fixation elements to affix the mesh on opposing sides of the fascial incision. As embodied herein, the fixation elements can include two curvilinear tacks 304 deployed simultaneously such that each end of the Y-shaped adapter 306 can affix one curvilinear tack 304 to the fascia and/or the surgical mesh. The affixation of two tacks 304 can allow the surgical mesh to be fixed to the fascia.

Figure 4:
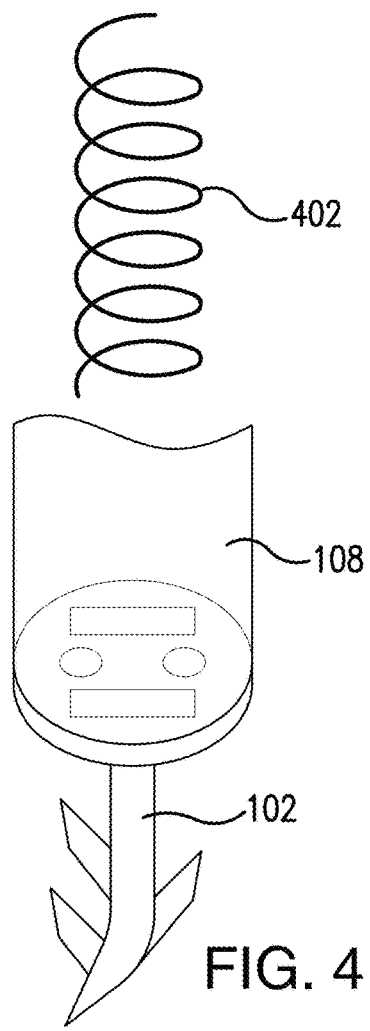
FIG. 4 illustrates a diagram of a spring-mediated release feature for a mesh fixation device in accordance with an exemplary embodiment of the disclosed subject matter.

FIG. 4 illustrates a spring-mediated release feature for a mesh fixation device. The spring 402 can be depressed to activate the release feature. The activated release feature can release the curvilinear tack 102 from the mating piece 108. The release of the curvilinear tack 102 can allow the tack 102 to affix the surgical mesh to the fascia. In some embodiments, the tack can be manually affixed by pushing the applicator into the fascia. The release button, when pressed, can release the tack.

Figure 5A:
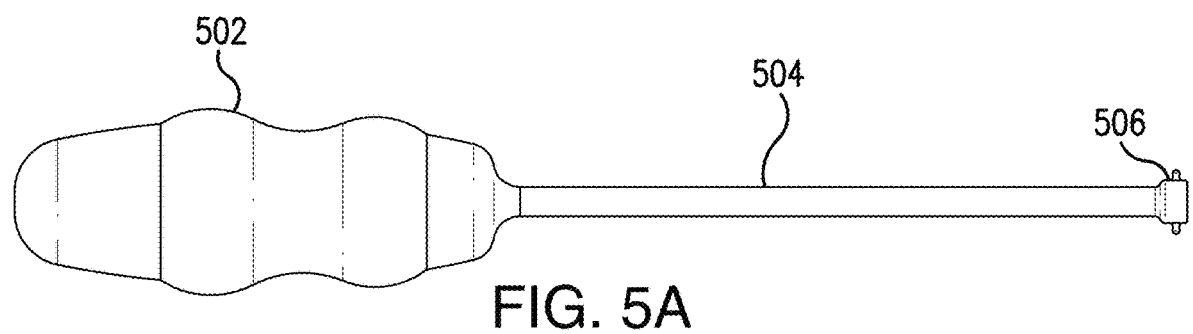
FIGS. 5A-5Z illustrate different views of an exemplary mesh fixation device that affixes a surgical mesh to the fascial manually, in accordance with an exemplary embodiment of the disclosed subject matter.

FIGS. 5A-5F illustrate the design components of an exemplary mesh fixation device. The exemplary embodiment depicted by FIG. 5A illustrates a manual tacker handle having a handle 502, a shaft 504, and a locking mechanism 506. The handle 502 can be used to hold the mesh fixation device. The shaft 504 can connect the handle 502 and the locking mechanism 506. The locking mechanism 506 can be used with a twist-lock mechanism to attach an adapter to the handle 502.

Figure 5B:
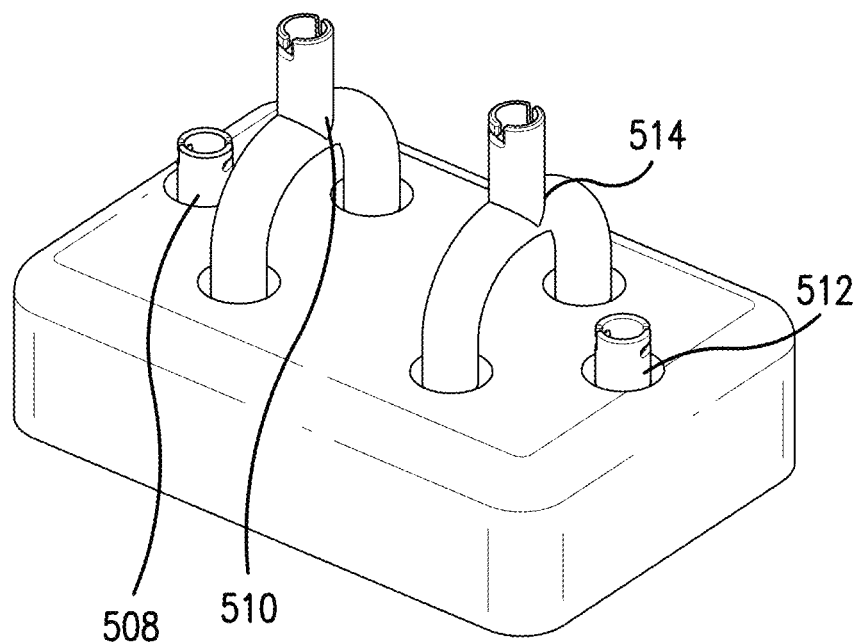

The exemplary embodiment depicted by FIG. 5B illustrates tack engagement adapters 510 and 514. The tack engagement adapters can be contained in a tray. The tray can store and/or hold a single straight tack adapter 508, a dual straight tack adapter 510, a single curvilinear tack adapter 512, and a dual curvilinear tack adapter 514. FIGS. 5E and 5F display perspective views of these various tack engagement adapters. The adapters can use a twist-lock mechanism 524 to attach to the handle of the mesh affixation device. The single tack adapters 508 and 512 can mate with a single tack. The dual tack adapters 510 and 514 can mate with two tacks simultaneously. The straight tack adapters 508 and 510 can include pins 522 that can engage with a tack having a mating interface with a single hole. The curvilinear tack adapters 512 and 514 can include pins 526 that can engage with a tack having a mating interface with two holes.

Figure 5C:
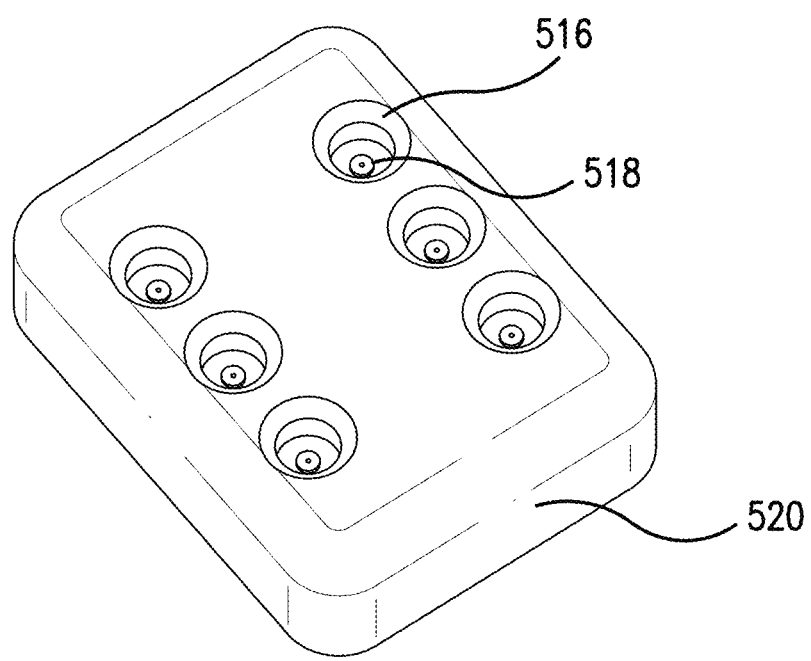

FIG. 5C depicts an exemplary tack tray 520 for storing and/or holding tacks 518 that can be engaged by a mesh fixation device. The tray 520 can include multiple chamfered holes 516 that can help align the mating piece with the mating interface of each tack stored within each chamfered hole 516.

Figure 5D:
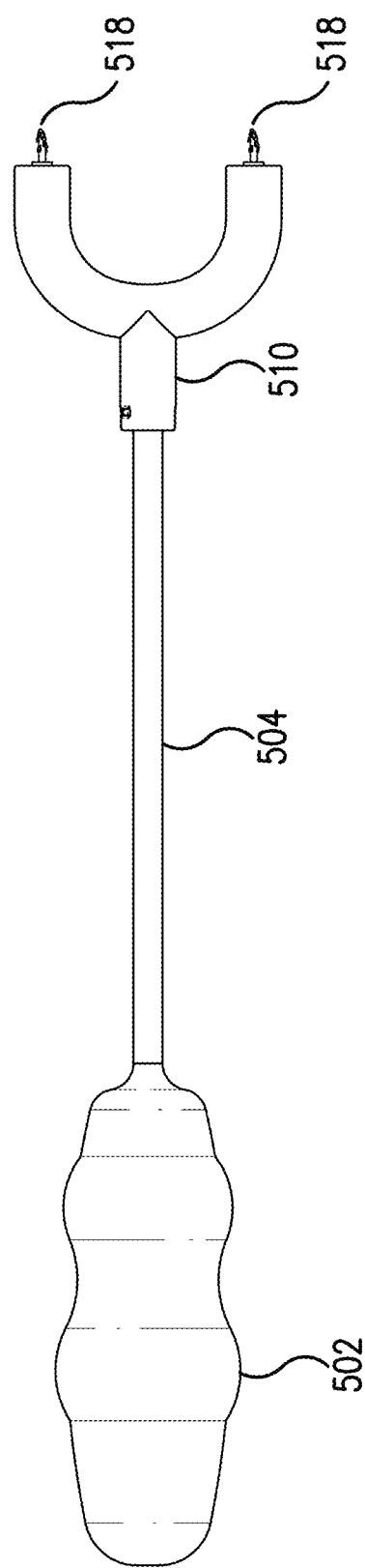
Figure 5E:
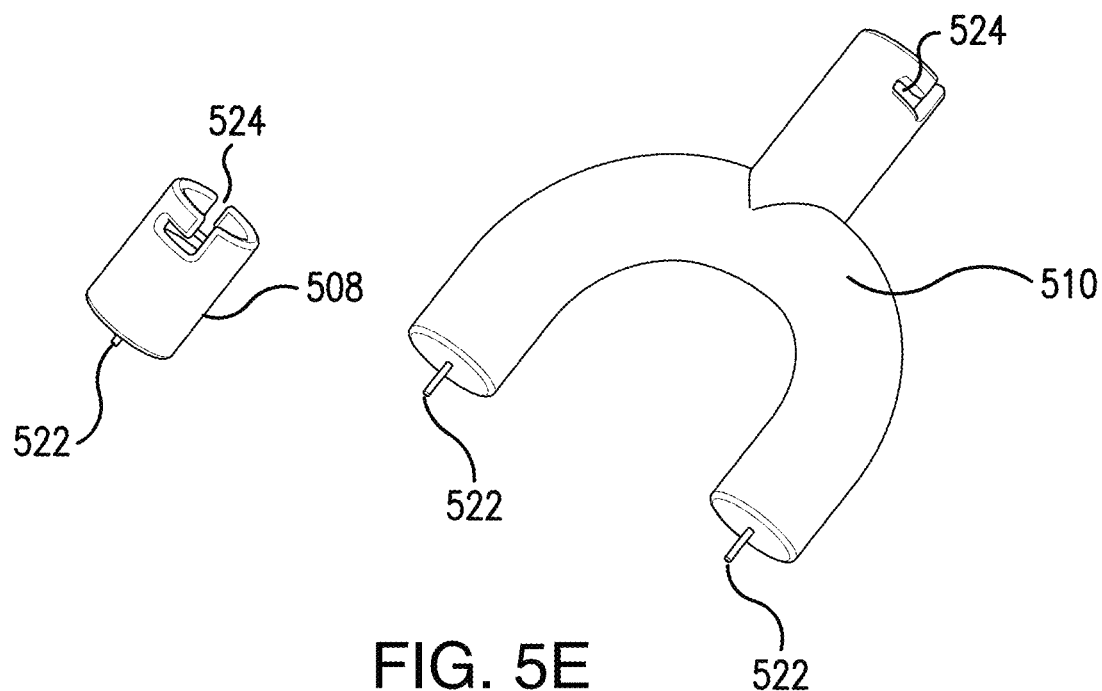
Figure 5F:
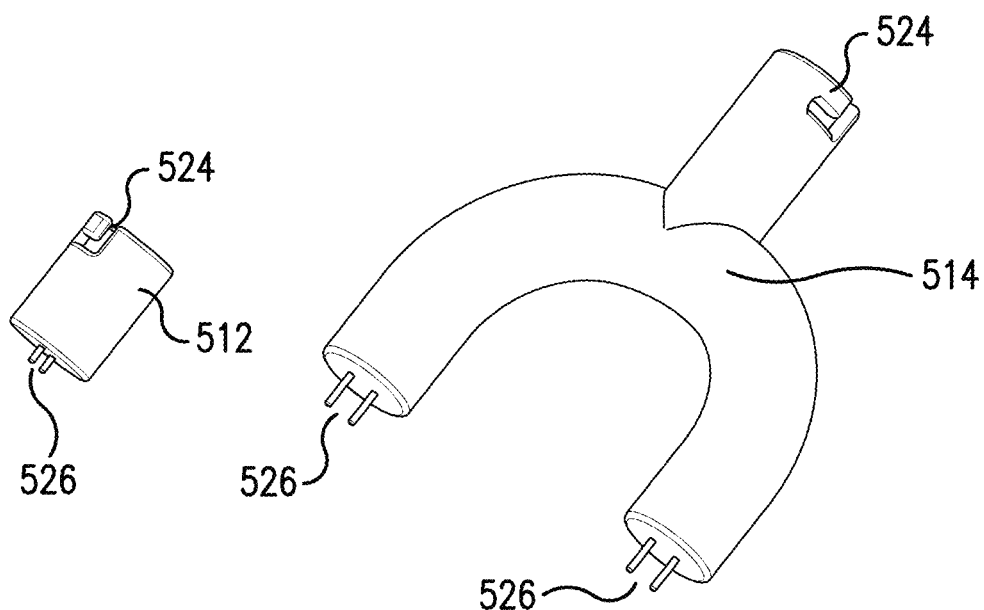

The exemplary embodiment in FIG. 5D depicts a fully assembled mesh fixation device used to manually affix a mesh and tacks to a fascia. The device can include a handle 502, a shaft 504, a dual straight tack adapter 510, and tacks 518. The handle 502 can be used to hold the mesh fixation device by the user (i.e., a surgeon). The shaft 504 can connect the handle 502 and the tack adapter 510. The adapter 510 can be locked to the shaft 504 using a twist-lock mechanism. The tacks 518 can be engaged to the adapter 510 using pins that can be attached to the mating interface.

Figure 5G:
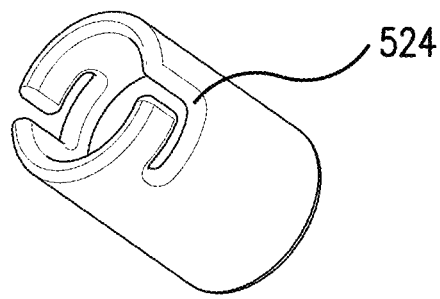
Figure 5H:
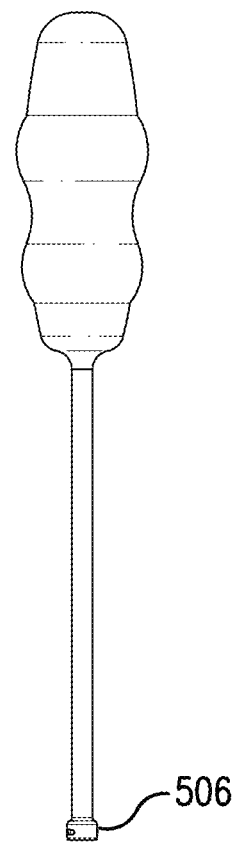
Figure 5H:
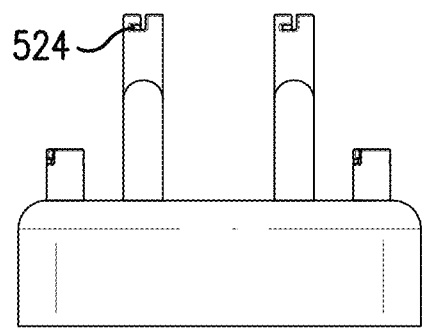
Figure 5K:
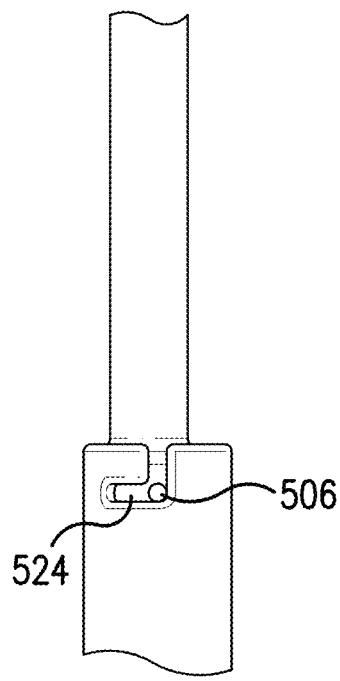
Figure 5L:
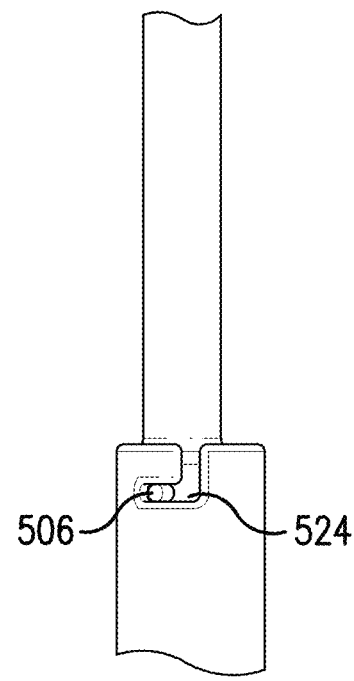
Figure 5M:
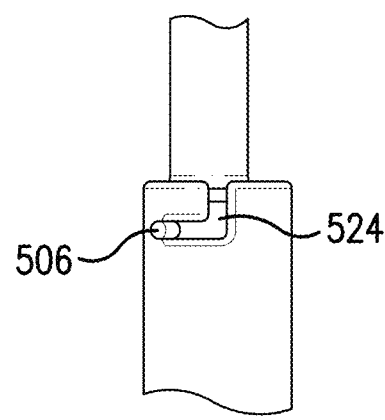

FIGS. 5G-5N illustrate the process of attaching the adapter to the handle using a twist-lock mechanism. FIG. 5G depicts a twist-lock mechanism 524. The twist-lock mechanism 524 can be used to attach the handle (e.g., handle 502) to a tack adapter. The exemplary embodiment in FIG. 5H depicts the locking mechanism 506 being aligned with the twist-lock mechanism 524. FIG. 5I illustrates a magnified view of the locking mechanism 506 and the twist-lock mechanism 524. FIG. 5J depicts the locking mechanism 506 being moved downwardly into the twist-lock mechanism 524. FIG. 5K depicts the locking mechanism 506 being fully inserted into the twist-lock mechanism 524. FIG. 5L depicts the locking mechanism 506 being twisted to the left within the twist-lock mechanism 524. FIG. 5M depicts the locking mechanism 506 being fully rotated into the twist-lock mechanism 524.

Figure 5N:
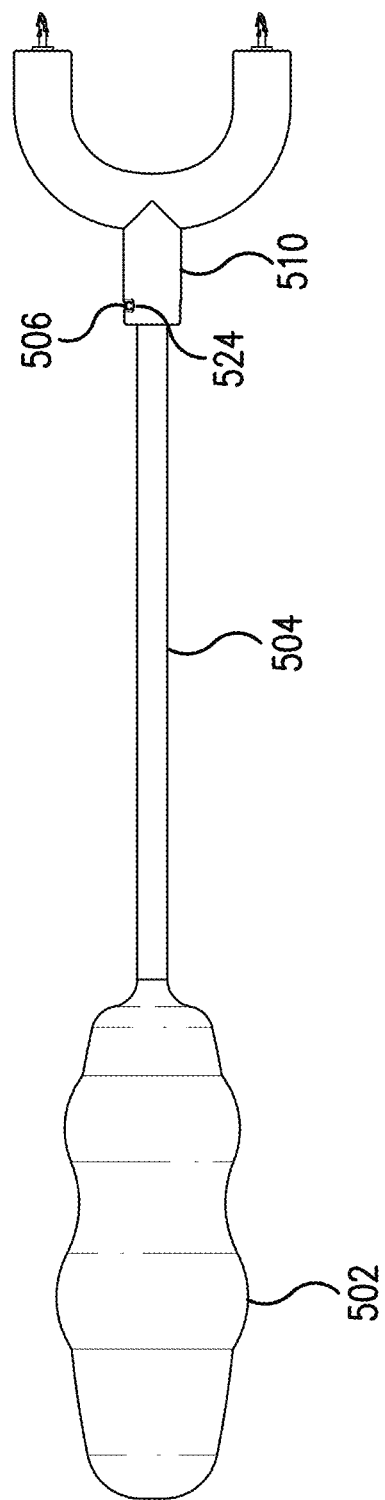

The exemplary embodiment in FIG. 5N depicts a fully locked adapter. The handle 502 and shaft 504 can be attached to the adapter 510 using the twist-lock mechanism 524. The locking mechanism 506 can be fully secured into the twist-lock mechanism 524.

Figure 5O:
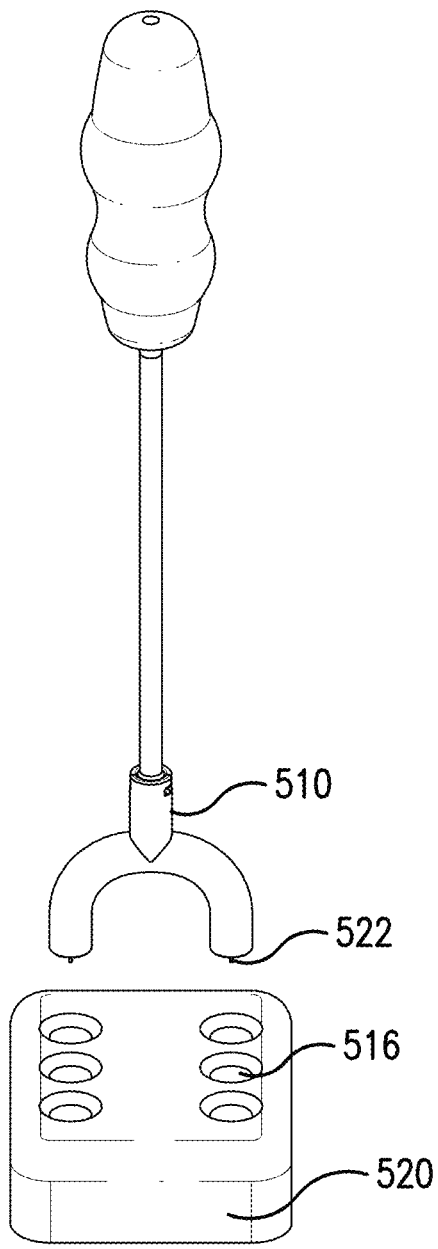
Figure 5P:
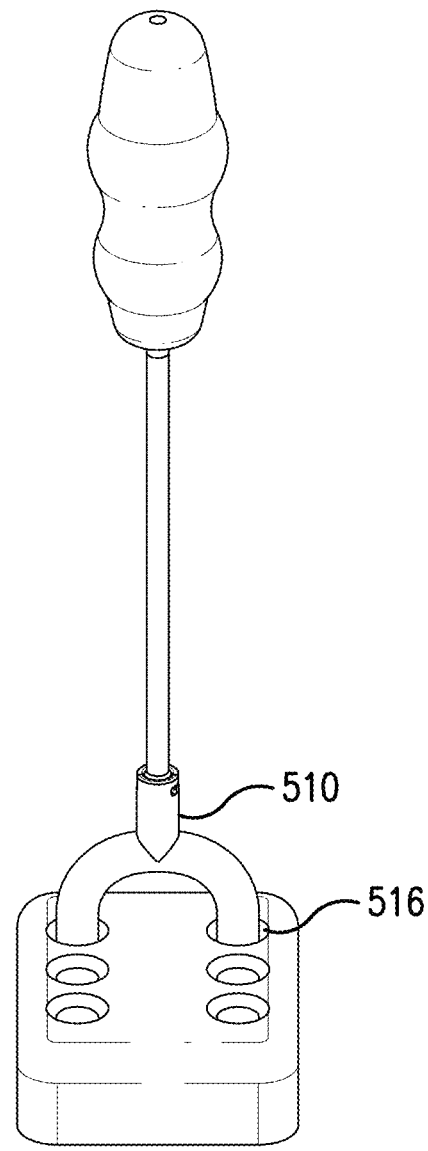
Figure 5R:
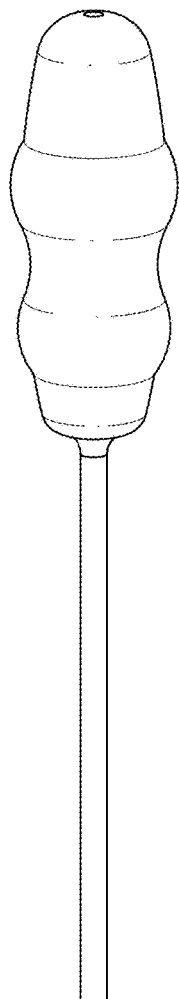
Figure 5R:
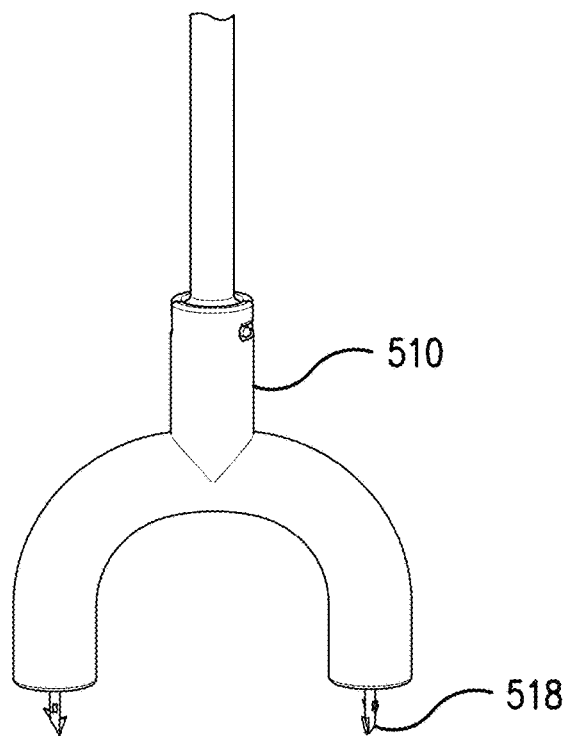
Figure 5S:
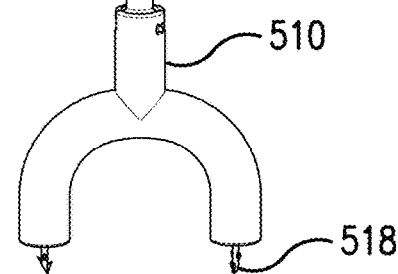
Figure 5S:
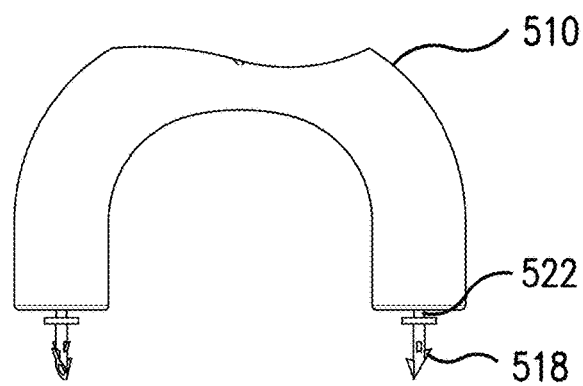
Figure 5Q:
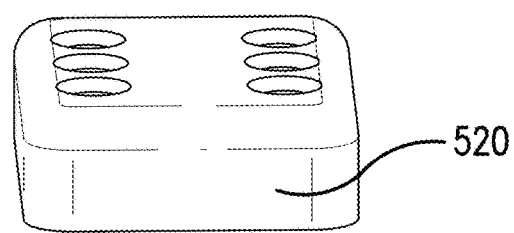

FIGS. 5O-5S illustrate the process of engaging the tacks to the adapter using pins. FIG. 5O depicts the adapter 510 of a mesh fixation device being aligned with a tack tray 520. The tack tray 520 can contain tacks beneath the chamfered holes 516. The pins 522 on the end of the tack adapter can be inserted into the chamfered holes 516 so as to engage the tacks to the end of the tack adapter. FIG. 5P depicts the adapter 510 being inserted into the chamfered holes 516. The chamfered holes 516 can be used to align the pins of the tack adapter with the mating interface of the tacks. FIG. 5Q depicts the tack adapter 510 being removed from the tack tray 520. The pins on the end of the tack adapter can be engaged with the tacks 518. FIG. 5R illustrates a magnified view of the tacks 518 fully engaged to the adapter 510. FIG. 5S illustrates a further magnified view of fully engaged adapter. 510. The pins 522 on the tack adapter can fit into the mating interface on the tacks 518, thereby engaging them.

Figure 5T:
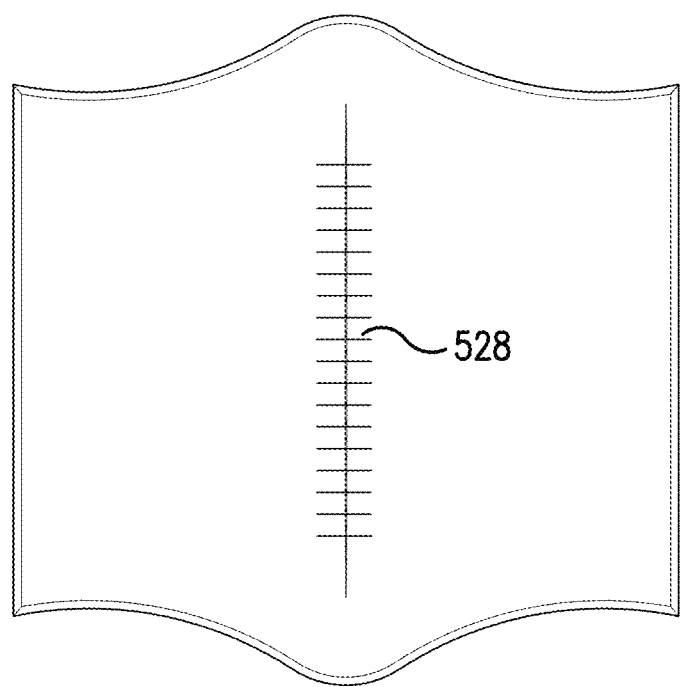
Figure 5U:
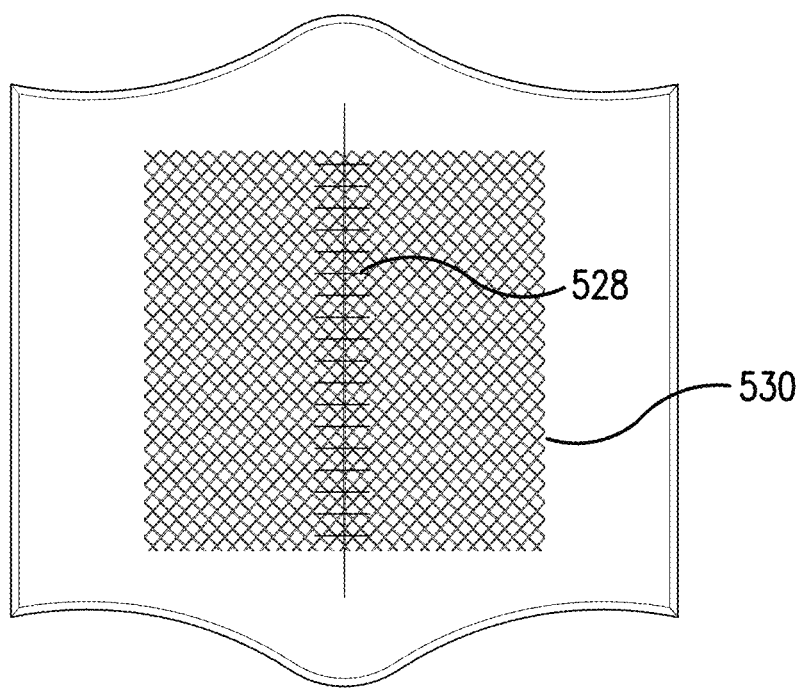
Figure 5W:
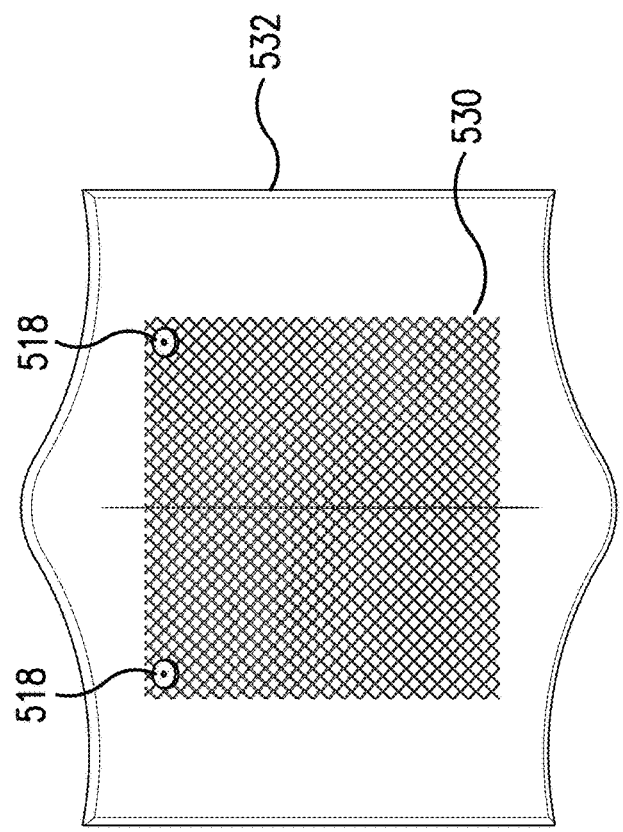
Figure 5V:
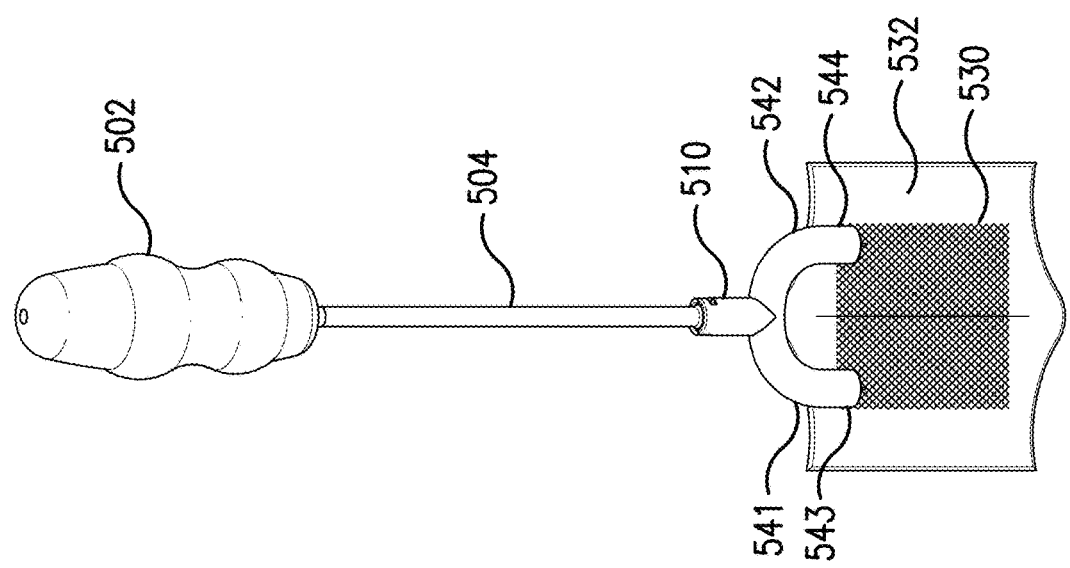

FIGS. 5T-5Z illustrate the procedure for fixing a mesh onto a fascia using an exemplary mesh fixation device. FIG. 5T depicts a sutured incision 528. FIG. 5U depicts a mesh 530 that can be placed on top of a sutured incision 528. With reference to FIG. 5V, the device includes a first arm 541 and a second arm 542 having distal ends 543 and 544, respectively. The distal end of the first arm 541 is spaced from the distal end of the second arm 542 to engage with the mesh on opposing sides of the fascial incision 528. The method further includes deploying fixation elements from at least one of the first and second arms to affix the reinforcing material on opposing sides of the incision 528. As embodied herein, the distal ends of the first and second arms can push tacks into the fascia 532 to secure the mesh 530.

In accordance with another aspect of the disclosed subject matter, the method for affixing reinforcing material can include application of lateral tension on the reinforcing material by increasing a distance between opposing sides of the reinforcing material from a first distance to a second distance. As discussed further herein, the lateral tension can be applied by spreading the distal ends 543 and 544 of the first and second arms using a spreading mechanism. As discussed further herein, the distal ends 543 and 544 can releasable couple with the reinforcing material, which can facilitate lateral tensioning and mesh placement. When the distal ends 543 and 544 are releasably coupled to the reinforcing material, increasing a distance between the distal ends can correspondingly increase a distance between opposing sides of the reinforcing material. Applying a tension to the reinforcing material before affixation, or tension setting, can help reduce tension across the primary repair such that the primary repair is unloaded and thus the mesh serves as a load-sharing measure.

Figure 5Y:
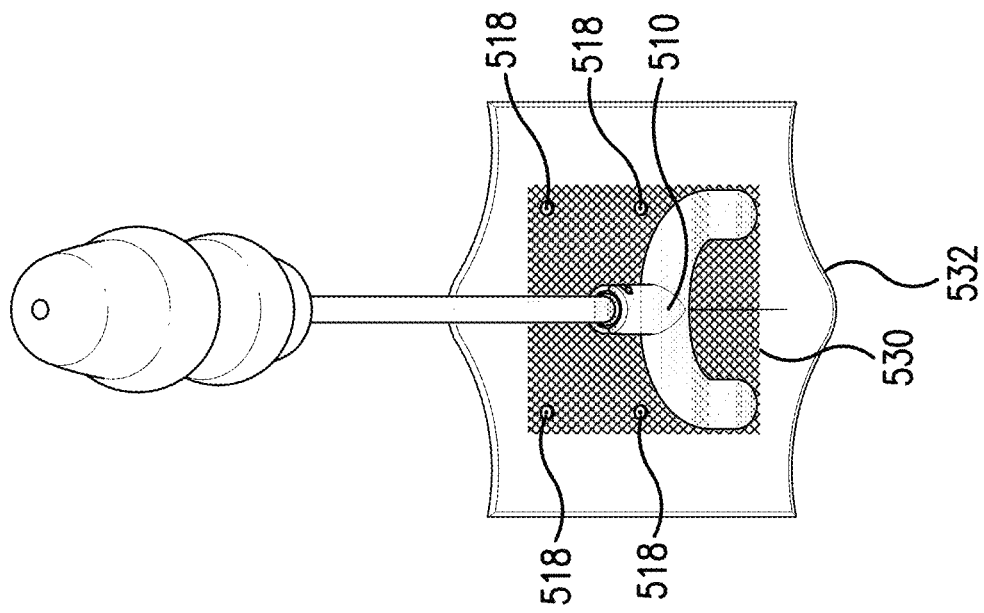
Figure 5X:
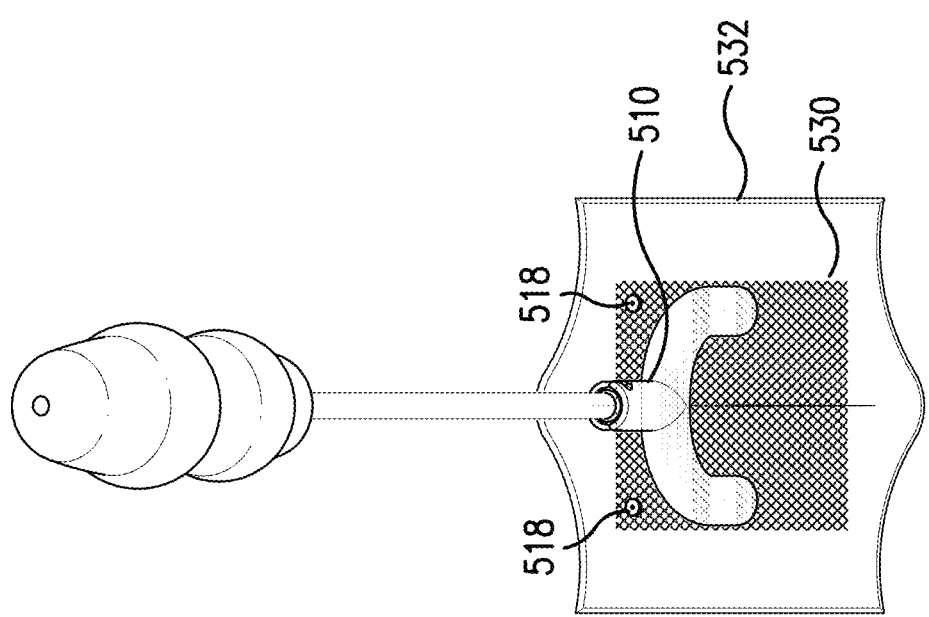
Figure 5Z:
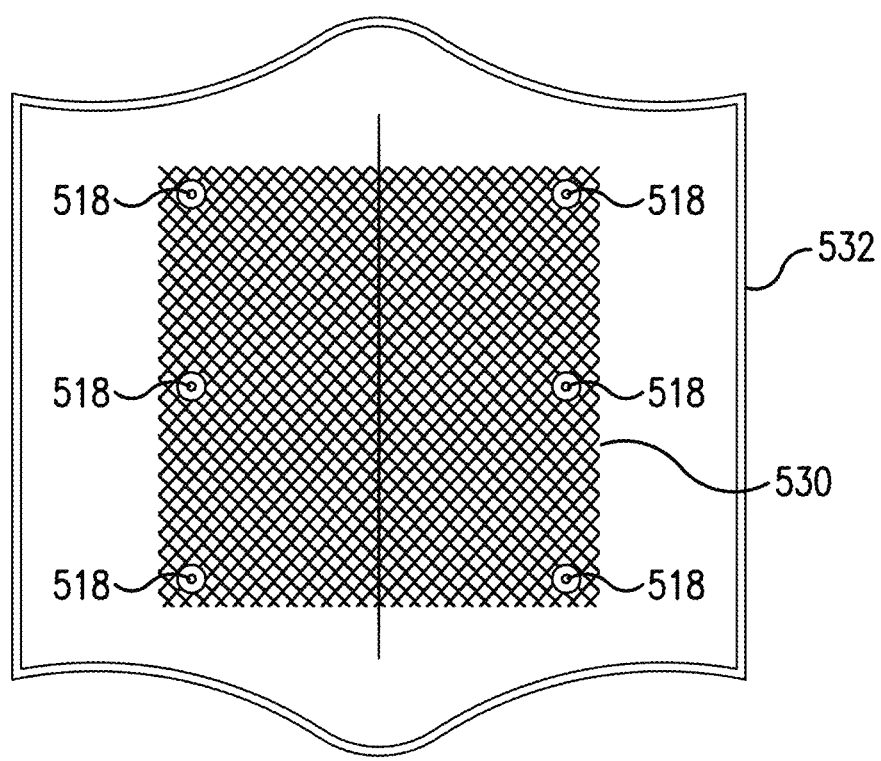

The device can be controlled by grasping the handle 502. The handle 502 can provide control of the adapter 510 and tacks that can be affixed to the mesh 530. The ability to use the device with different tack adapters or distal ends can provide flexibility and can allow the distal ends of the first and second arms to be selected to suite different surgical needs. For example, in some embodiments, the shaft 504 can be engaged to multiple tack adapters, giving the user the choice between a straight tack or a curvilinear tack and between affixing a single tack or two tacks simultaneously, as further discussed herein. In some embodiments, the shaft 504 can be long and/or thin to allow for easy access to the abdominal wall. FIG. 5W depicts two tacks 518 that can be fully penetrated into the fascia 532 so as to affix the mesh 530. FIG. 5X depicts two affixed tacks 518 and the mesh fixation device. The device can be fully engaged so the tack adapter 510 can continue to push tacks into the fascia 532 in order to secure the mesh 530. FIG. 5Y depicts four affixed tacks 518 and the mesh fixation device. The device can be fully engaged so the tack adapter 510 can push the two more tacks into the fascia 532 to fully affix the mesh 530. FIG. 5Z depicts a fully affixed mesh 530. The mesh 530 can be fully affixed by penetrating six tacks 518 into the fascia 532.

Figure 6A:
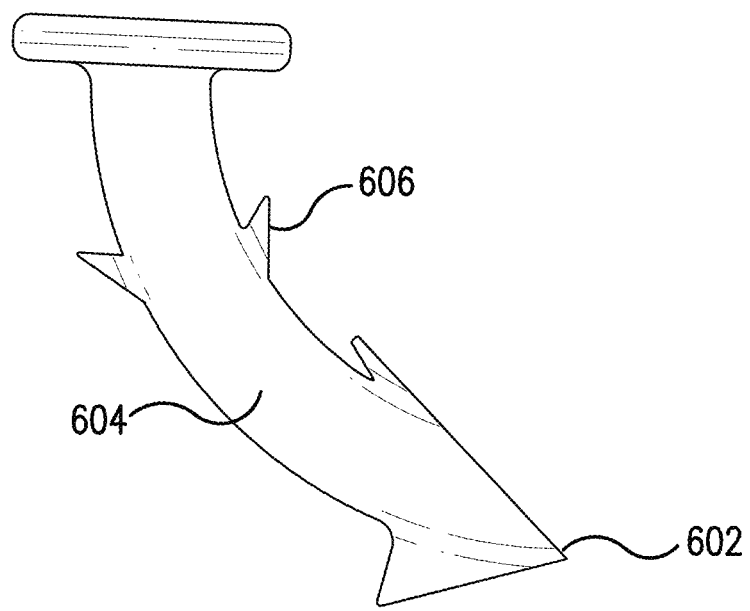
FIGS. 6A-6H illustrate diagrams of curvilinear tacks in accordance with an exemplary embodiment of the disclosed subject matter.
Figure 6B:
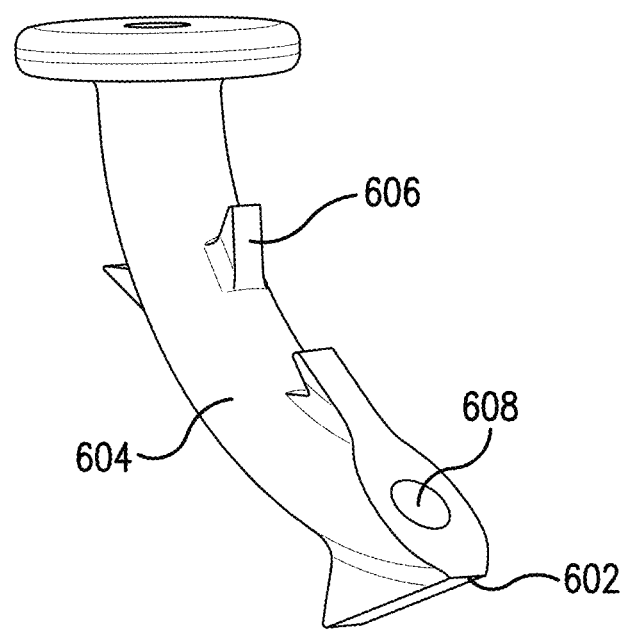

FIGS. 6A and 6B illustrate perspective views of an exemplary curvilinear tack. The exemplary embodiment in FIG. 6A depicts a curved tack 604 with a sharp head 602 and barbs 606. The sharp head 602 can be used to penetrate the fascia. The ninety degree curve in the curved tack 604 can allow the tack 604 to maximize its grasping ability by exerting onto a greater portion of the fascial surface than a conventional straight tack. The barbs 606 can add fixation strength to the tack 604. FIG. 6B depicts a different view of the tack in FIG. 6A, showing a hollow cavity 608 in addition to the sharp head 602 and barb 606. In some embodiments, the hollow cavity 608 can be a path for fluids to pass through the tack. The exemplary curvilinear tack can allow the tack to penetrate the fascia, while providing lateral tension to the mesh. The 90 degree curve in the tack can allow the tack to grab onto a portion of the mesh as the tack is penetrated into the mesh. As the tack is pushed down and through the mesh and/or the fascia, the tack can move slightly outward because of its curved shape. This slight outward movement of the tack during mesh and/or fascial penetration can inherently move the mesh along with the tack, thereby tensioning the mesh by a few millimeters.

Figure 6C:
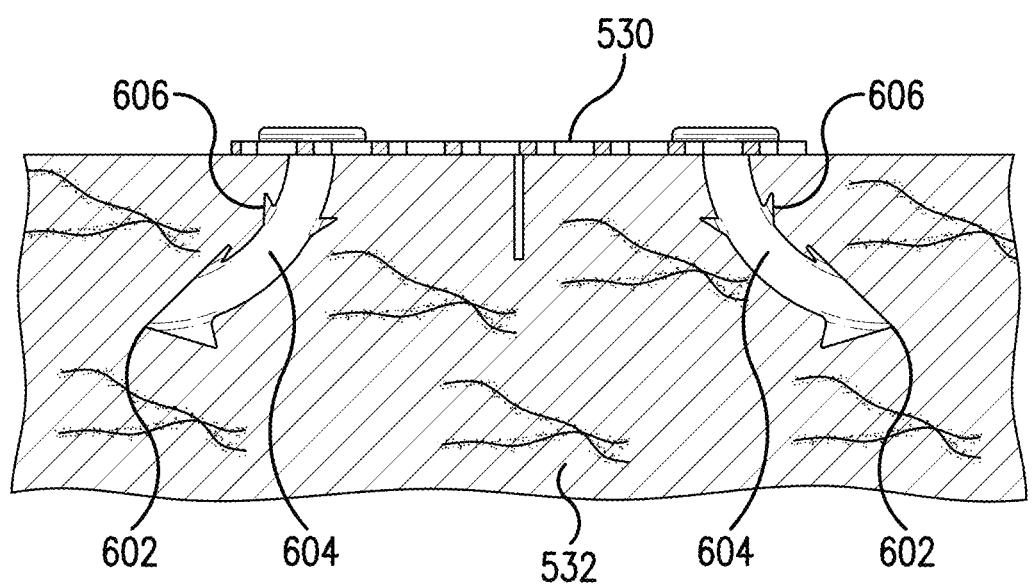

FIG. 6C illustrates two exemplary curved tacks that can be used to secure mesh to the fascia. The exemplary embodiment in FIG. 6C depicts curved tacks 604 with sharp heads 602 and barbs 606. The sharp head 602 of the tacks can be used to penetrate the mesh 530 and the fascia 532. The barbs 606 can be used to affix mesh 530 to the fascia 532.

Figure 6D:
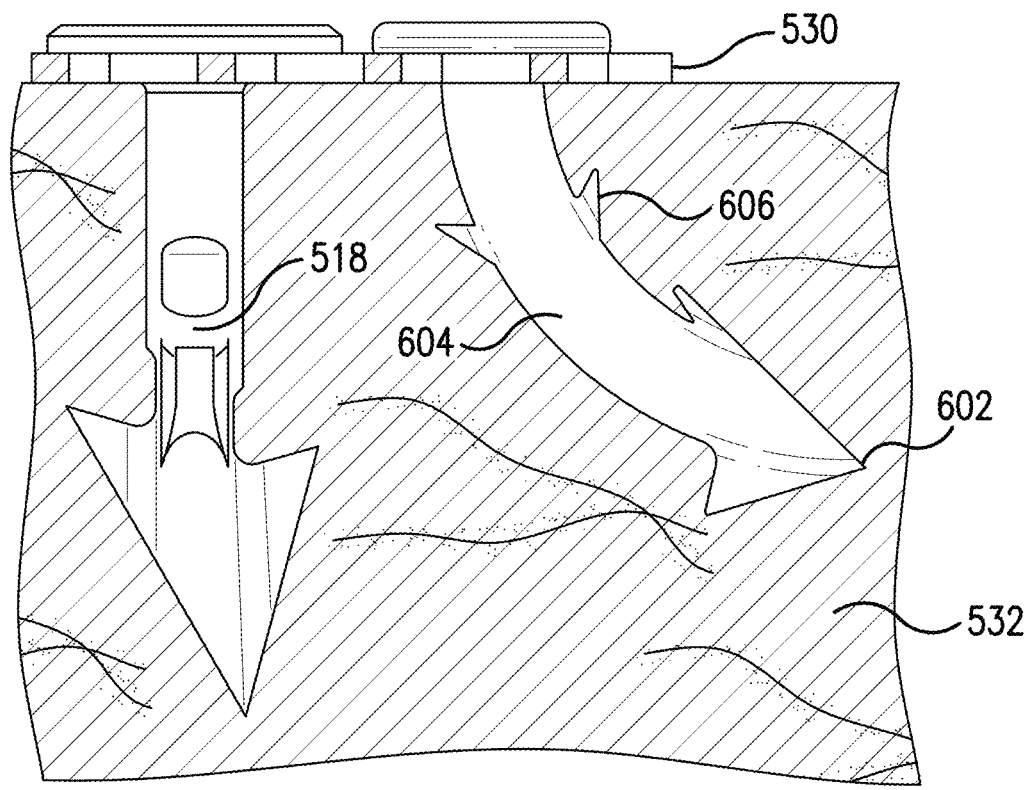

FIG. 6D illustrates an exemplary comparison of a curvilinear curved tack with an straight tack. The straight tack 518 can enter straight into the fascia 532. Upon penetrating the fascia, the curvilinear tack 604 can enter the fascia 532 at a curve. The curved feature of the curvilinear tack 604 can allow it to penetrate the fascia at a shallower distance than the straight tack 518. The curvilinear tack 604 can create improved affixation strength to the fascia than traditional tacks by using the barbs 606 to grasp on the fascial tissue, while decreasing the risk of harm by penetrating an undesired area such as the bowel and/or other organs beneath the fascia. In some embodiments, by grasping onto an effectively greater surface area of the tissue than a conventional straight shaped tack, the disclosed curved tack can achieve better affixation strength. Because the curved tack can penetrate the fascia less deeply than a conventional straight-shaped tack, the curved tack can protect the organs underneath the fascia from inadvertent puncturing.

Figure 6E:
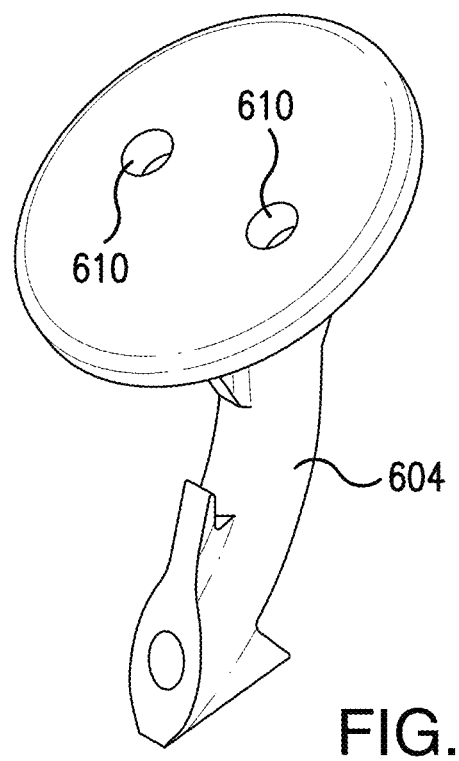
Figure 6F:
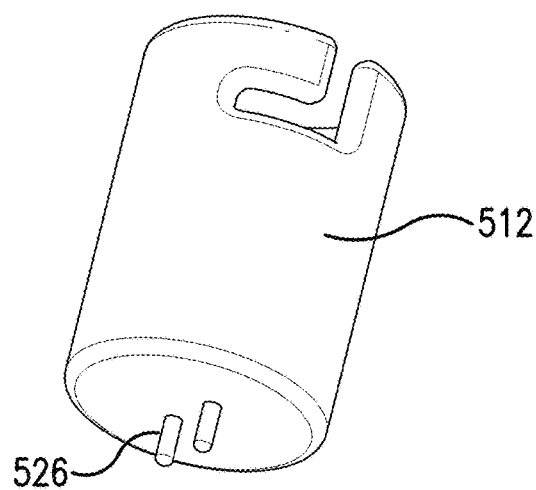

FIG. 6E-6H illustrate the process of attaching a curvilinear curved tack to a mesh fixation device. The exemplary embodiment in FIG. 6E depicts a curved tack 604 from a raised angle. The curved tack can include a mating interface with two holes 610 that can be engaged by an adapter. The exemplary embodiment in FIG. 6F depicts a single curvilinear tack adapter 512 with two pins 526 that can engage the holes in the mating interface of the curved tack.

Figure 6G:
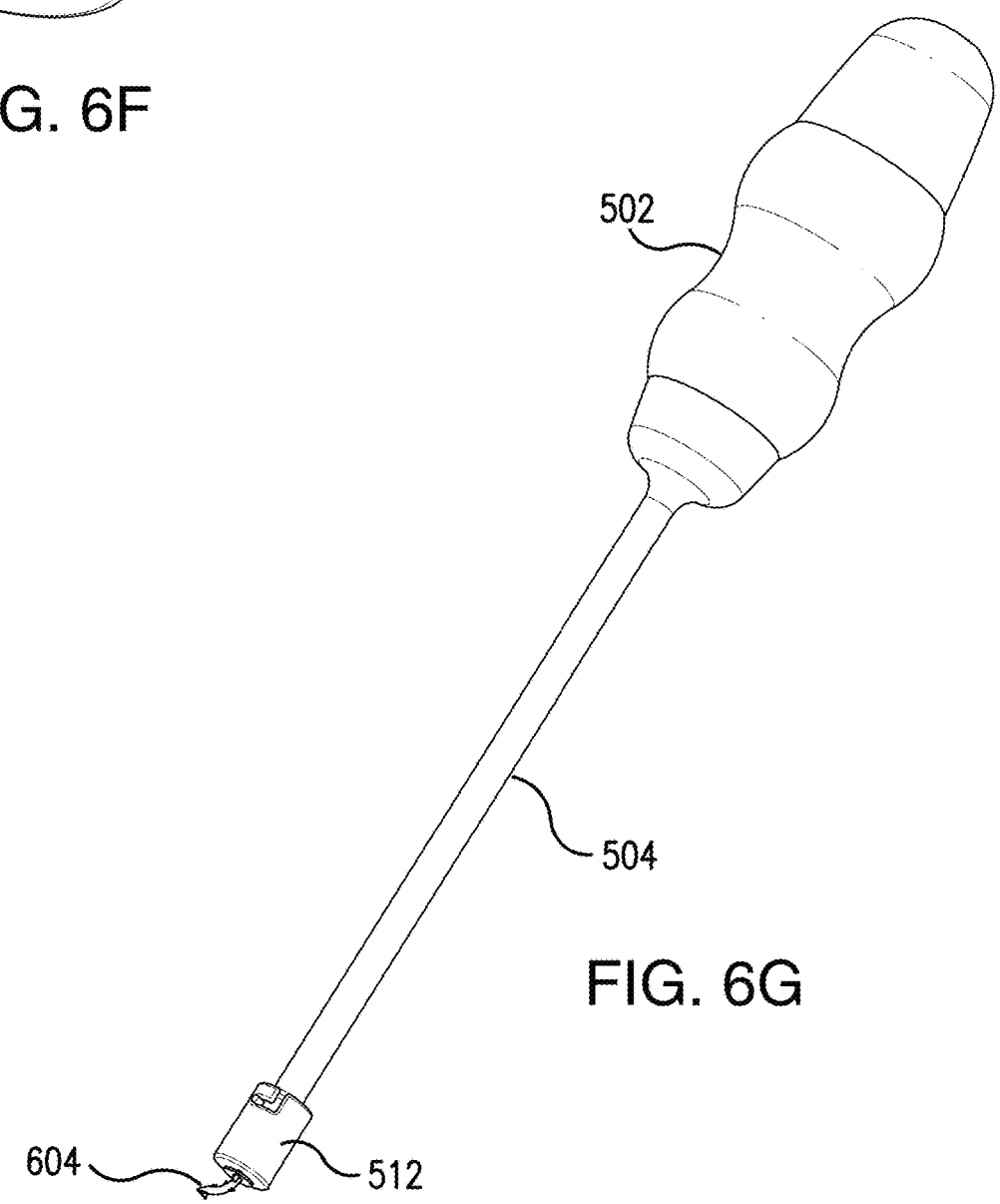
Figure 6H:
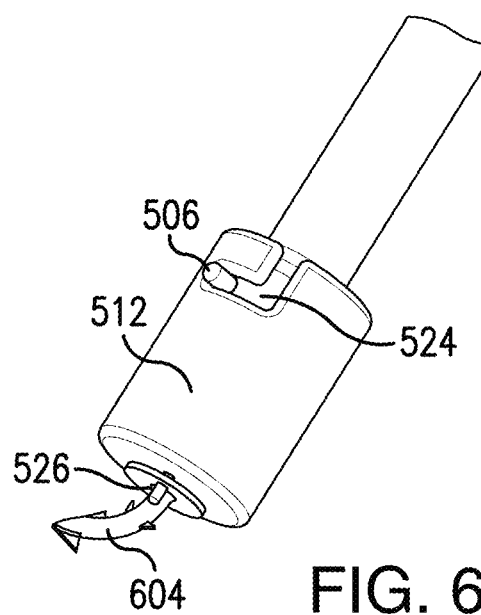

FIG. 6G depicts an exemplary fully assembled mesh fixation device. The device can include a handle 502, a shaft 504, a single curvilinear tack adapter 512, and a curved tack 604. FIG. 6H illustrates a magnified view of the mesh fixation device illustrated in FIG. 6G. FIG. 6H shows a single curvilinear tack adapter 512 whose pins 526 can be matingly engaged to a curved tack 604. The tack adapter 512 can be attached to the mesh fixation device using a locking mechanism 506 and a twist-lock mechanism.

Figure 7A:
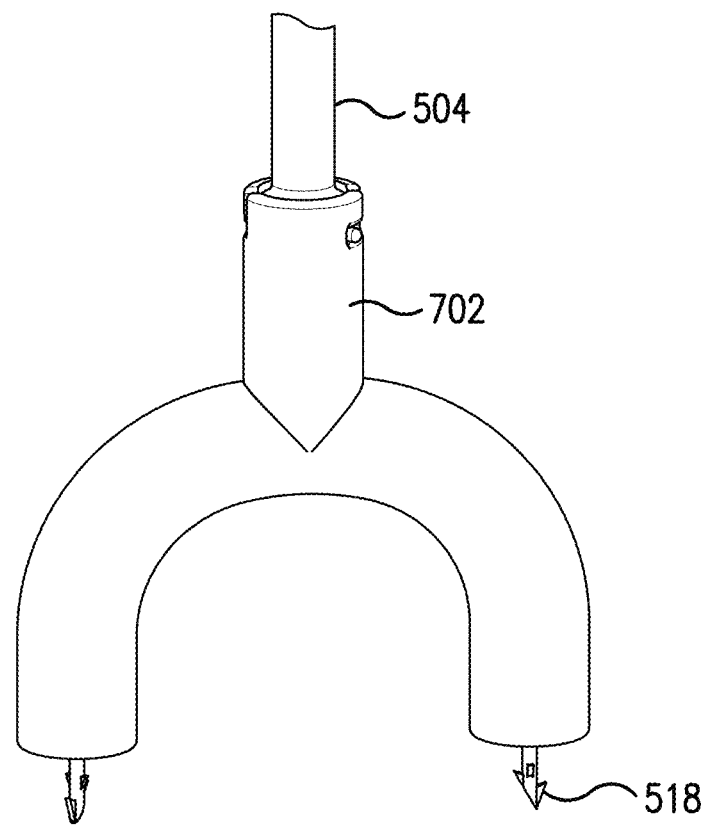
FIG. 7A illustrates a diagram of a spring-loaded tack adapter in accordance with an exemplary embodiment of the disclosed subject matter.

FIG. 7A illustrates an exemplary adapter with a spring. The adapter 702 can be attached to the shaft 504 using a twist-lock mechanism and can engage up to two tacks 518 simultaneously. The adapter 702 can contain a spring, which allows for tack affixation on uneven surfaces.

Figure 7B:
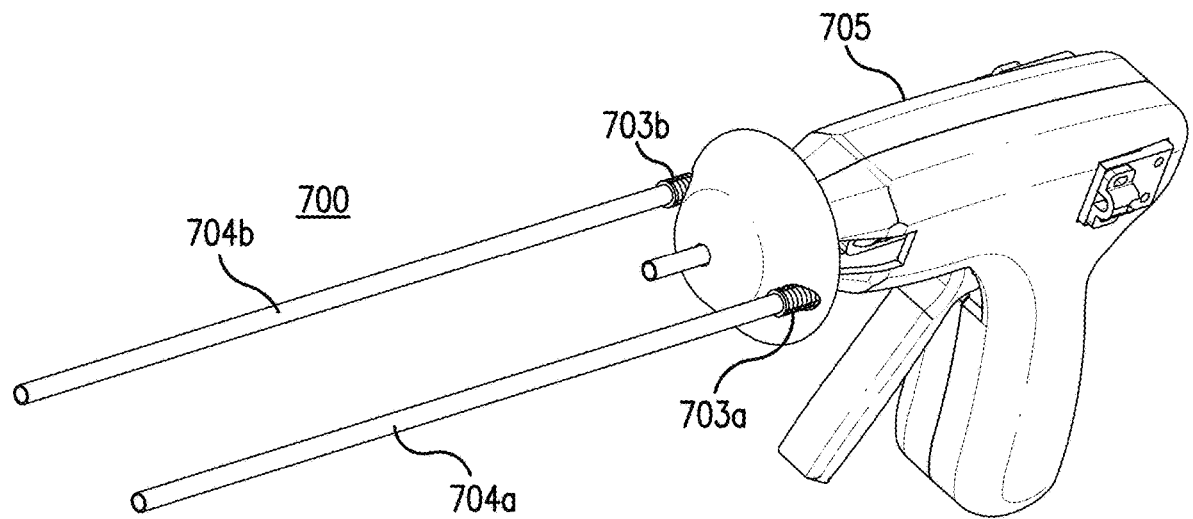
FIG. 7B is a perspective view of a mesh fixation device with springs in accordance with an exemplary embodiment of the disclosed subject matter.
Figure 7C:
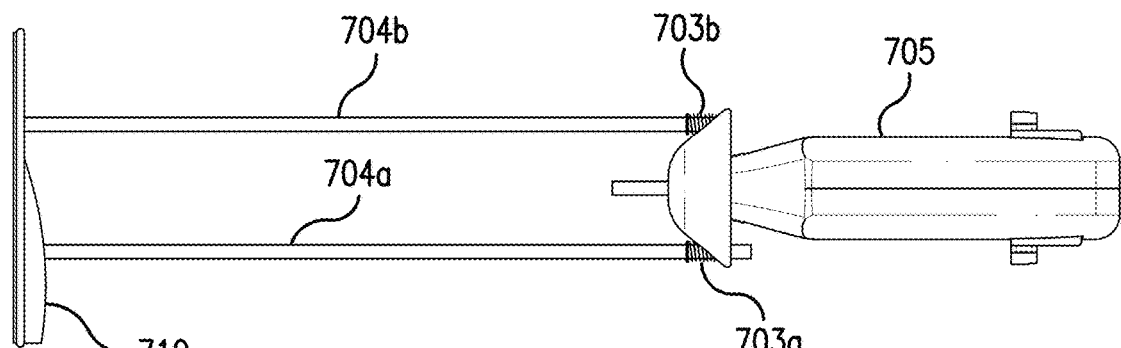
FIG. 7C is a top view of the mesh fixation device of FIG. 7B engaged with fascia having an uneven surface.

With reference to FIG. 7B, and in accordance with another aspect of the disclosed subject matter, the fixation device can include one or more springs coupled with one or more arms. For purpose of example, and not limitation, and as embodied herein, the mesh fixation device 700 includes a housing 705 and first and second arms 704a and 704b, respectively, extending away from the housing 705. The first arm 704a and second arm 704b are coupled to springs 703a and 703b, respectively. The ability of the springs 703a and 703b to compress and articulate can facilitate tack deployment and reinforcing material affixation on fascia with uneven surfaces. Referencing FIG. 7C, the first and second arms of the device 700 are depicted engaging the uneven surface of fascia 710. As embodied herein, as a user applies pressure to engage the arms 704a and 704b with the fascia 710, spring 703b can compress to allow for more even engagement with the fascia during engagement at multiple locations. As embodied herein, springs 703a and 704a can be compressed linearly and arms 704a and 704b can remain in parallel alignment during engagement with fascia 710. Alternatively, one or more of springs 703a and 703b can deflect laterally such that the distal ends, 707a and 707b, of arms 704a and 704b can diverge to facilitate out of plane affixation, as discussed further herein. As embodied herein, springs 703a and 703b couple arms 704a and 704b to a distal location of the housing 705; however, one or more springs can be coupled to one or more arms at any suitable location. For example, one or more arms can include a proximal portion and a distal portion, and a spring can be coupled between the proximal and distal portions.

Figure 8:
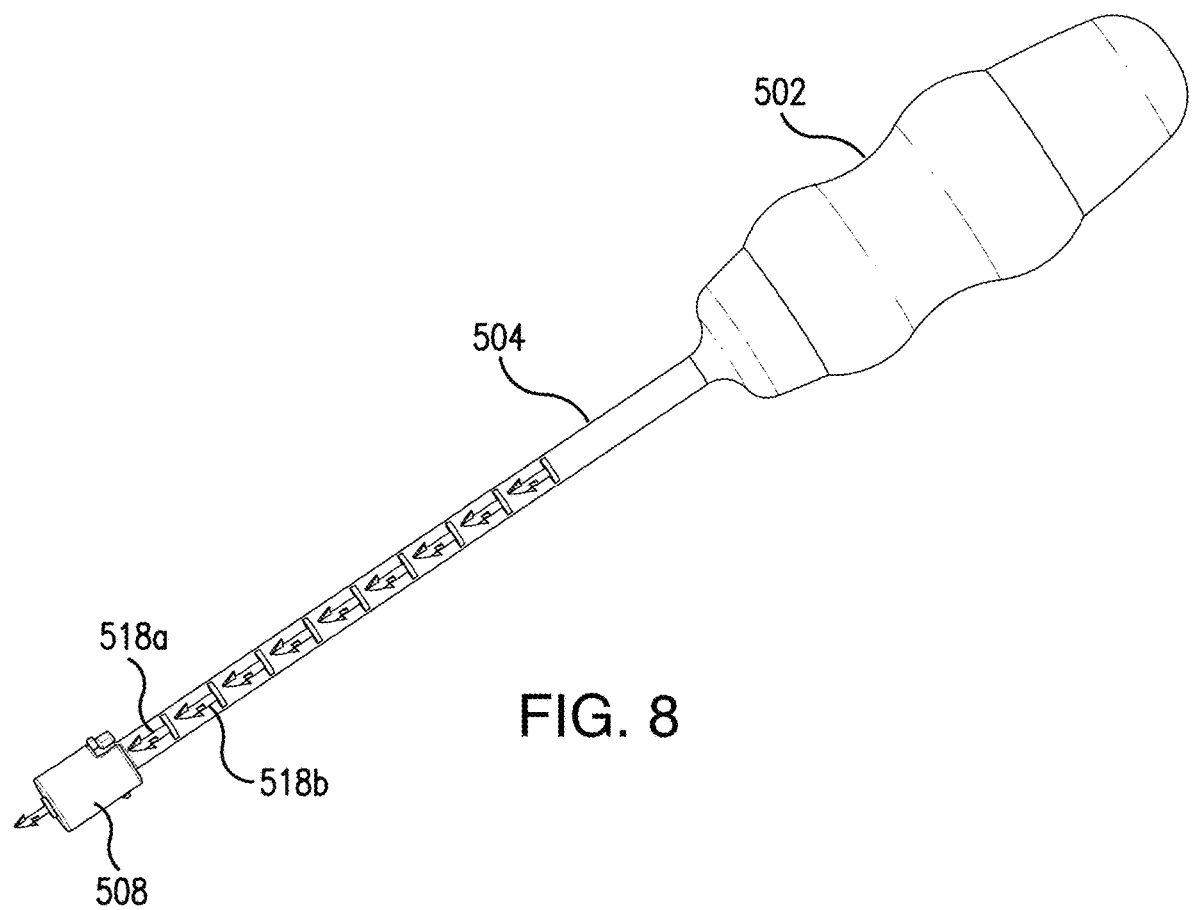
FIG. 8 illustrates a diagram of a mesh fixation device pre-loaded with multiple tacks in the shaft in accordance with an exemplary embodiment of the disclosed subject matter.

FIG. 8 illustrates an exemplary mesh fixation device including tacks pre-loaded in its shaft. The exemplary embodiment depicted by FIG. 8 illustrates a handle 502, a shaft 504, an adapter 508, and tacks 518a and 518b. The tacks 518a and 518b can be stored in the shaft 504 in a stacked manner such that the tack 518 can be automatically loaded for deployment after tack 518a has been deployed to the fascia to be affixed to the surgical mesh and/or fascia. In some embodiments, the shaft 504 can also include a spring component inside the shaft 504 that can advance the tacks forward as they are deployed, so that the tacks reload on their own. For example, as one tack is deployed and affixed onto the mesh, the next tack can pop out and be positioned to be affixed onto the mesh as well partly due to the spring component inside the shaft 504 which can cause the next tack to pop out as the previously loaded tack is deployed.

Figure 9A:
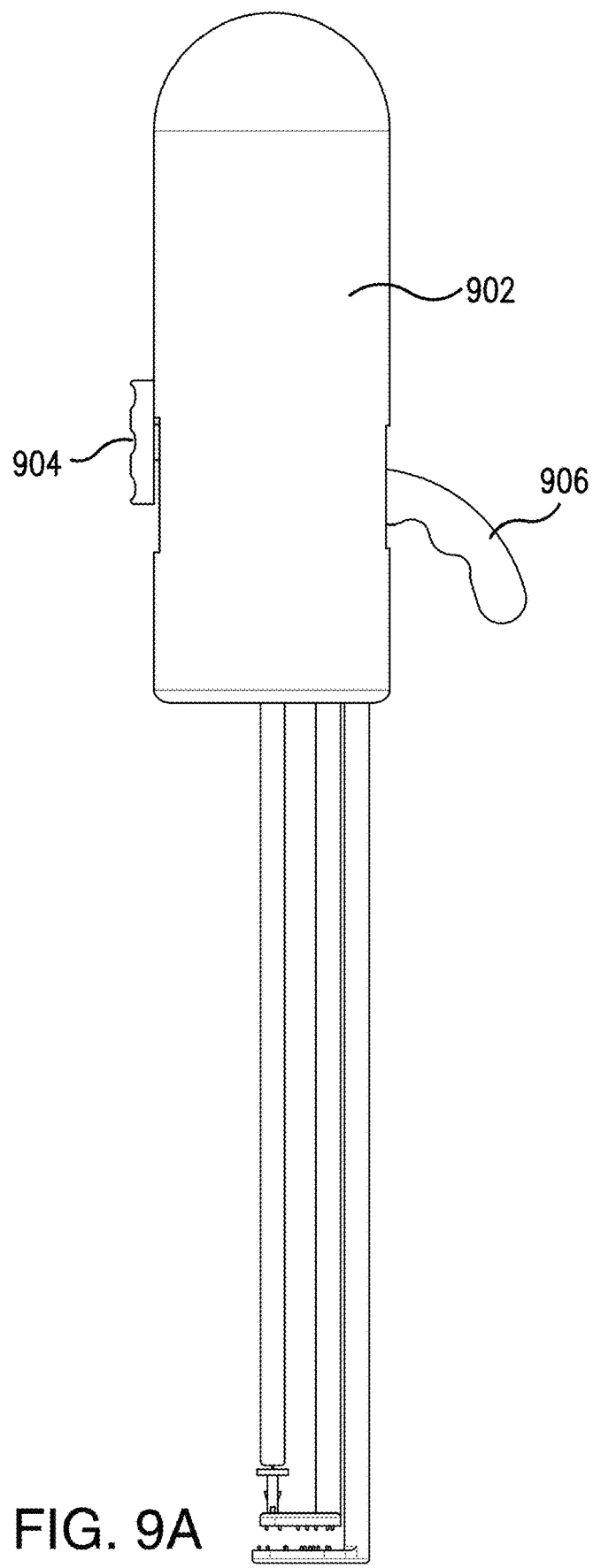
FIGS. 9A-9T illustrate different views of an exemplary mesh fixation device having a mesh positioning component to position and tension the mesh in accordance with an exemplary embodiment of the disclosed subject matter.
Figure 9B:
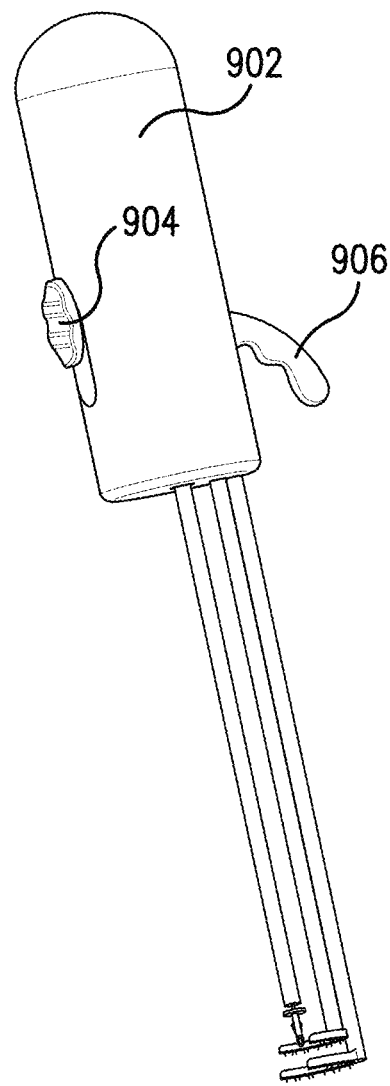
Figure 9C:
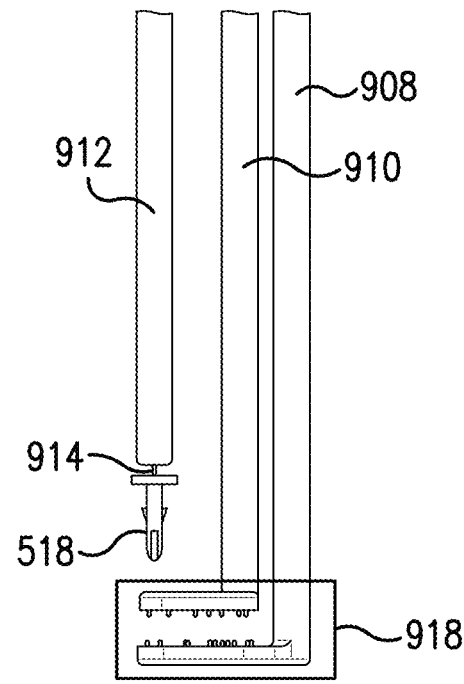

FIGS. 9A-9J illustrate the design components of an exemplary mesh fixation device. The exemplary embodiment depicted by FIG. 9A illustrates manual tacker handle having a handle 902, a slider button 904, and a triggering mechanism 906. The handle 902 can be used to hold the device. The slider button 904 can control the tacking component as illustrated in FIG. 9C. The triggering mechanism 906 can control the mesh positioning component as illustrated in FIG. 9C. FIG. 9B depicts a different view of the exemplary manual tacker handle in FIG. 9A, showing a handle 902, a slider button 904, and a triggering mechanism 906.

The exemplary embodiment depicted by FIG. 9C illustrates a magnified view of the lower portion of the exemplary mesh fixation device. The mesh fixation device can include an adjustable mesh positioning component 908, a fixed mesh positioning component 910, a tacking component 912, a pin 914, a mesh grabbing component 918, and a tack 518. The adjustable mesh positioning component 908 can be moved up and down in relation to the fixed mesh positioning component 910, which does not move, to grasp a mesh. The tacking component 912 can be moved up and/or down to push the tack 518 through the mesh and into the fascia. The tack 518 can be held in place to the tacking component 912 using the pin 914. The mesh can be grasped in the mesh grasping component 918.

Figure 9D:
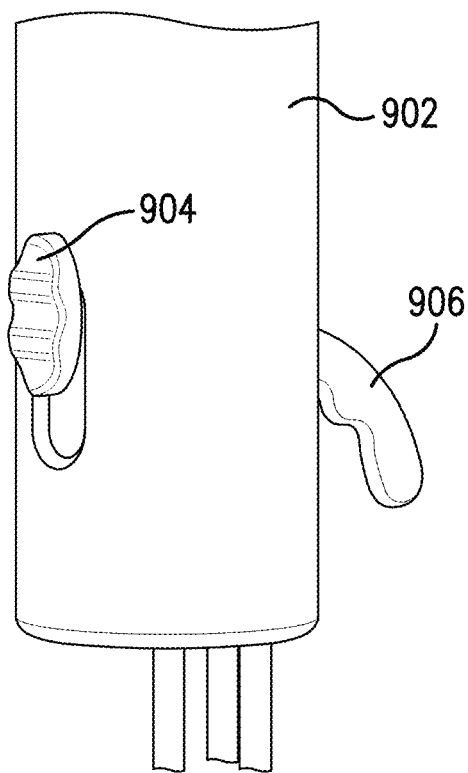
Figure 9E:
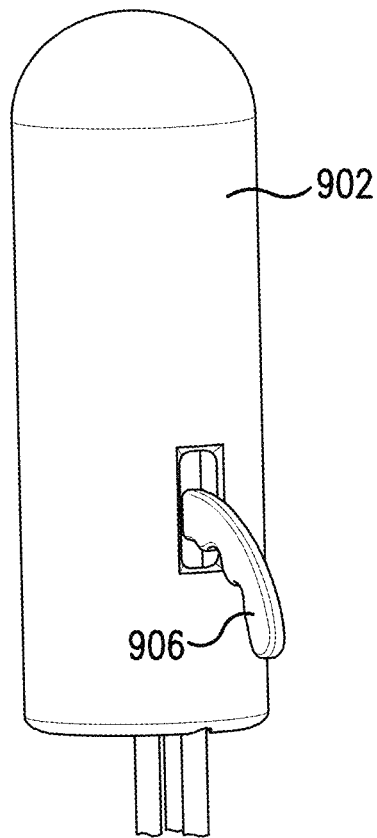

FIG. 9D depicts an enlarged view of a handle 902 and slider button 904. The slider button 904 can slide downwards to move the tacking component downwards to push the tack through the mesh into the fascia. FIG. 9E depicts an enlarged view of a handle 902 and triggering mechanism 906. The triggering mechanism 906 can be moved from the bottom jaw up so as to move the adjustable mesh positioning component upwards to clamp the mesh positioning component onto the mesh. In some embodiments, the user of the mesh fixation device can be provided with full spatial control of the mesh strip to allow the user to manipulate the mesh fixation device to place the mesh in a desired location and then to subsequently affix the mesh onto the fascia with tacks.

Figure 9F:
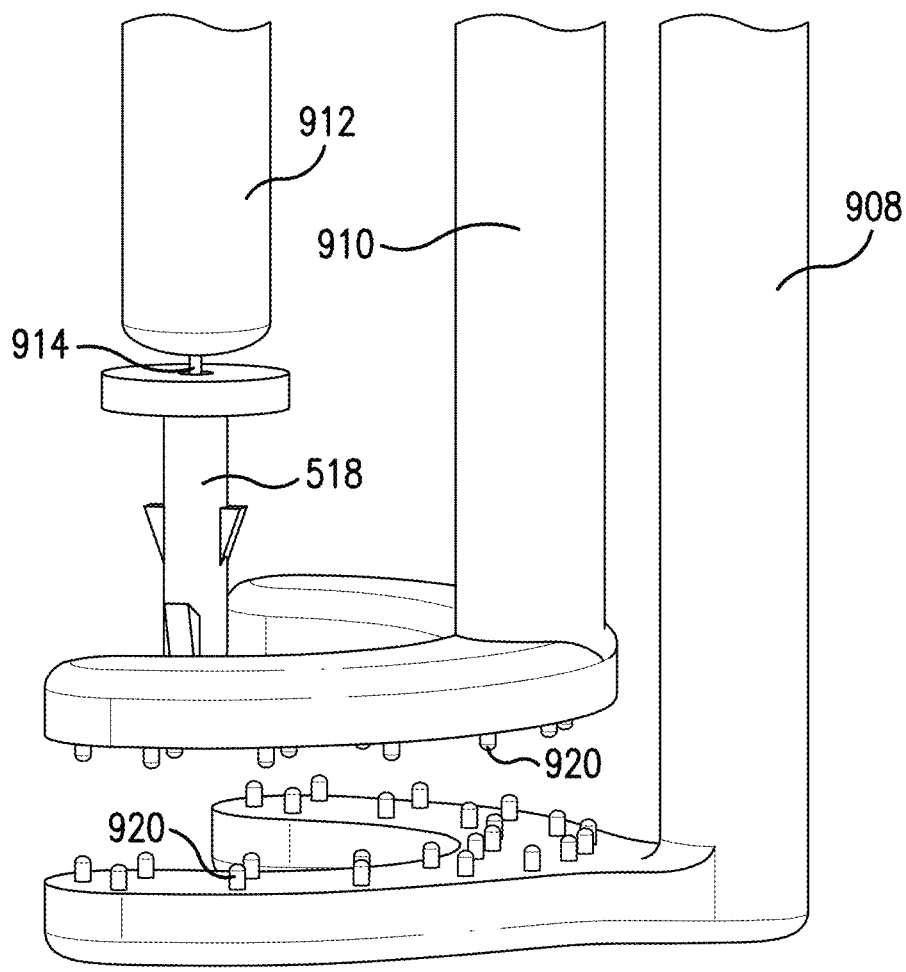

FIG. 9F depicts an exemplary embodiment of the lower portion of the exemplary mesh fixation device. The exemplary mesh fixation device can include the adjustable mesh positioning component 908 and the fixed mesh positioning component 910. The adjustable mesh positioning component 908 can be moved upwards towards the fixed mesh positioning components 910 to grasp the mesh. The mesh positioning components (e.g., components 908 and 910) can include spikes 920 to assist the mesh positioning components grasp on to the mesh. In some embodiments, the spikes 920 can also fit inside of the holes of the mesh in order to prevent the mesh from sliding out of the clamp 920, thereby giving the user of the mesh fixation device with improved spatial control of the mesh strip.

Figure 9G:
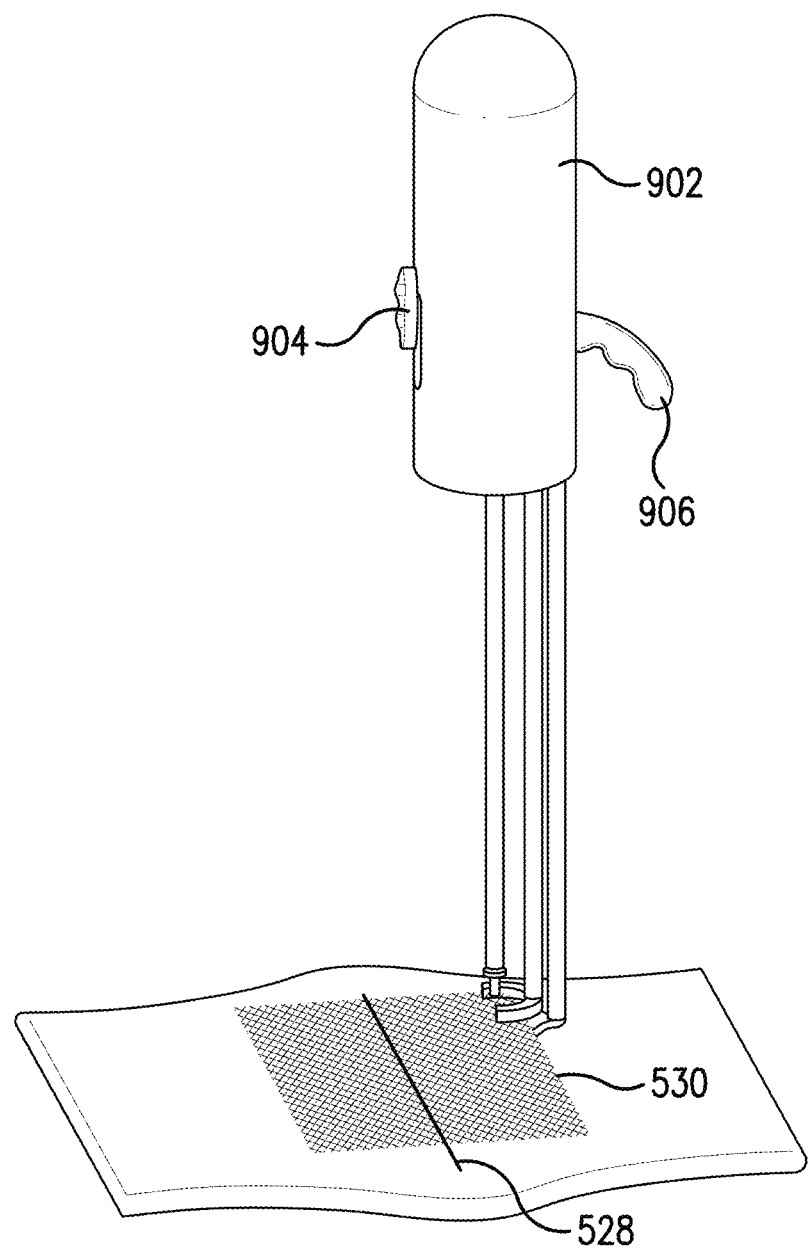
Figure 9H:
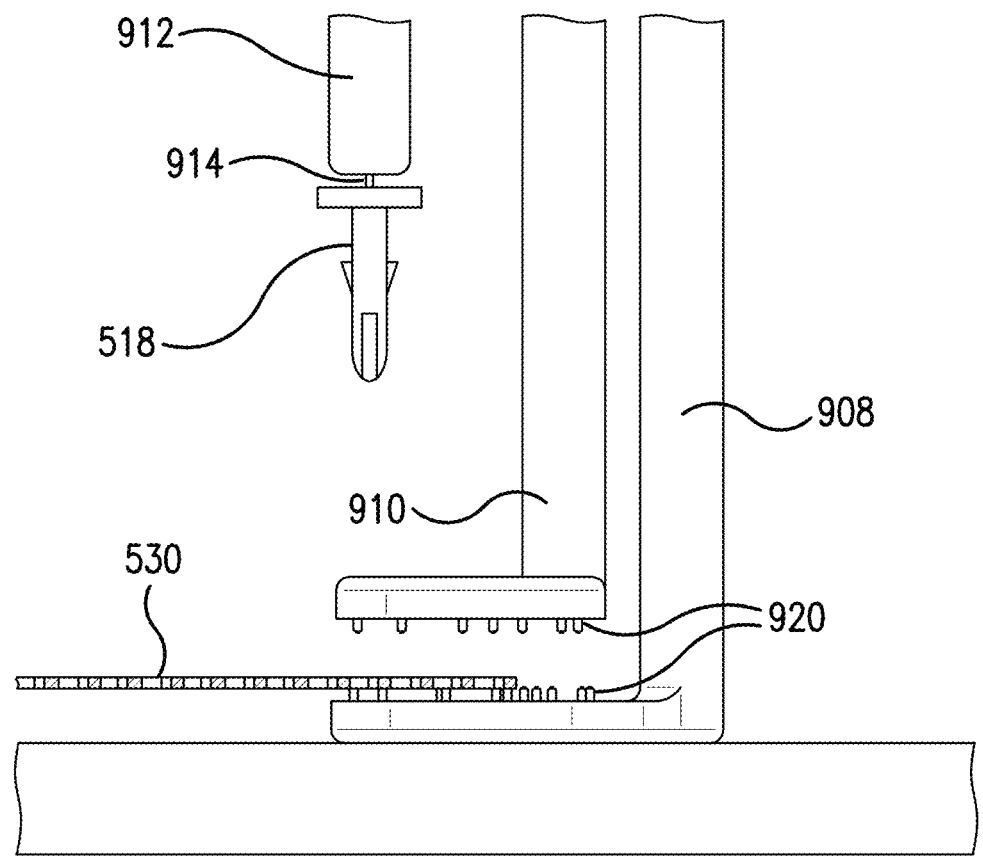
Figure 9I:
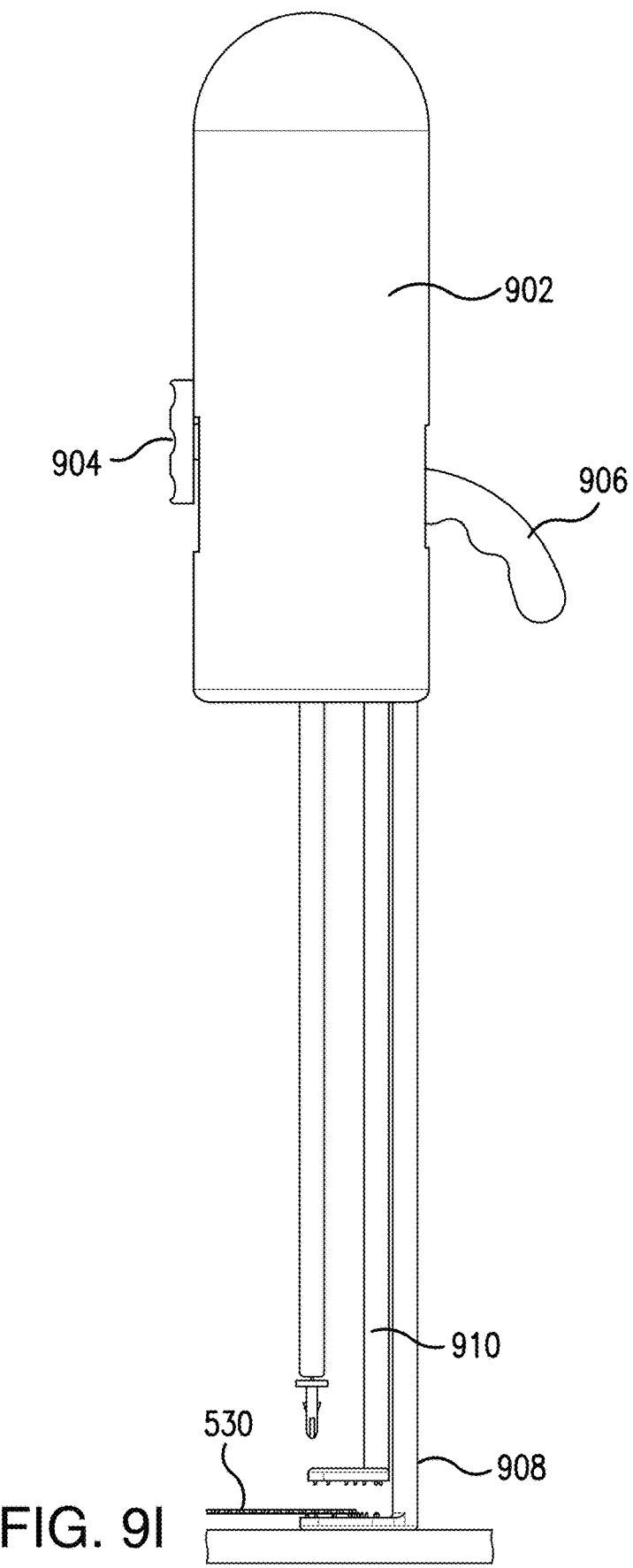

FIG. 9G depicts the exemplary mesh fixation device positioned in proximity to a mesh 530 that covers a sutured incision 528. FIG. 9H depicts a different view of the exemplary mesh fixation device positioned with the adjustable mesh positioning component 908 placed underneath the mesh 530. The mesh 530 can rest upon the spikes 920 atop the adjustable mesh positioning component 908. FIG. 9I depicts a zoomed out view of FIG. 9H. The mesh fixation device can include a handle 902, a triggering mechanism 906, an adjustable mesh positioning component 908, a fixed mesh positioning component 910, and a mesh 530. The handle 902 can provide control of the mesh fixation device. The mesh 530 can be positioned between the adjustable mesh positioning component 908 and the fixed mesh positioning component 910. The triggering mechanism 906 can be engaged to move the adjustable mesh positioning component 908 upwards toward the fixed mesh positioning component 910 and grasp the mesh 530 in the mesh grasping component 918.

Figure 9J:
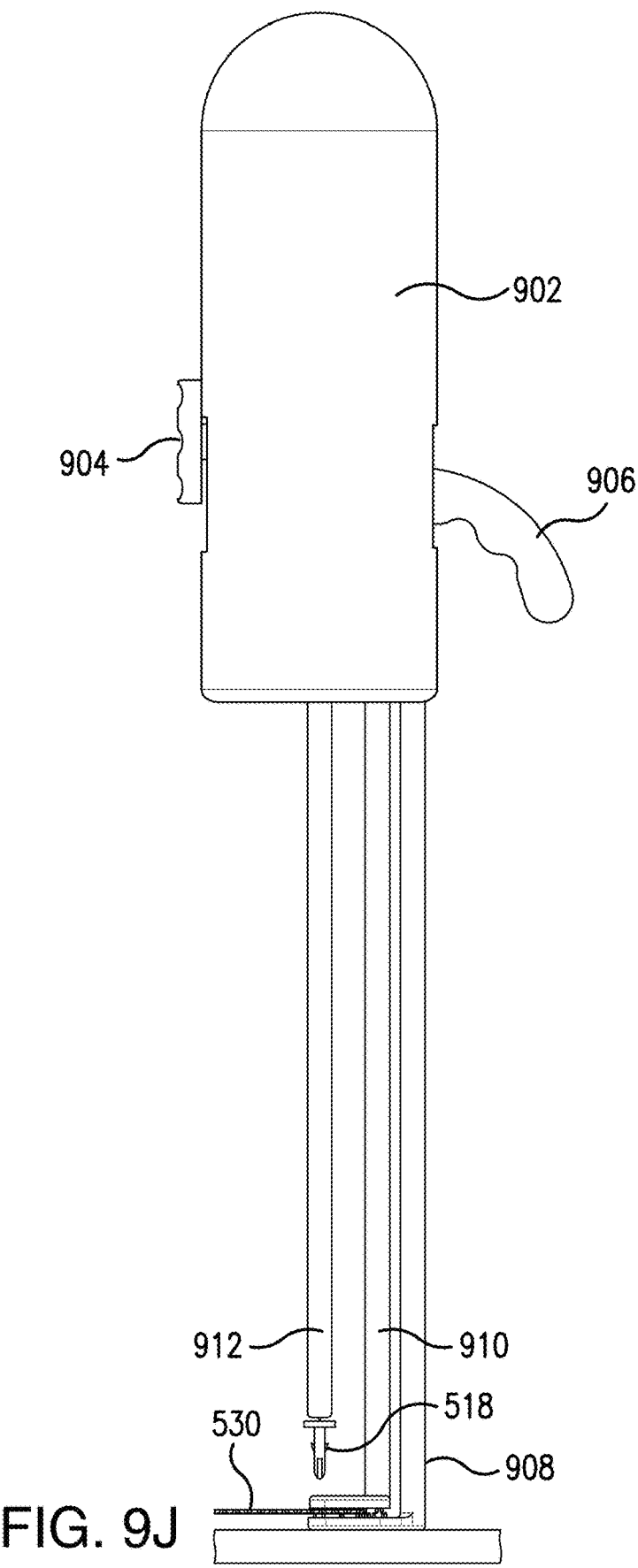
Figure 9K:
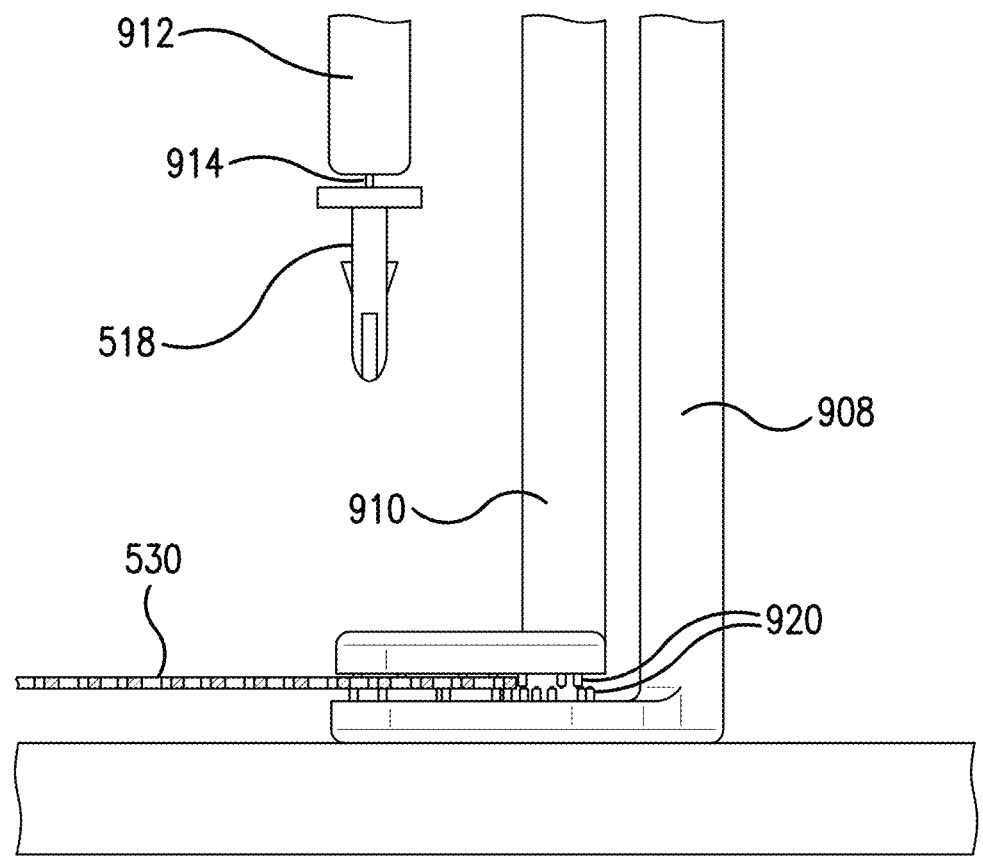

FIG. 9J depicts a view of the exemplary mesh fixation device where the triggering mechanism 906 has been moved upwards. The triggering mechanism 906 can be moved upwards so as to move the adjustable mesh positioning component upwards 908. The adjustable mesh positioning component can be moved upwards toward the fixed mesh positioning component 910 so as to grasp the mesh 530. FIG. 9K depicts a magnified view of the exemplary mesh fixation device in FIG. 9J. The adjustable mesh positioning component can be moved upwards toward the fixed mesh positioning component so as to grasp the mesh 530 with its spikes 920.

Figure 9L:
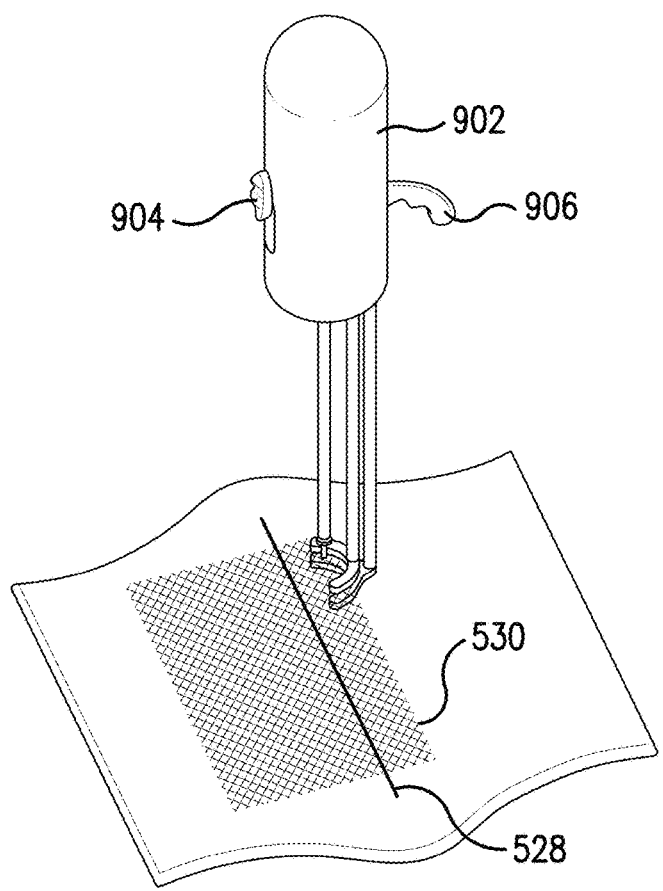
Figure 9M:
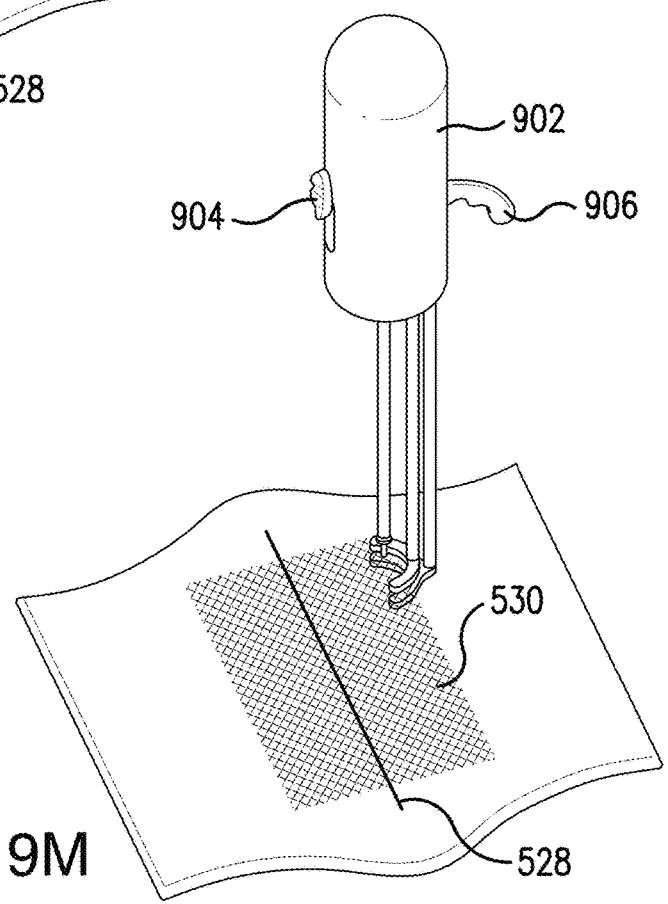

FIGS. 9L and 9M illustrate an exemplary procedure for moving a mesh 530 in relation to a sutured incision 528 using a handle 902 of an exemplary mesh fixation device. FIG. 9L illustrates the handle 902, the sutured incision 528, and the mesh 530, which can be off-center with respect to the sutured incision 528. The handle 902 can be grasped in order to move the mesh fixation device. The mesh 530 can be grasped by the mesh fixation device and moved in relation to the sutured incision 528. FIG. 9M illustrates the handle 902, the sutured decision 528, and the mesh 530, which can be centered with respect to the sutured incision. The handle 902 can be grasped to move the mesh fixation device and the mesh 530, which can be grasped by the mesh fixation device. The mesh fixation device can be pulled in any direction so as to center the 530 with respect to the sutured incision 528. In addition to allowing the user to control the position of the mesh, the adjustable mesh positioning component 908 and the fixed mesh positioning component 910 can allow the user to grasp and create tension in the mesh. Once one side of the mesh is fully affixed onto the fascia, the user can grab, via the adjustable mesh positioning component 908 and the fixed mesh positioning component 910, the mesh on the opposite end and pull the mesh to create tension before affixing it onto the fascia.

Figure 9N:
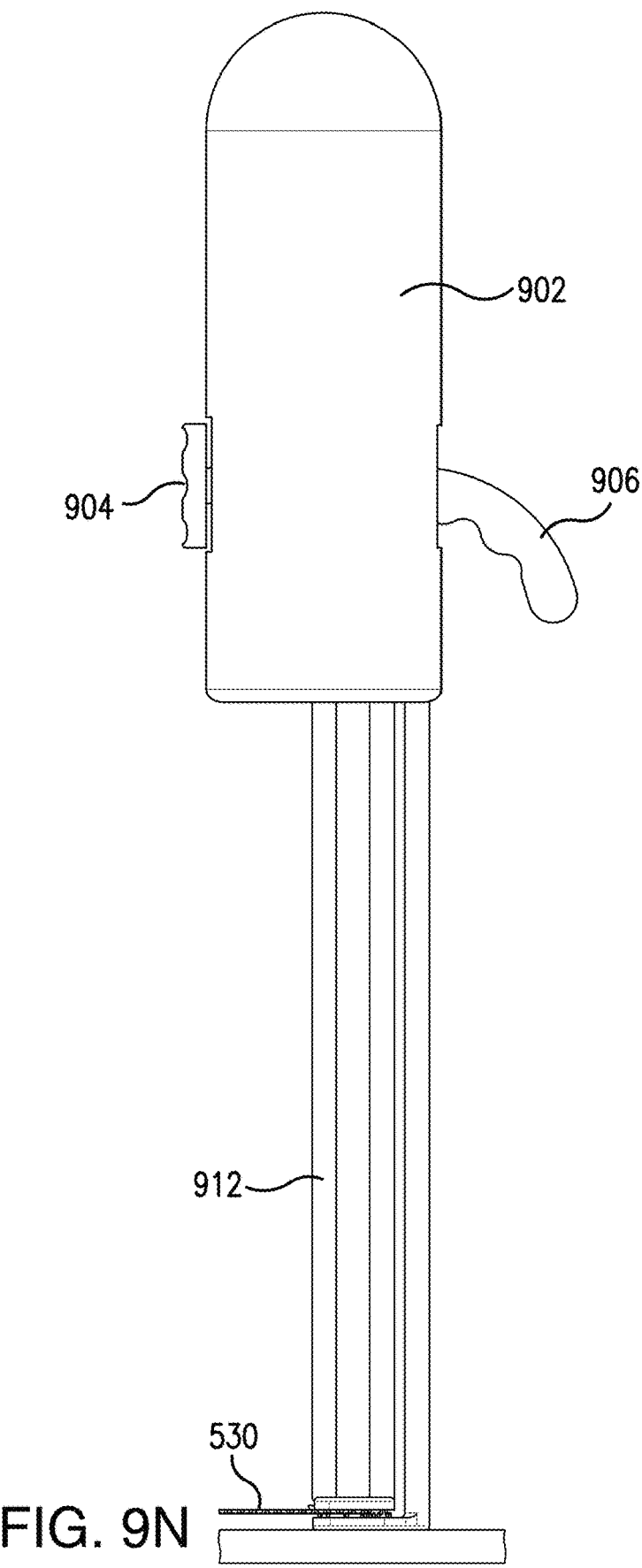
Figure 9O:
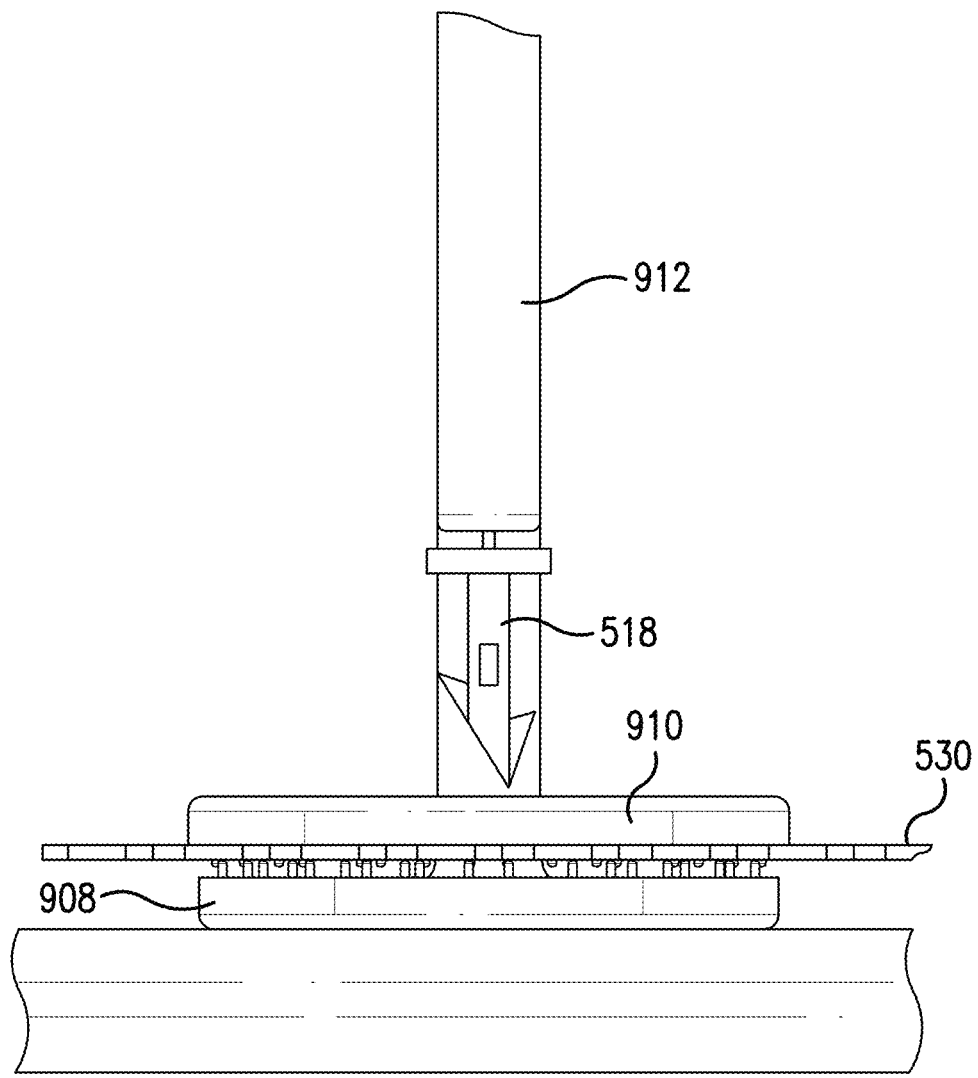
Figure 9P:
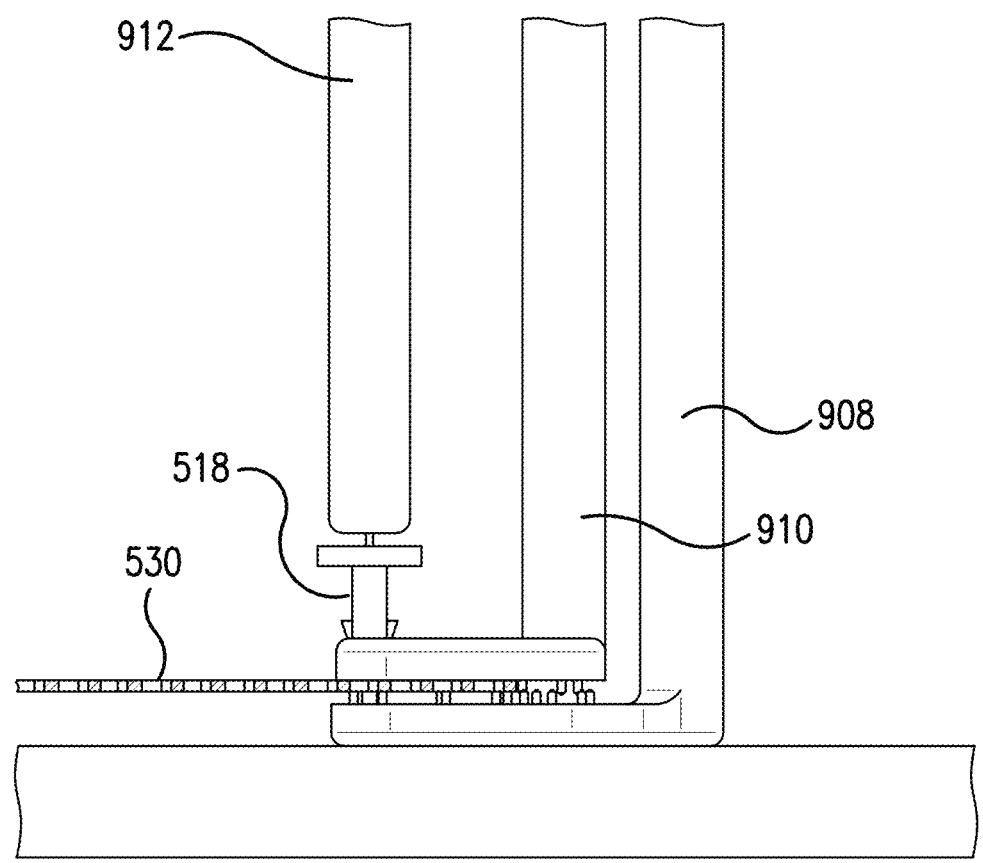
Figure 9Q:
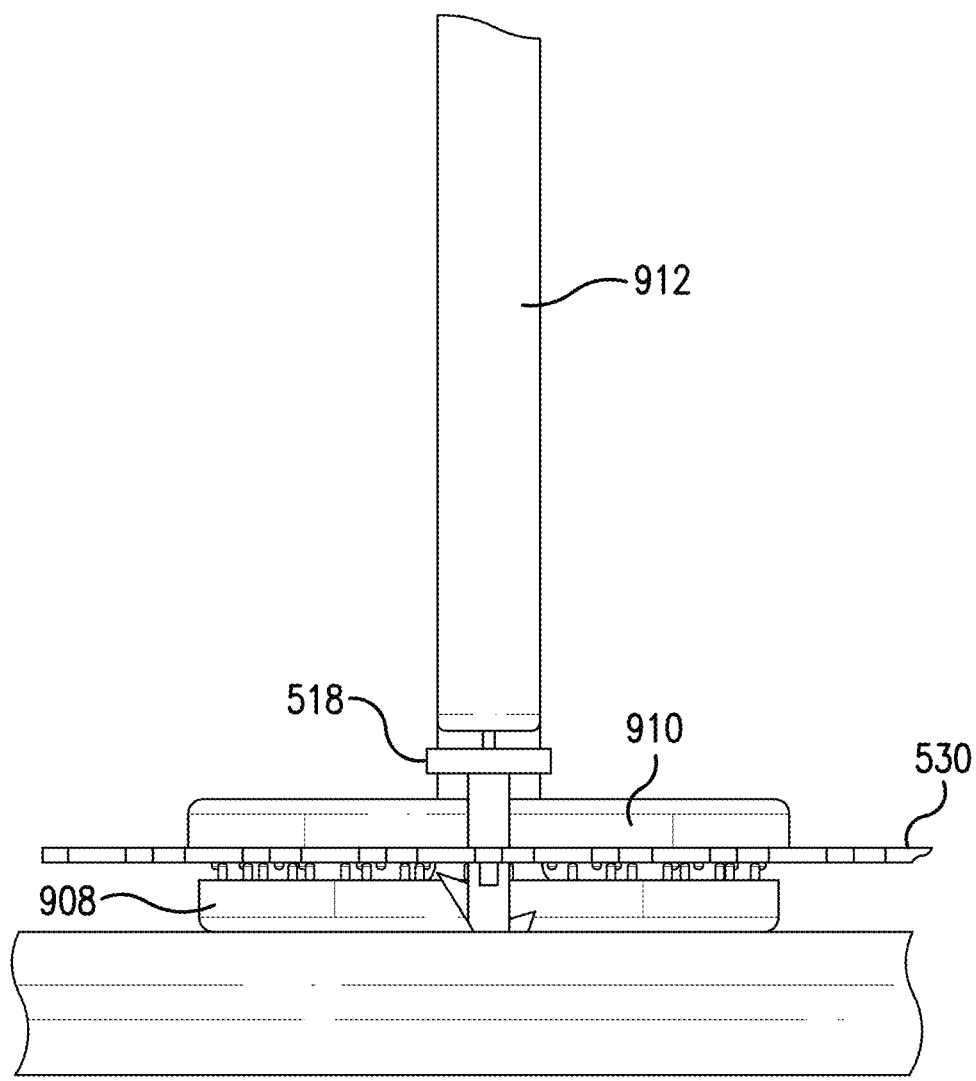
Figure 9R:
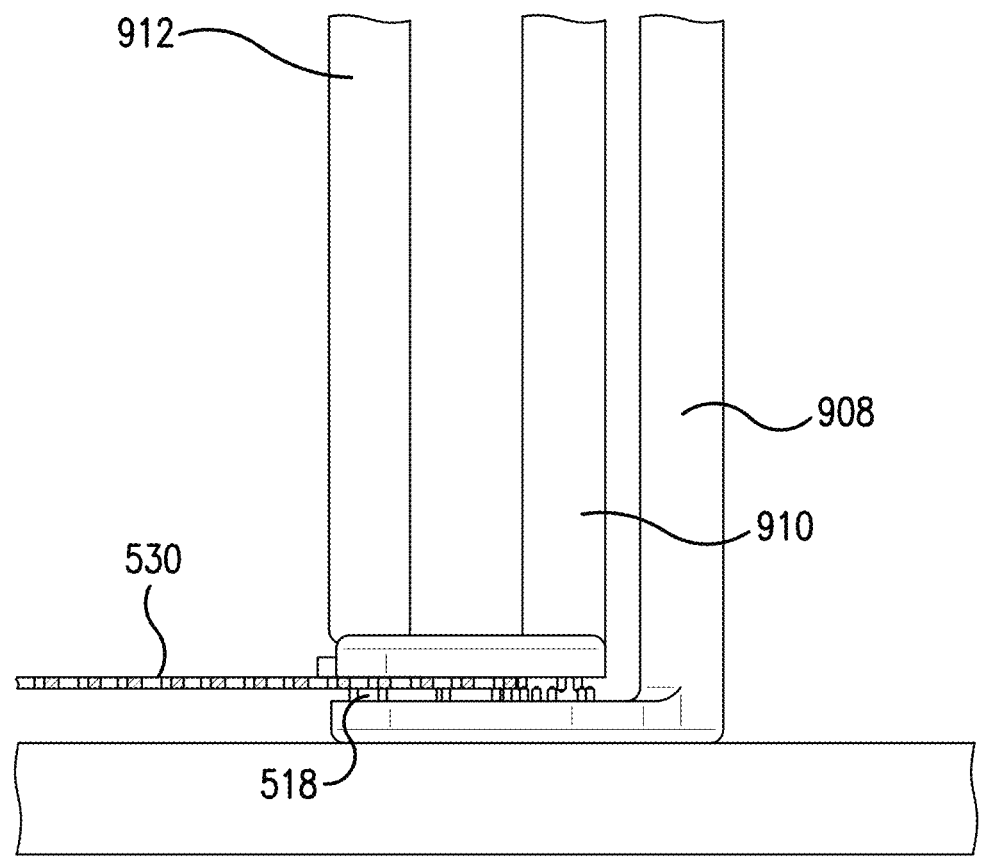
Figure 9S:
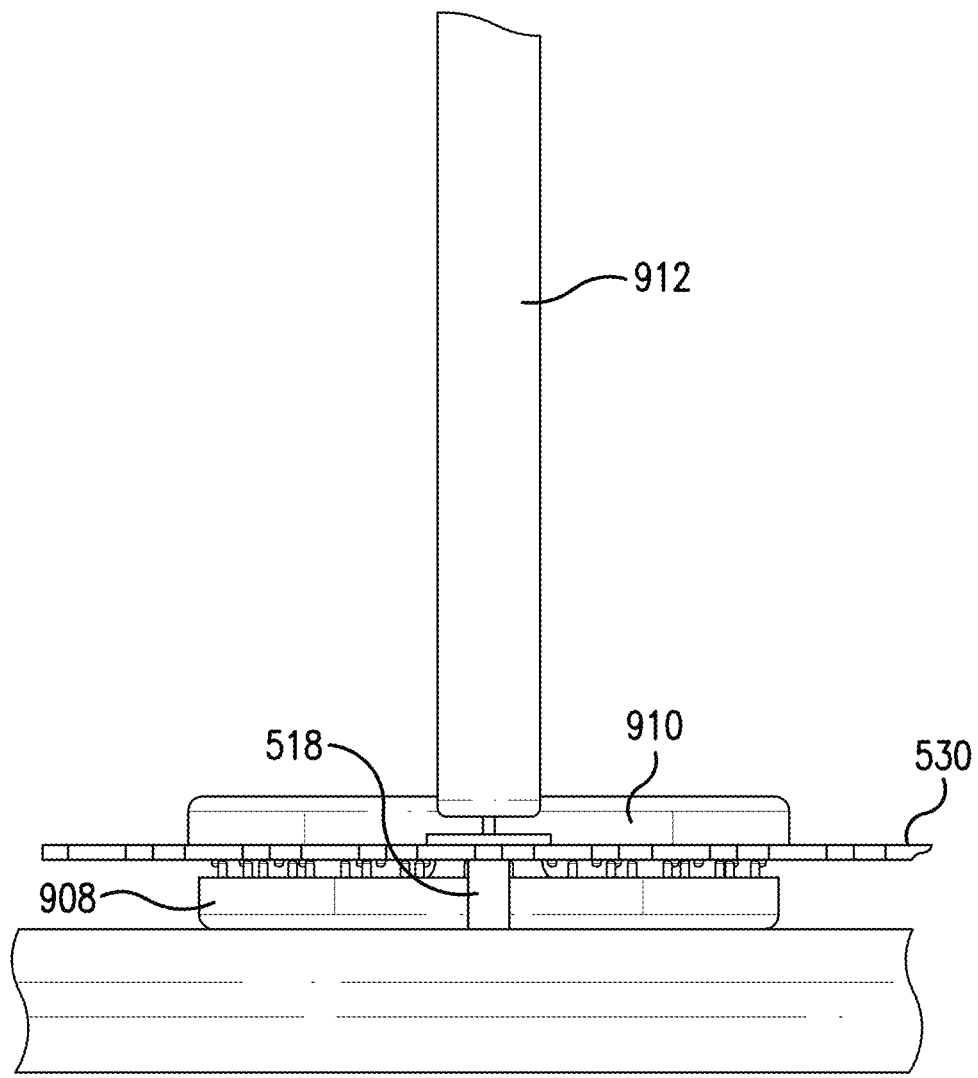

FIGS. 9N-9S illustrate an exemplary procedure for affixing a tack 518 onto a fascia using an exemplary mesh fixation device. FIG. 9N depicts a slider button 904, a tacking component 912, a mesh 530. The slider button 904 can be moved downwards to move the tacking component 912 downwards. The tacking component 912 can be moved downwards to push a tack into the mesh 530 and through the fascia. FIG. 9O depicts a cross-sectional view of the lower portion of the exemplary mesh fixation device. The tacking component can be moved downwards to move the tack 518 through the mesh 530. FIG. 9P depicts a perspective view of the tack 518 being pushed through the mesh 530 using the tacking component 912. FIG. 9Q depicts a cross-sectional view of FIG. 9P with the tack 518 being pushed through the mesh 530 using the tacking component 912. FIG. 9R depicts a perspective view of the tack 518 penetrating the mesh 530 and entering the fascia using the tacking component 912. FIG. 9S depicts a cross-sectional view of FIG. 9R with the tack 518 penetrating the mesh 530 and entering the fascia using the tacking component 912.

Figure 9T:
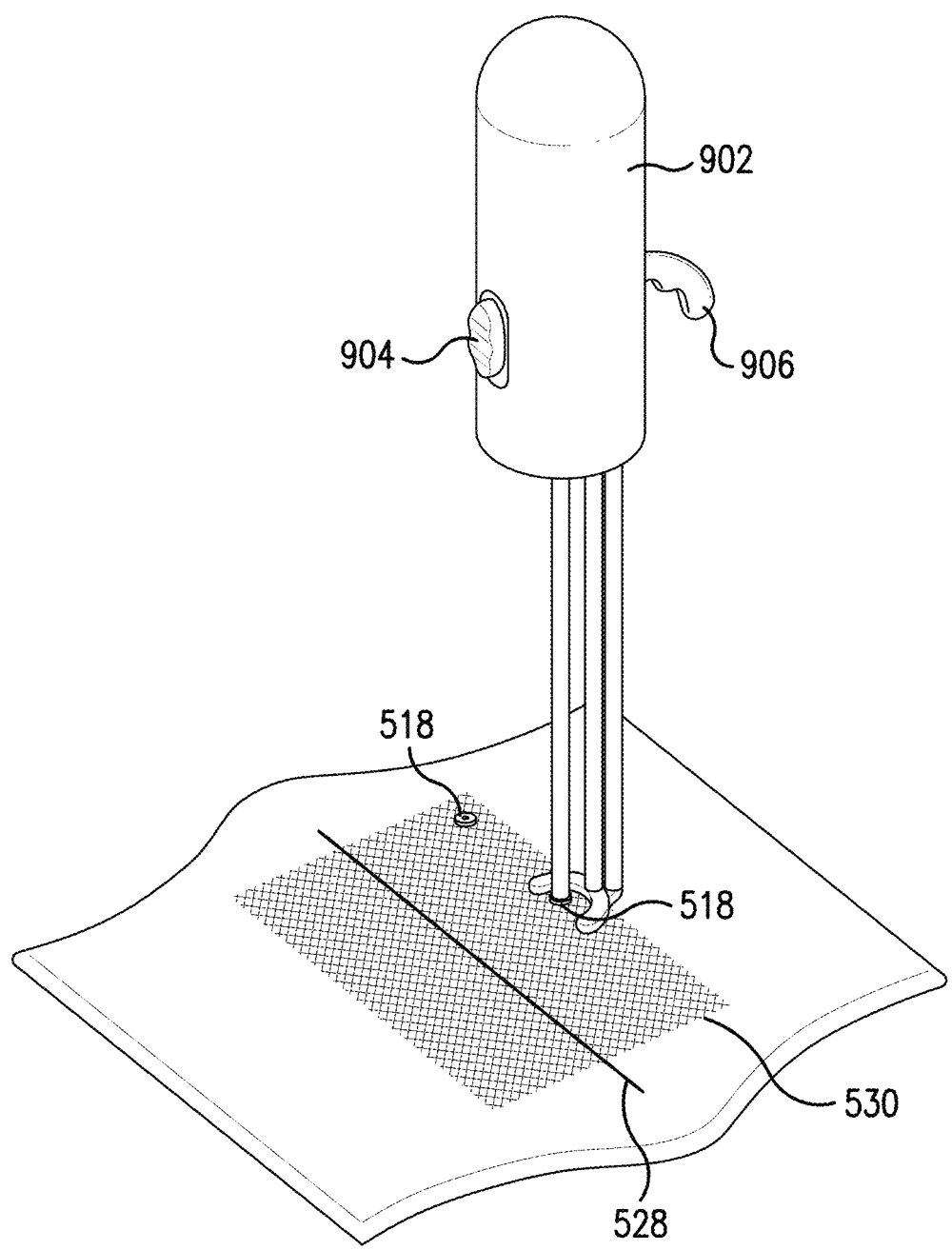

FIG. 9T illustrates an exemplary mesh fixation device repeating the tack affixation process. The mesh fixation device can include a handle 902, a slider button 904, a triggering mechanism 906, tacks 518, a mesh 530, and a sutured incision 528. The exemplary mesh fixation device can be moved to different positions using the handle 902. The triggering mechanism 906 can be used to grasp the mesh 530 and keep the mesh 530 tensioned. The slider button 904 can be used to push the tack 518 downwards through the mesh 530 and into the fascia 528. This process can be repeated by continually moving the mesh fixation device to a different position until the mesh 530 has been fully affixed and tensioned. By allowing the mesh 530 to be grasped and tensioned, the triggering mechanism 906 can allow the mesh 530 to be tensioned in all directions, resulting in improved mesh tensioning.

Figure 10A:
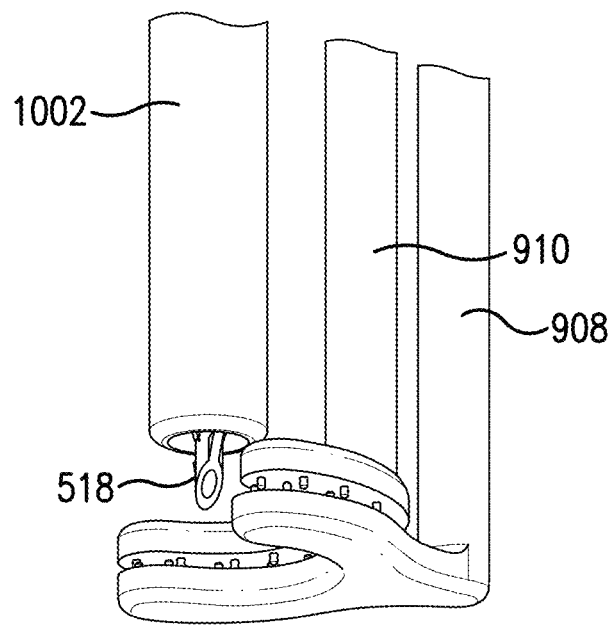
FIGS. 10A and 10B illustrate diagrams of a mesh fixation device having multiple tacks pre-loaded in the tacker in accordance with an exemplary embodiment of the disclosed subject matter.
Figure 10B:
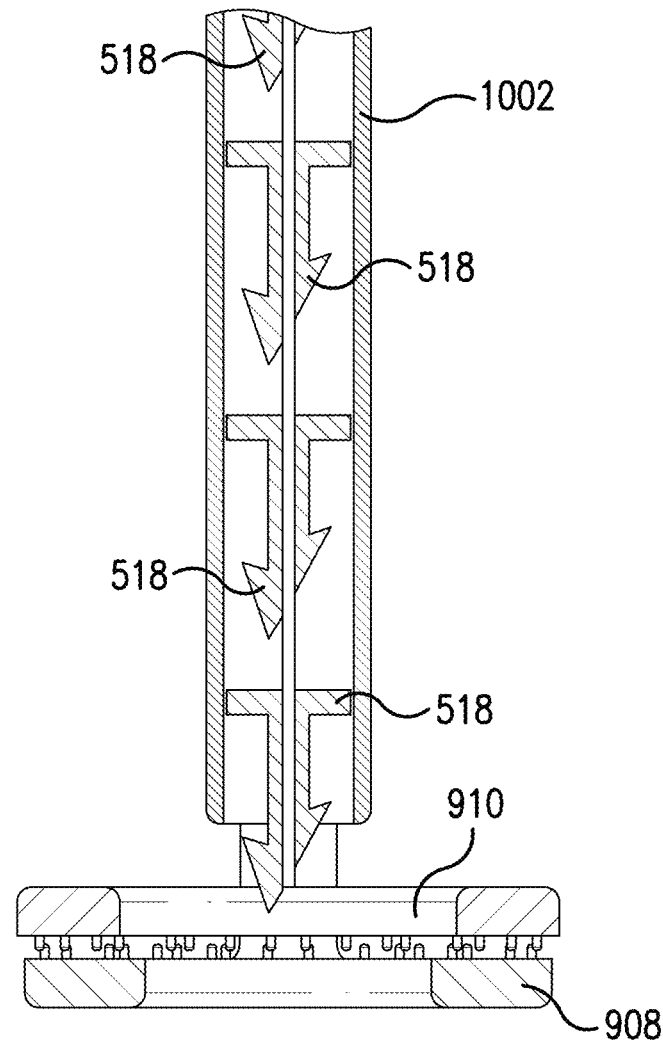

FIGS. 10A and 10B depict an exemplary mesh fixation device with tacks 518 loaded inside the tacker 1002. The exemplary embodiment depicted by FIG. 10A illustrates a tacker 1002, a tack 518, an adjustable mesh positioning component 908, and a fixed mesh positioning component 910. FIG. 10B depicts a cross-sectional view of FIG. 10A with tacks 518 contained in the tacker 1002. The tacks 518 can be contained in the tacker 1002 such that the tack 518 can automatically reload after a tack 518 has been affixed.

Figure 11A:
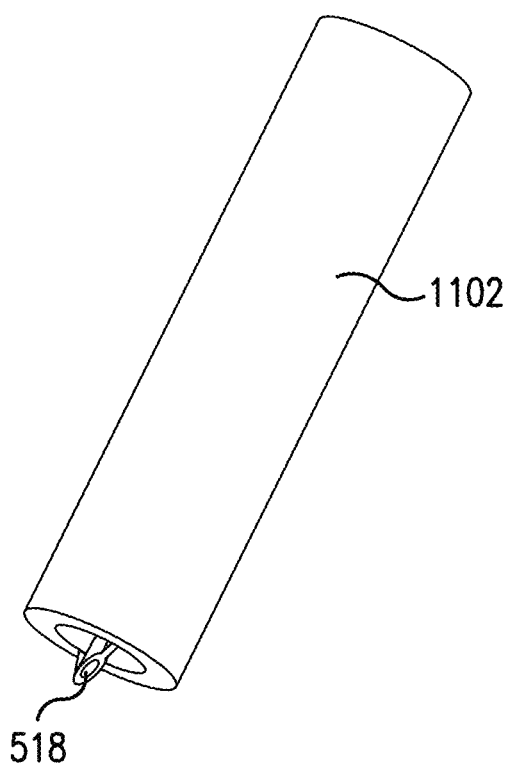
FIGS. 11A-11C illustrate diagrams of a tack cartridge in accordance with an exemplary embodiment of the disclosed subject matter.
Figure 11B:
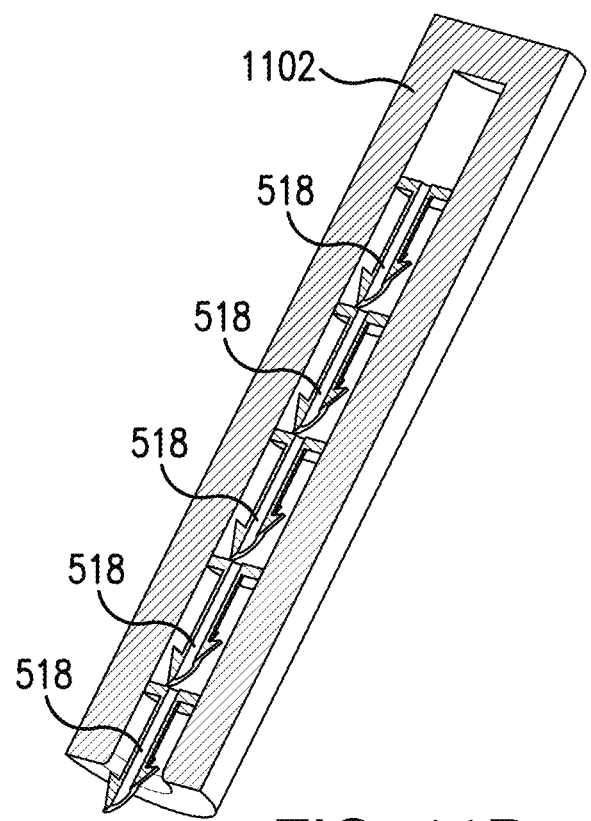
Figure 11C:
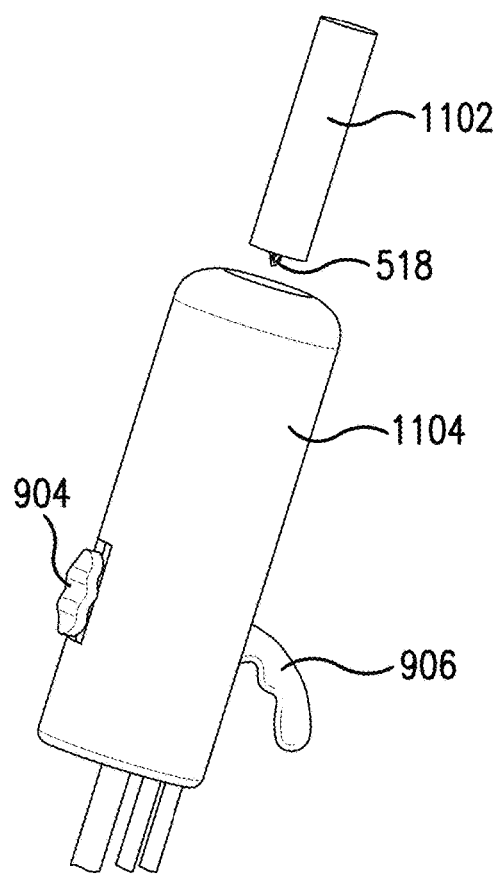

FIGS. 11A-11C depict an exemplary mesh fixation device with tacks 518 loaded in a cartridge 1102. The exemplary embodiment depicted by FIG. 11A illustrates a cartridge 1102 and a tack 518. FIG. 11B depicts a cross-sectional view of FIG. 11A with tacks 518 contained in the cartridge 1102. The tacks 518 in the cartridge 1102 can automatically reload after a tack 518 has been affixed. The exemplary embodiment depicted by FIG. 11C illustrates a tacks 518, a cartridge 1102, and a handle 1104. The cartridge 1102 can contain tacks 518 and can be loaded into the handle 1104 of the mesh fixation device.

Figure 12:
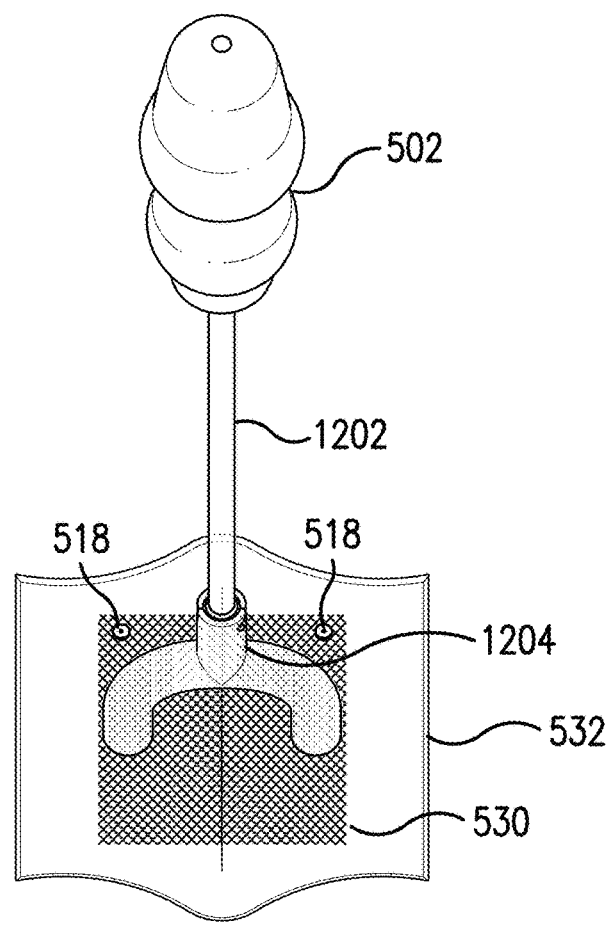
FIG. 12 illustrates a diagram of a mesh fixation device with a spreading mechanism in accordance with an exemplary embodiment of the disclosed subject matter.

FIG. 12 illustrates an exemplary mesh fixation device with a spreading mechanism in accordance with another aspect of the disclosed subject matter. The exemplary embodiment depicted by FIG. 12 illustrates a shaft 1202 and an adapter 1204 containing a spreading mechanism. The shaft 1202 can be pushed down on in order to activate the spreading mechanism. As discussed further herein, the spreading mechanism can be activated to move the arms of the adapter 1204 apart from each other, which can allow the tacks to be affixed at varying distances. As a result of the spreading, the mesh can also become pre-tensioned.

Figure 13A:
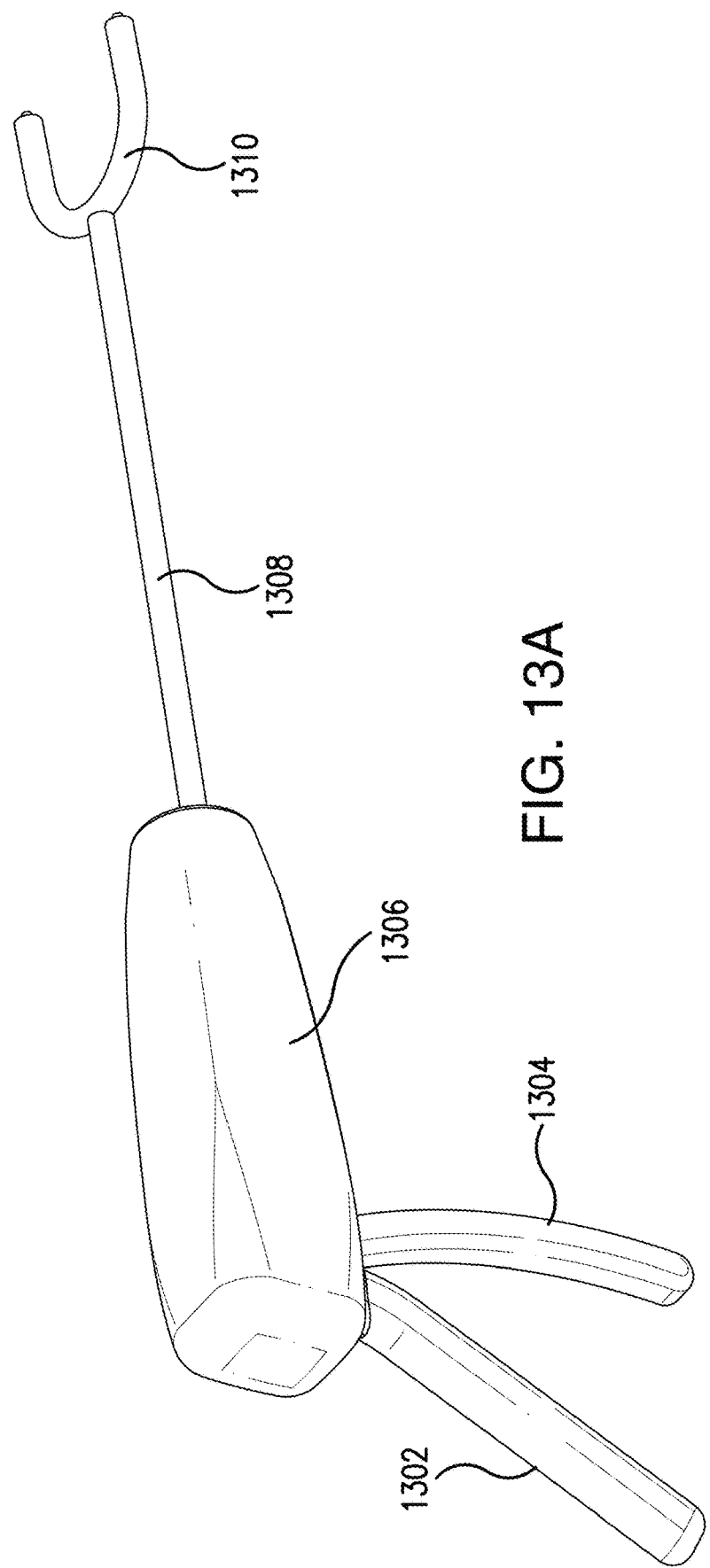
Figure 13B:
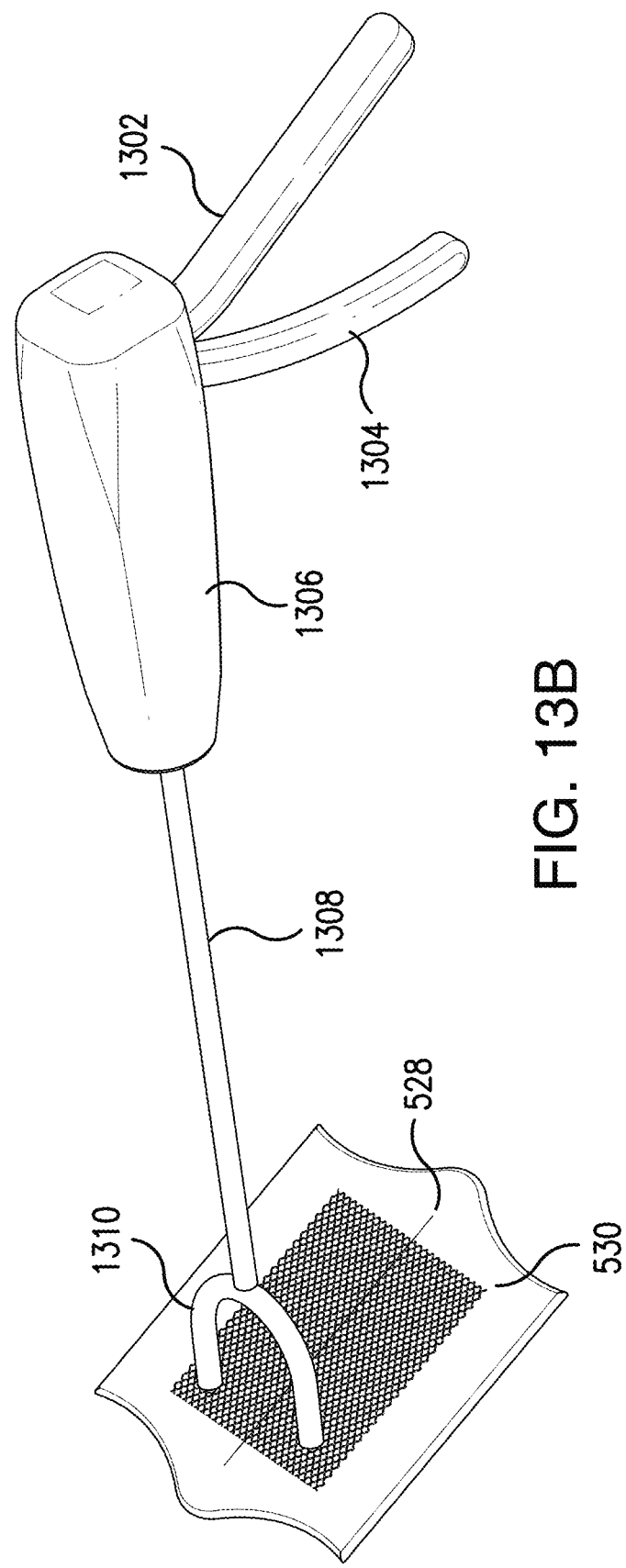

FIGS. 13A-13C illustrate an exemplary tacker gun. The exemplary embodiment depicted by FIG. 13A illustrates a handle 1302, trigger 1304, a housing 1306, a barrel 1308, and a U-shaped adapter 1310. The handle 1302 and housing 1306 can be used to hold the tacker gun. The trigger 1304 can be depressed to fire tacks, which can be housed in the barrel 1308. The tacks can split into both sides of the U-shaped adapter 1310 when the trigger 1304 has been fired. The exemplary embodiment depicted by FIG. 13B illustrates the tacker gun in proximity to a mesh 530 and a fascia. The handle 1302 and housing 1306 can be used to position the tacker gun in proximity to the mesh 530. The tacks can be housed in the barrel 1308. The trigger 1304 can be depressed to split the tack into the U-shaped adapter 1310 and fire them through the mesh 530 at a set distance from each other. FIG. 13C depicts the tacker gun affixing the mesh 530 to the fascia using tacks 518. The tacks 518 can be housed in the barrel 1308 and fired through the U-shaped adapter 1310, which splits the tacks so that the two tacks can be fired simultaneously.

Figure 14A:
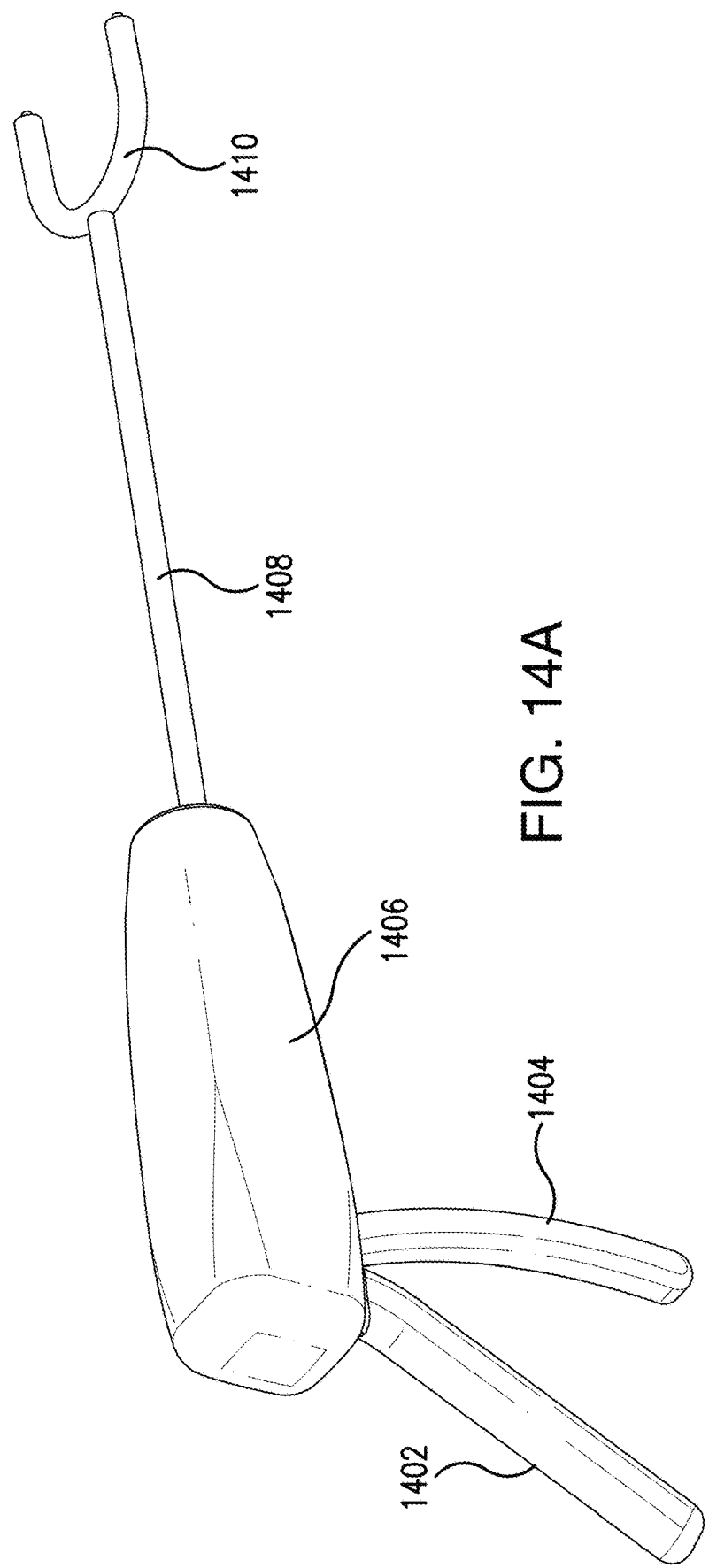
FIGS. 14A-14C illustrate different views of an exemplary tacker gun with tacks pre-loaded in a U-shaped tack adapter of the tacker gun in accordance with an exemplary embodiment of the disclosed subject matter.
Figure 14B:
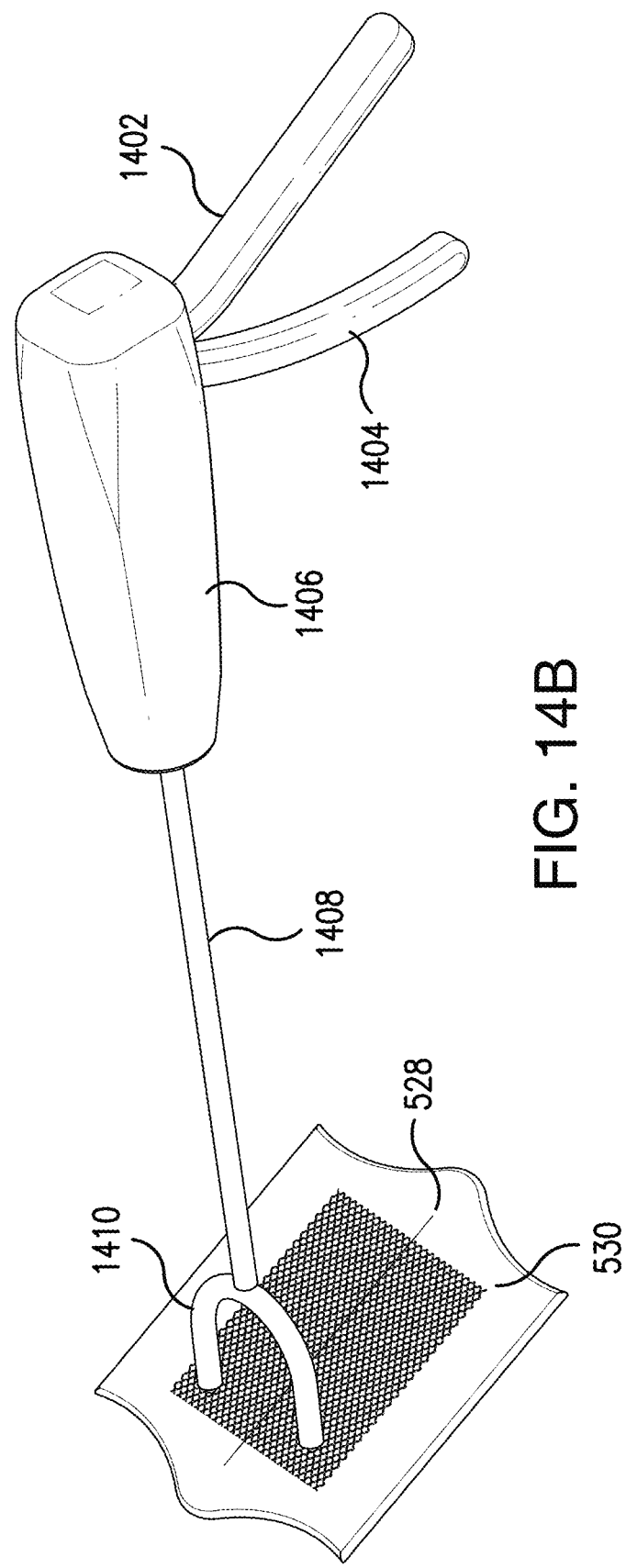
Figure 14C:
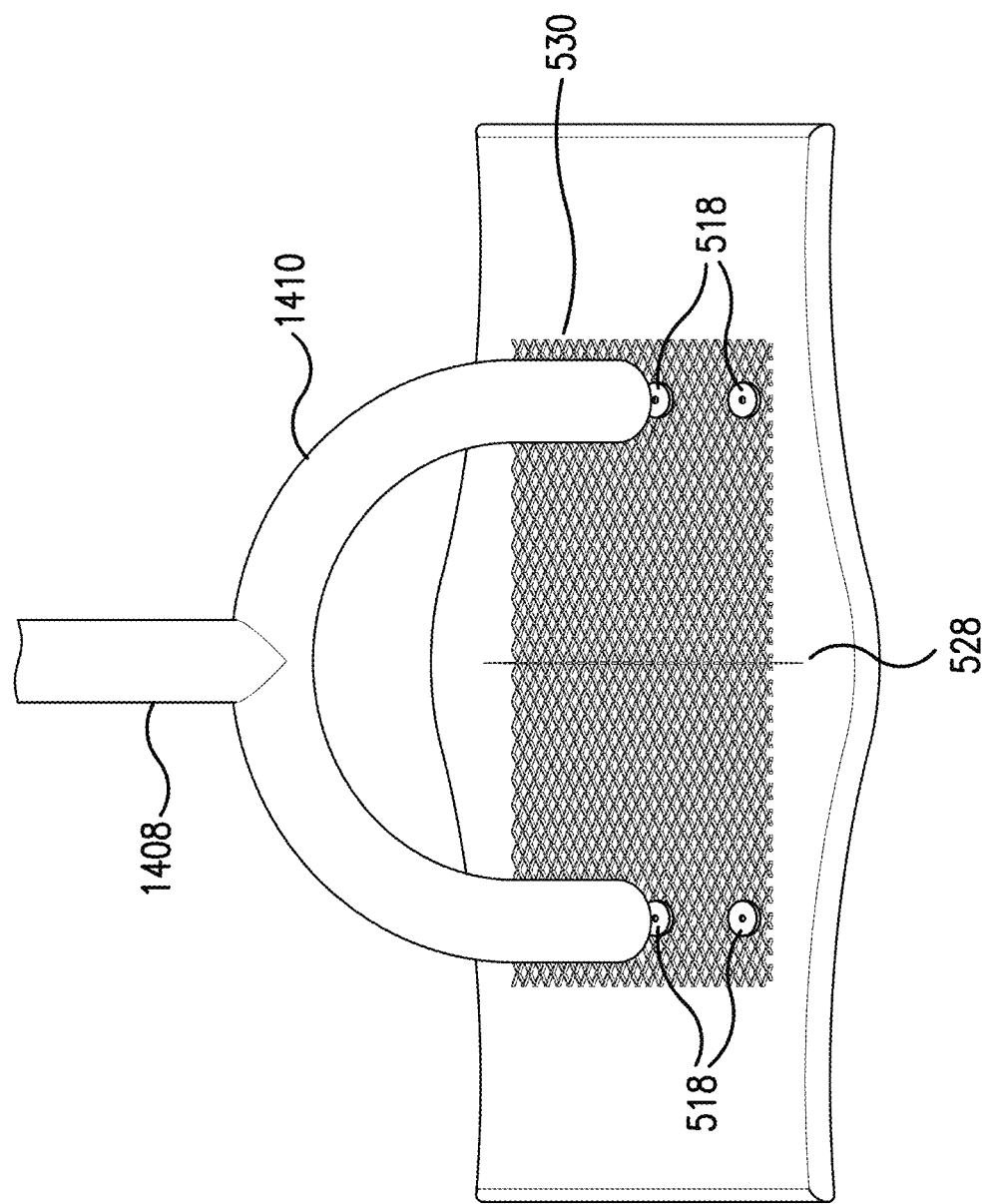

FIGS. 14A-14C illustrate an exemplary tacker gun. The exemplary embodiment depicted by FIG. 14A illustrates a handle 1402, trigger 1404, a housing 1406, a barrel 1408, and a U-shaped adapter 1410. The handle 1402 and housing 1406 can be used to hold the tacker gun. The trigger 1404 can be depressed to fire tacks, which can be housed in the U-shaped adapter 1410. The exemplary embodiment depicted by FIG. 14B illustrates the tacker gun in proximity to a mesh 530 and a fascia. The handle 1402 and housing 1406 can be used to position the tacker gun in proximity to the mesh 530. The tacks can be housed in the U-shaped adapter 1410. The trigger 1404 can be depressed to fire the tacks through the mesh 530 at a set distance from each other. FIG. 14C depicts the tacker gun affixing the mesh 530 to the fascia using tacks 518. The tacks 518 (e.g., tacks 518a and 518b) can be housed in the U-shaped adapter 1410 and fired simultaneously.

Figure 15:
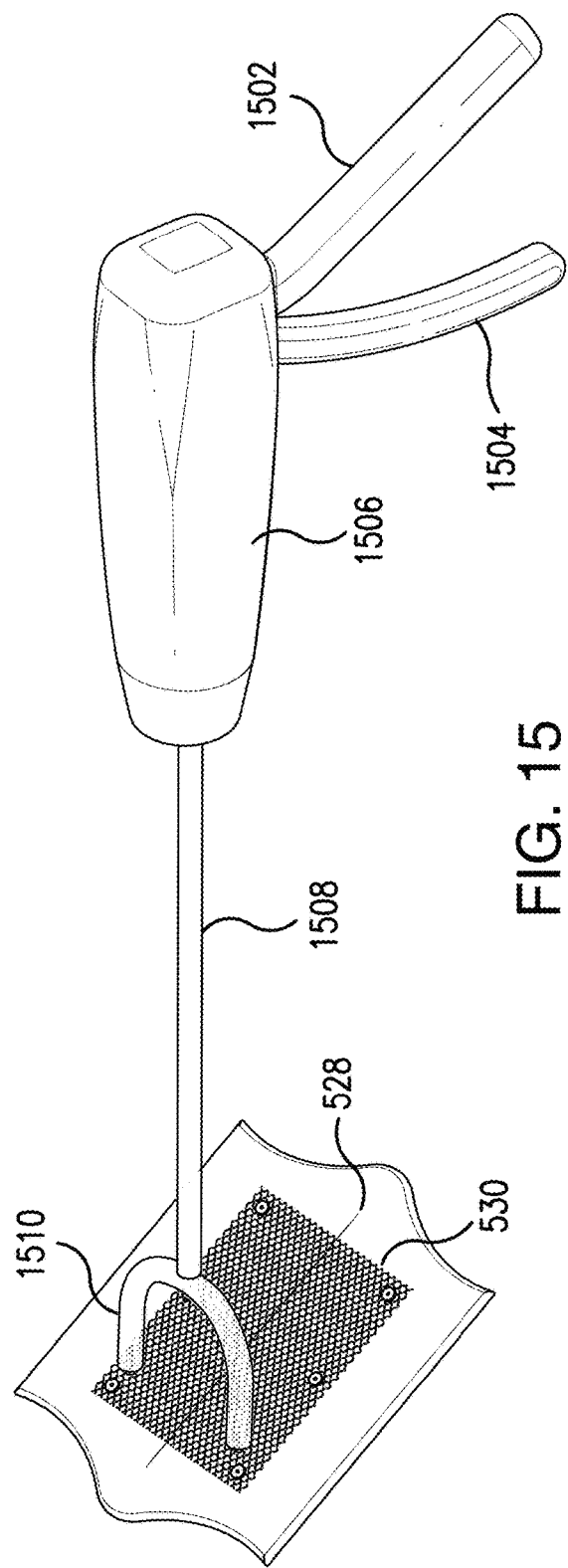
FIG. 15 illustrates a diagram of a tacker gun configured to perform pressure induced spreading in accordance with an exemplary embodiment of the disclosed subject matter.

FIG. 15 illustrates an exemplary tacker gun with a spreading mechanism. The exemplary embodiment depicted by FIG. 15 illustrates a handle 1502, trigger 1504, a housing 1506, a barrel 1508, and a U-shaped adapter 1510. The handle 1502 and housing 1506 can be used to hold the tacker gun. The trigger 1504 can be depressed to fire two tacks at a time, which can be housed in the barrel 1508 or the U-shaped adapter 1510. The distance between the tacks can be adjusted by pushing down on the barrel 1508. Applying pressure to the barrel 1508 can cause the arms of the U-shaped adapter 1510 to spread, adjusting the distance between tacks 518 and tensioning a mesh 530.

Figure 16:
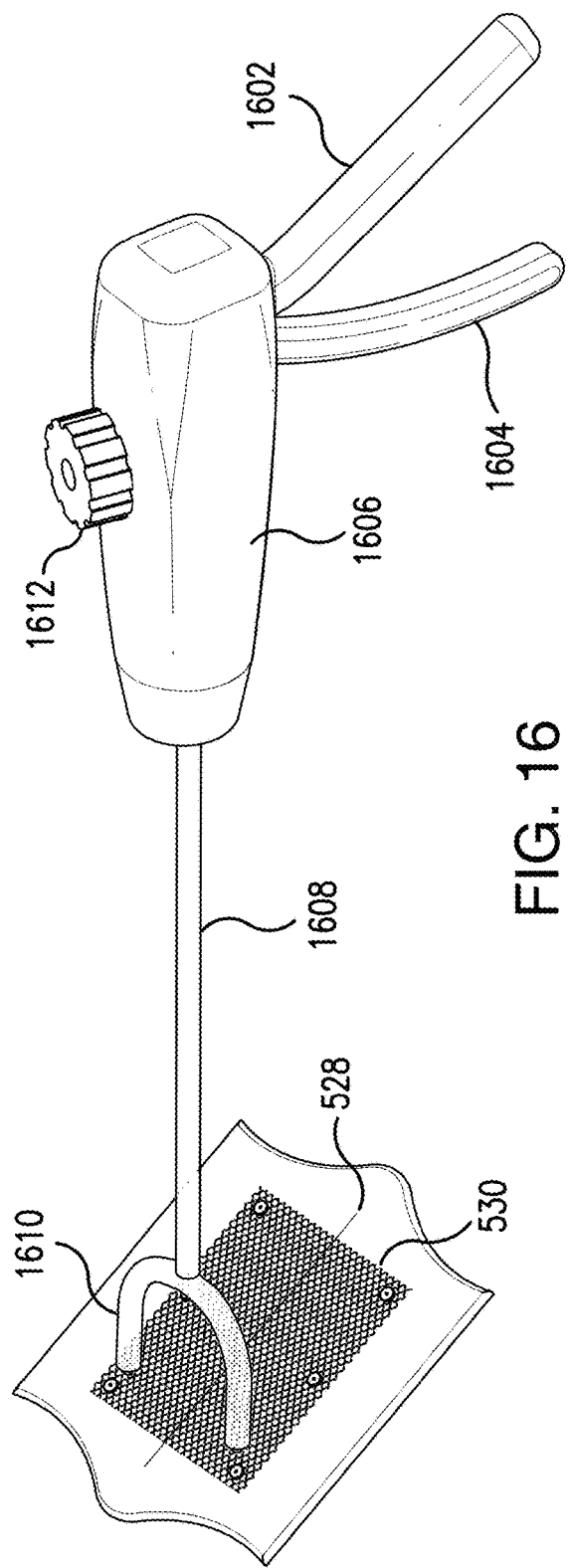
FIG. 16 illustrates a diagram of a tacker gun with a dial that causes the tacker gun's arms to move apart in accordance with an exemplary embodiment of the disclosed subject matter.

FIG. 16 illustrates an exemplary tacker gun with a dial 1612. The exemplary embodiment depicted by FIG. 16 illustrates a handle 1602, trigger 1604, a housing 1606, a barrel 1608, and a U-shaped adapter 1610. The handle 1602 and housing 1606 can be used to hold the tacker gun. The trigger 1604 can be depressed to fire two tacks at a time, which can be housed in the barrel 1608 or the U-shaped adapter 1610. Turning the dial clockwise can cause the arms of the U-shaped adapter 1610 to spread, adjusting the distance between tacks 518 and tensioning a mesh 530. In some embodiments, turning the dial in the counterclockwise direction can decrease the tension, if so desired. The tensioning can be accomplished using a turnbuckle as described below in connection with FIGS. 19A-19D.

Figure 17A:
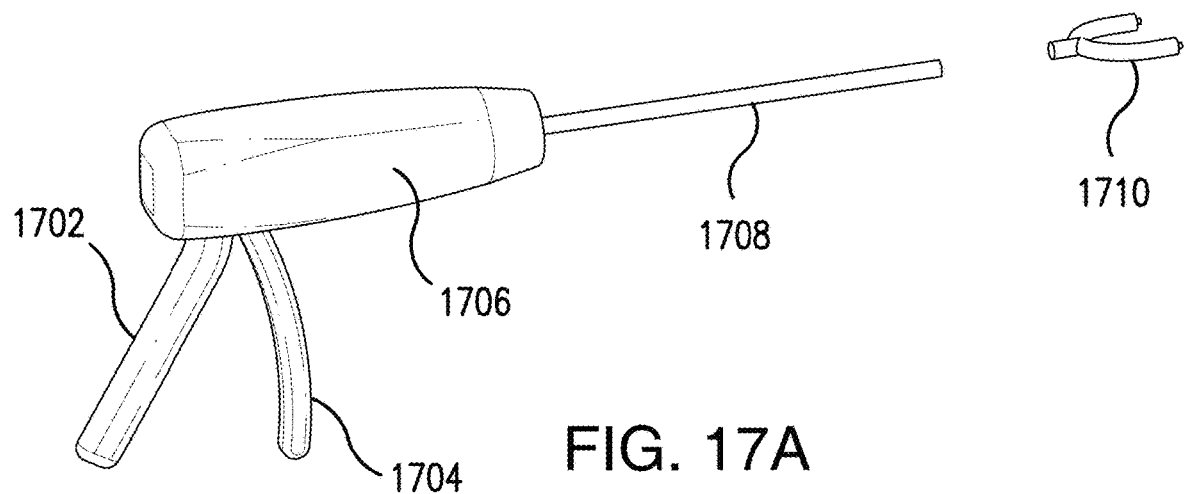
FIGS. 17A and 17B illustrate diagrams of a tacker gun with a detachable U-shaped adapter in accordance with an exemplary embodiment of the disclosed subject matter.
Figure 17B:
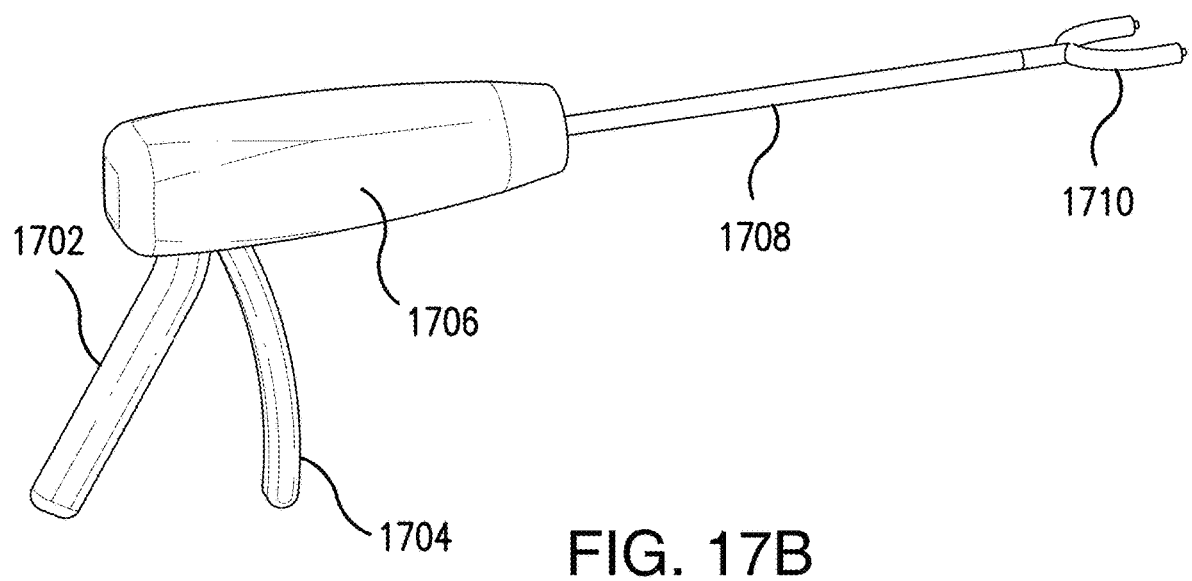

FIGS. 17A and 17B illustrate an exemplary tacker gun with a detachable U-shaped adapter 1710. The exemplary embodiment depicted by FIG. 17A illustrates a handle 1702, trigger 1704, a housing 1706, a barrel 1708, and a U-shaped adapter 1710. The handle 1702 and housing 1706 can be used to hold the tacker gun. The trigger 1704 can be depressed to fire two tacks at a set distance. The tacks can be housed in the U-shaped adapter 1710. The U-shaped adapter can be detached from the tacker gun and can act as a tack-cartridge to reload the tacker gun. FIG. 17B illustrates a different view of FIG. 17A with the U-shaped adapter 1710 attached to the tacker gun.

Figure 18A:
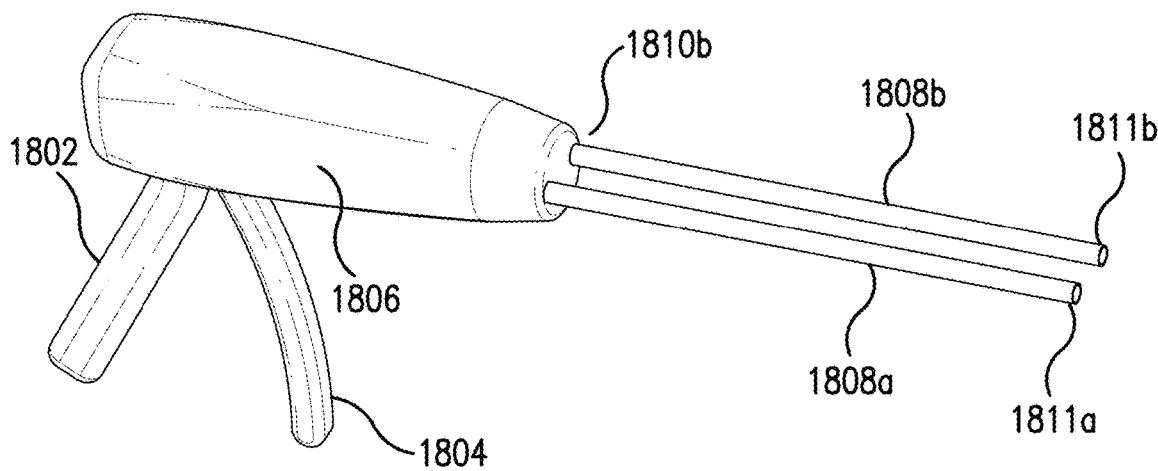
FIG. 18A is a perspective view of a fixation device with first and second arms in accordance with an exemplary embodiment of the disclosed subject matter.

FIG. 18A illustrates an exemplary device for affixing reinforcing material including first and second arms in accordance with the disclosed subject matter. The exemplary embodiment depicted by FIG. 18 illustrates a handle 1802, trigger 1804, a housing 1806, and first and second arms 1808a and 1808b, respectively. In accordance with the disclosed subject matter, the first and second arms 1808a and 1808b each have a proximal end 1810a and 1810b, and a distal end 1811a and 1811b, respectively. The distal ends 1811a and 1811b extend away from the handle 1802, with a length defined between the proximal and distal ends of each arm. The distal end 1811a of the first arm is spaced from the distal end 1811b of the second arm such that the first arm 1808a and the second arm 1808b are engageable with a reinforcing material on opposing sides of a fascial incision. As discussed further herein, one or more fixation elements can be deployed from the distal ends of the first and second arms to affix the reinforcing material on opposing sides of the fascial incision. As embodied herein, the fixation elements can include a plurality of tacks configured to penetrate the reinforcing material and fascia to affix reinforcing material on opposing sides of the fascial incision. Additionally, or alternatively, and as discussed further herein, the fixation elements can include materials with adhesive properties.

As embodied herein, the first and second arms 1808a and 1808b can each define a barrel. As further discussed herein, a plurality of tacks can be stored in the barrel of each of the first arm 1808a and second arm 1808b. The handle 1802 and housing 1806 can be used to hold the tacker gun. In accordance with one aspect of the disclosed subject matter, the first arm 1808a and second arm 1808b can engage with reinforcing material on opposing sides of a fascial incision simultaneously. Alternatively, and as discussed further herein, one arm can be retracted or rotated such that a single arm engages the fascia. In accordance with one aspect of the disclosed subject matter, and as discussed further herein, trigger 1804 can be depressed to fire two tacks simultaneously at a set distance from each other. The tacks can be housed inside the barrel of the first and second arms prior to deployment.

Figure 18B:
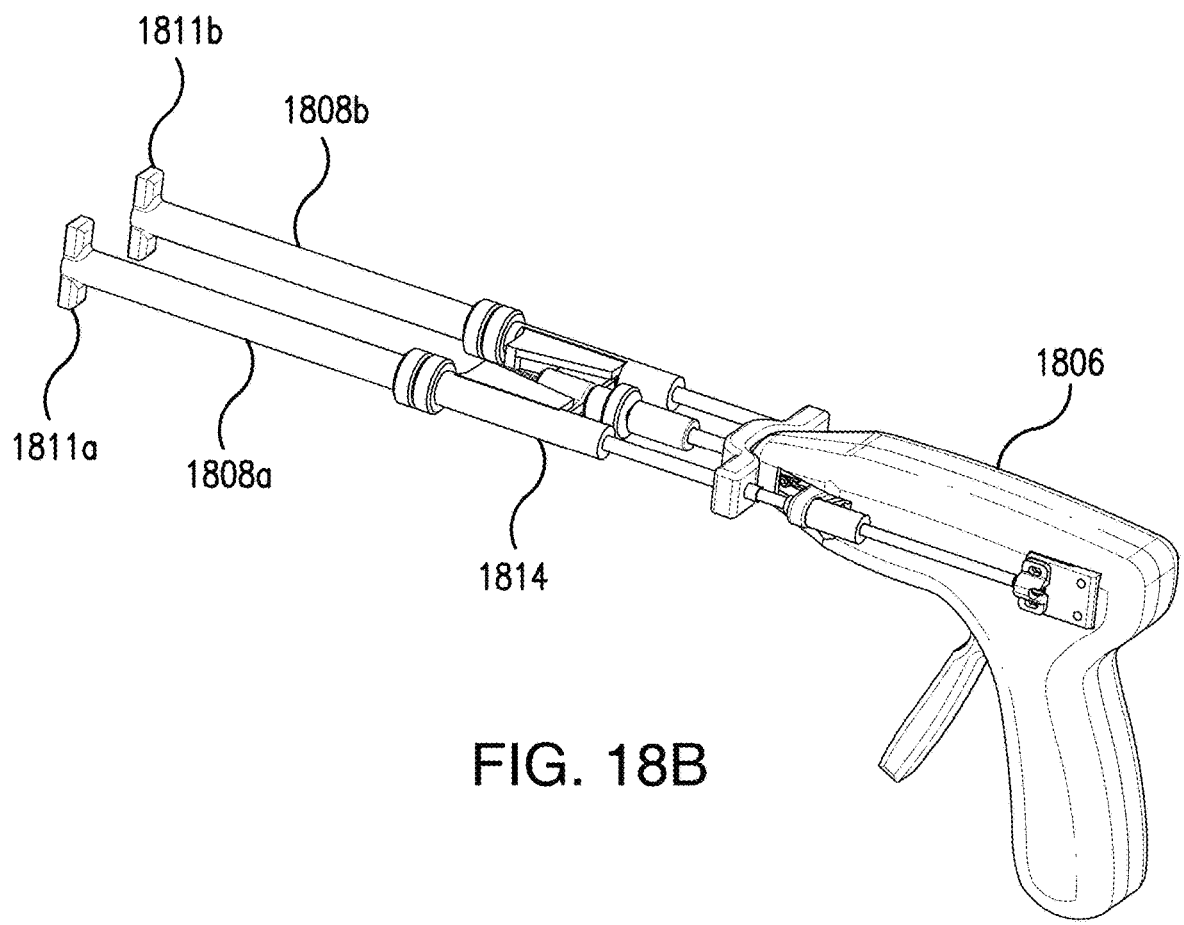
FIG. 18B is a perspective view of a fixation device with first and second arms and a spreading mechanism in accordance with an exemplary embodiment of the disclosed subject matter.
Figure 18C:
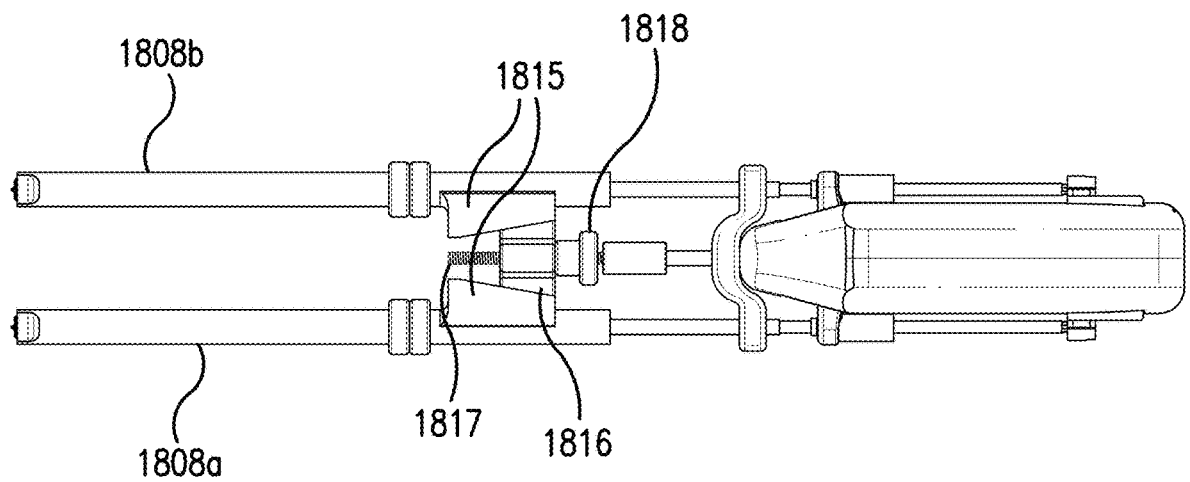
FIG. 18C is a top view of the fixation device of FIG. 18B.
Figure 18D:
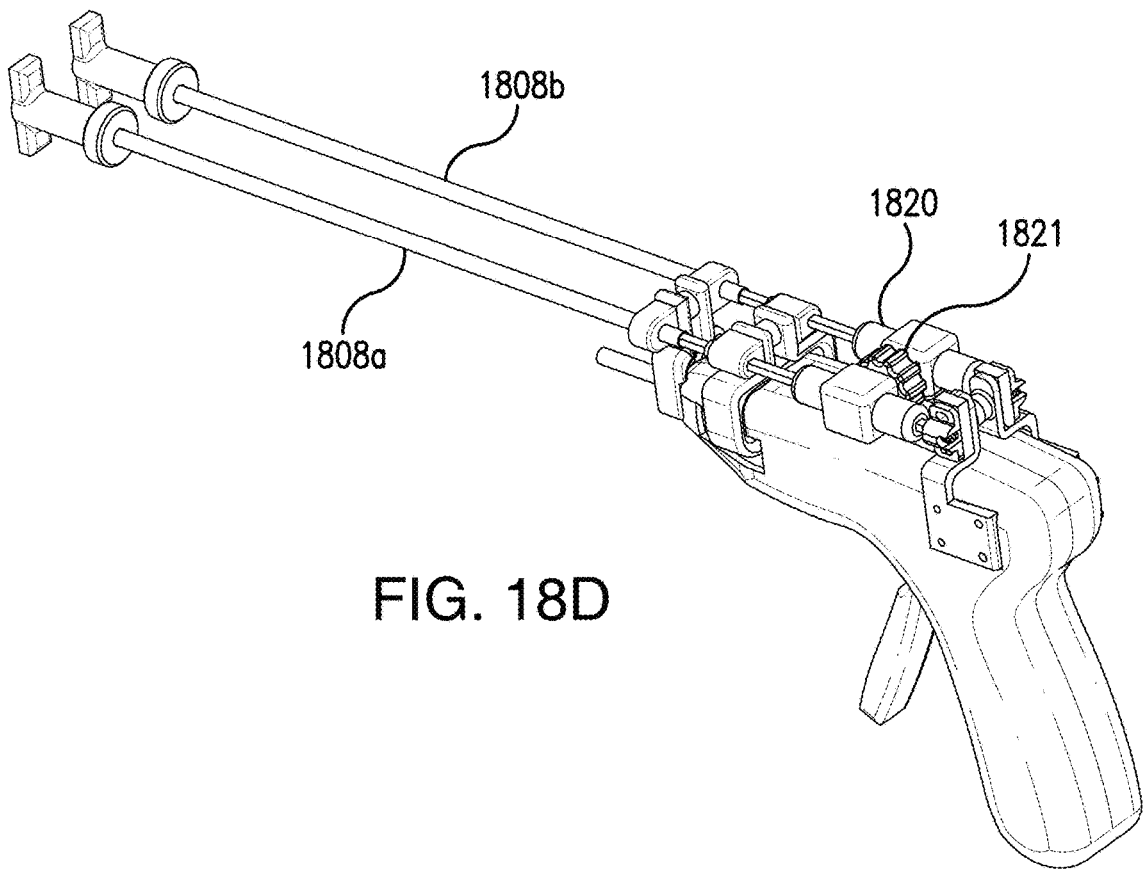
FIG. 18D is a perspective view of a fixation device with first and second arms and a spreading mechanism in accordance with an exemplary embodiment of the disclosed subject matter.
Figure 18E:
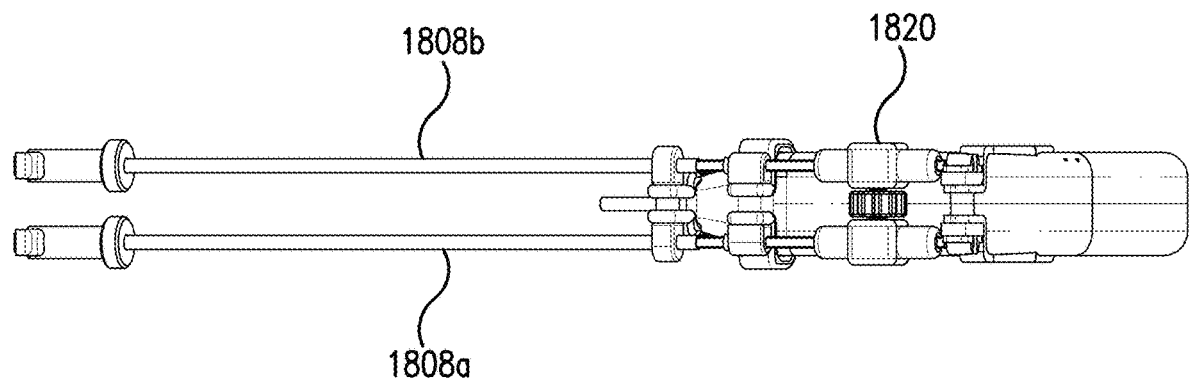
FIG. 18E is a top view of the fixation device of FIG. 18D.
Figure 18F:
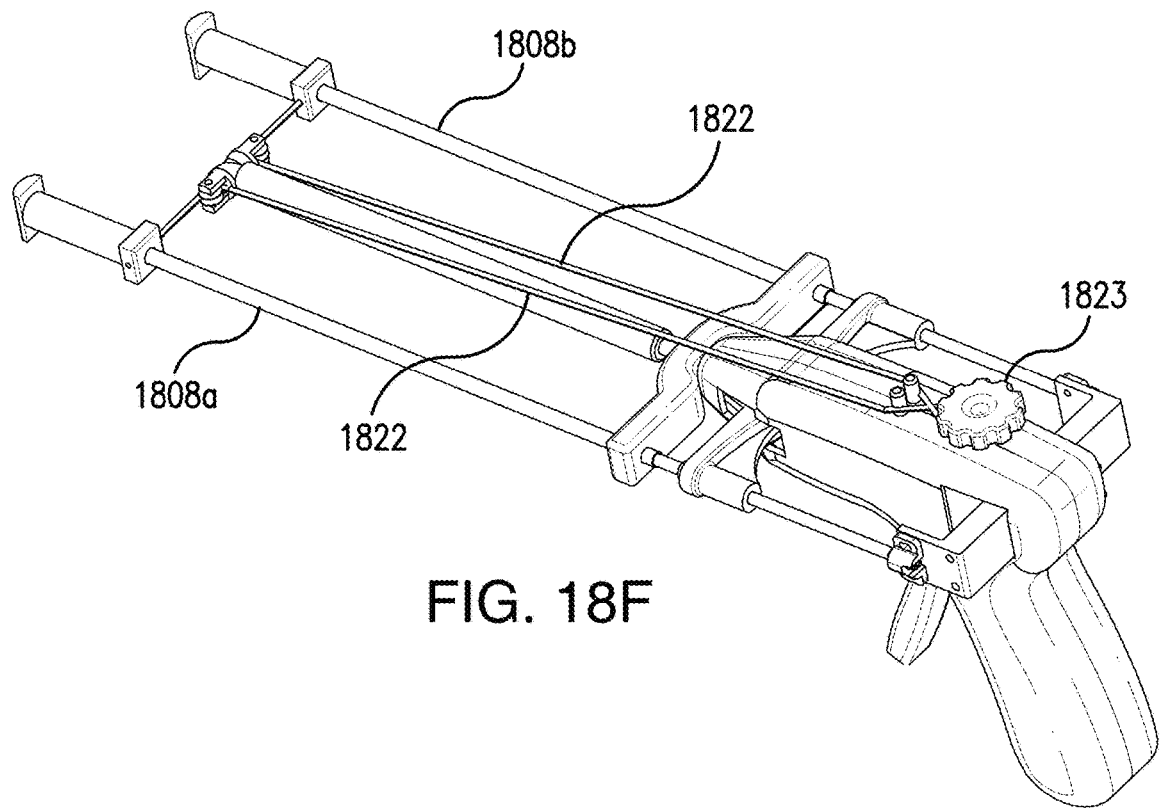
FIG. 18F is a perspective view of a fixation device with first and second arms and a spreading mechanism in accordance with an exemplary embodiment of the disclosed subject matter.

In accordance with another aspect of the disclosed subject matter, and as depicted in FIG. 18B, the distal ends of the first and second arms 1808a and 1808b can releasably couple with reinforcing material upon engagement of the first and second arms with the reinforcing material during onlay reinforcement. By releasably coupling with the reinforcing material, the distal ends can translate separation of the arms 1808a and 1808b into uniform mesh tension, as further discussed herein. For purpose of example, and not limitation, the distal ends of the first and second arms can include hook and loop or Velcro like material to releasably couple with the reinforcing material. Additionally, or alternatively, the distal ends 1811a and 1811b can include ridges that can releasably couple with the reinforcing material. The releasable coupling can be selected such that the distal ends 1811a and 1811b are able to apply at least 1 lbf of lateral tension to the reinforcing material. Additionally, the releasable coupling can be selected such that the distal ends 1811a and 1811b can be decoupled from the reinforcing material without disrupting mesh affixation after fixation elements have been deployed to affix the reinforcing material to the fascia.

As discussed above, affixation devices in accordance with the disclosed subject matter can include a spreading mechanism which can vary the distance between the first arm 1808a and the second arm 1808b. In accordance with one aspect of the disclosed subject matter, and with reference to FIGS. 18B and 18C, a spreading mechanism 1814 can be mounted to the first arm 1808a and the second arm 1808b. For purpose of example, and not limitation, the spreading mechanism can include a first wedge 1815 defined between first arm 1808a and second arm 1808b, and a second wedge 1816 extending from a distal end of the housing between first arm 1808a and second arm 1808b. The second wedge 1816 can be mounted on a threaded shaft 1817, which can include a threaded handle 1818. As handle 1818 is turned, the second wedge 1816 can move relative to the first wedge 1815 to control the distance between the distal ends of the first arm 1808a and the second arm 1808b.

While the spreading mechanism is described above with reference to first and second wedges, alternative spreading mechanisms are envisioned within the scope of the disclosed subject matter. For example, and as depicted in the exemplary embodiment of FIGS. 18D and 18E, the spreading mechanism can include a turnbuckle 1820 mounted between the arms 1808*a* and 1808*b* proximate the housing. Turning the dial 1821 of the turnbuckle 1820 can control the distance between the distal ends of arms 1808*a* and 1808*b*. Additionally, or alternatively, and in accordance with another aspect of the disclosed subject matter, the spreading mechanism can include a pulley. For purpose of example, and not limitation, and with reference to FIG. 18F, one or more cables 1822 can be connected to the distal ends of arms 1808*a* and 1808*b*, and a pully 1823 can be used to adjust the tension on the one or more cables 1822 to control the distance between arms 1808*a* and 1808*b*.

Figure 18G:
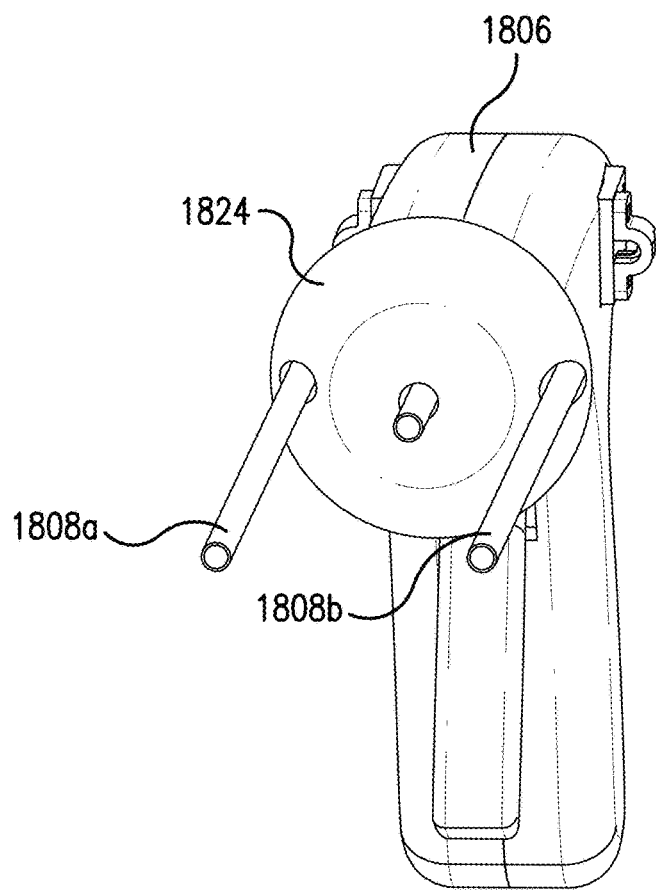
FIG. 18G is a front perspective view of a fixation device with first and second arms in first rotational position in accordance with an exemplary embodiment of the disclosed subject matter.
Figure 18H:
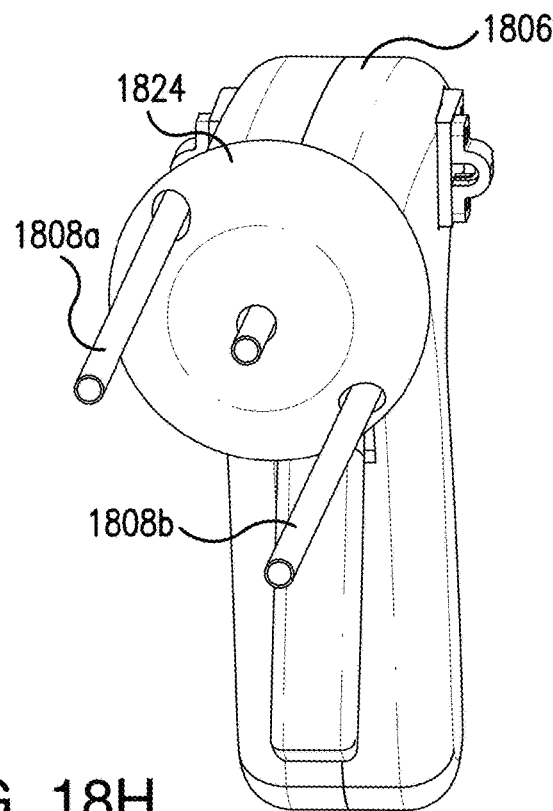
FIG. 18H is a front perspective view of the fixation device of FIG. 18G in a second rotational position.
Figure 18I:
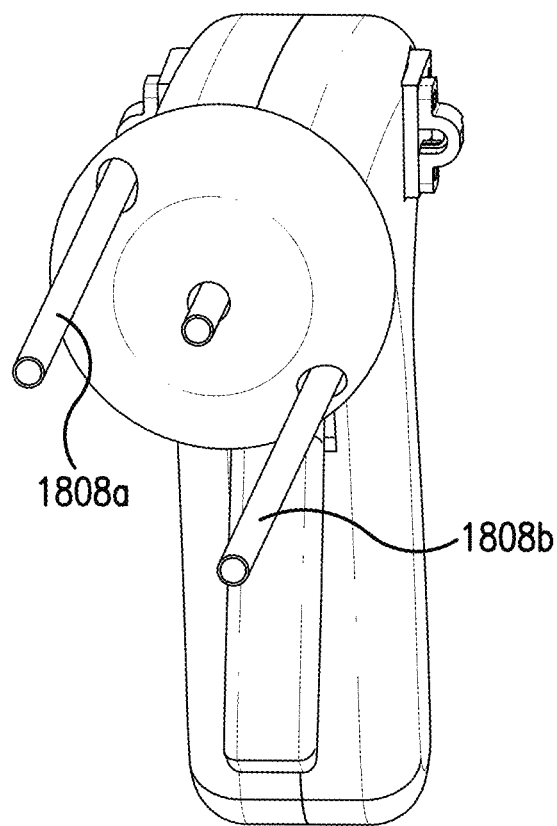
FIG. 18I is a front perspective view of the fixation device of FIG. 18G in a first lateral spacing position.
Figure 18J:
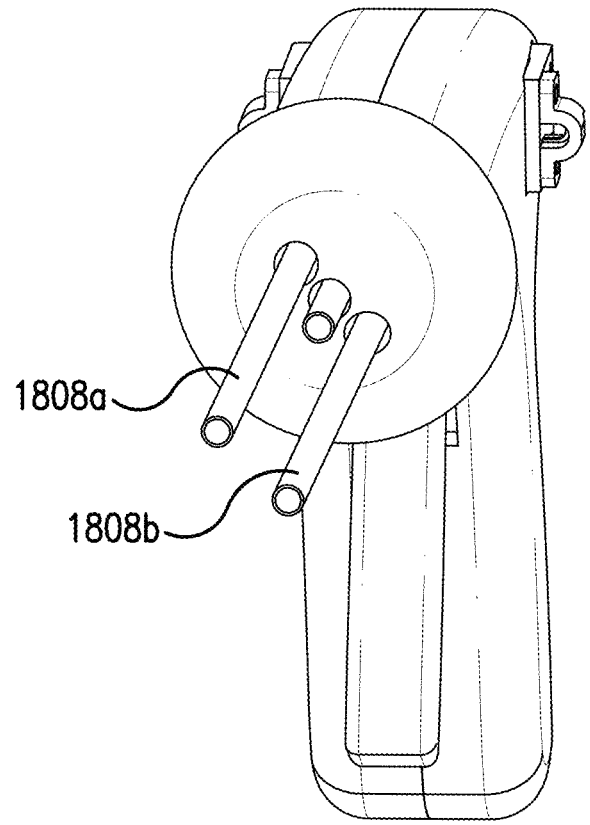
FIG. 18J is a front perspective view of the fixation device of FIG. 18G in a second lateral spacing position.

In accordance with another aspect of the disclosed subject matter, the spacial orientation of the arms 1808*a* and 1808*b* can further be controlled by rotation of one or more arms. For purpose of example, and as embodied in the exemplary device of FIGS. 18G and 18H, the arms 1808*a* and 1808*b* can be mounted on a flywheel 1824 and rotatable with respect to the housing. FIG. 18G depicts the arms 1808*a* and 1808*b* in a first roughly horizontal position and FIG. 18H depicts arms 1808*a* and 1808*b* in a second position. As embodied herein, and with reference to FIGS. 18I and 18J, devices in accordance with the disclosed subject matter can control both the rotational orientation and relative distance between arms 1808*a* and 1808*b* to facilitate onlay mesh affixation in a large variety of planes and spatial configurations.

Figure 18K:
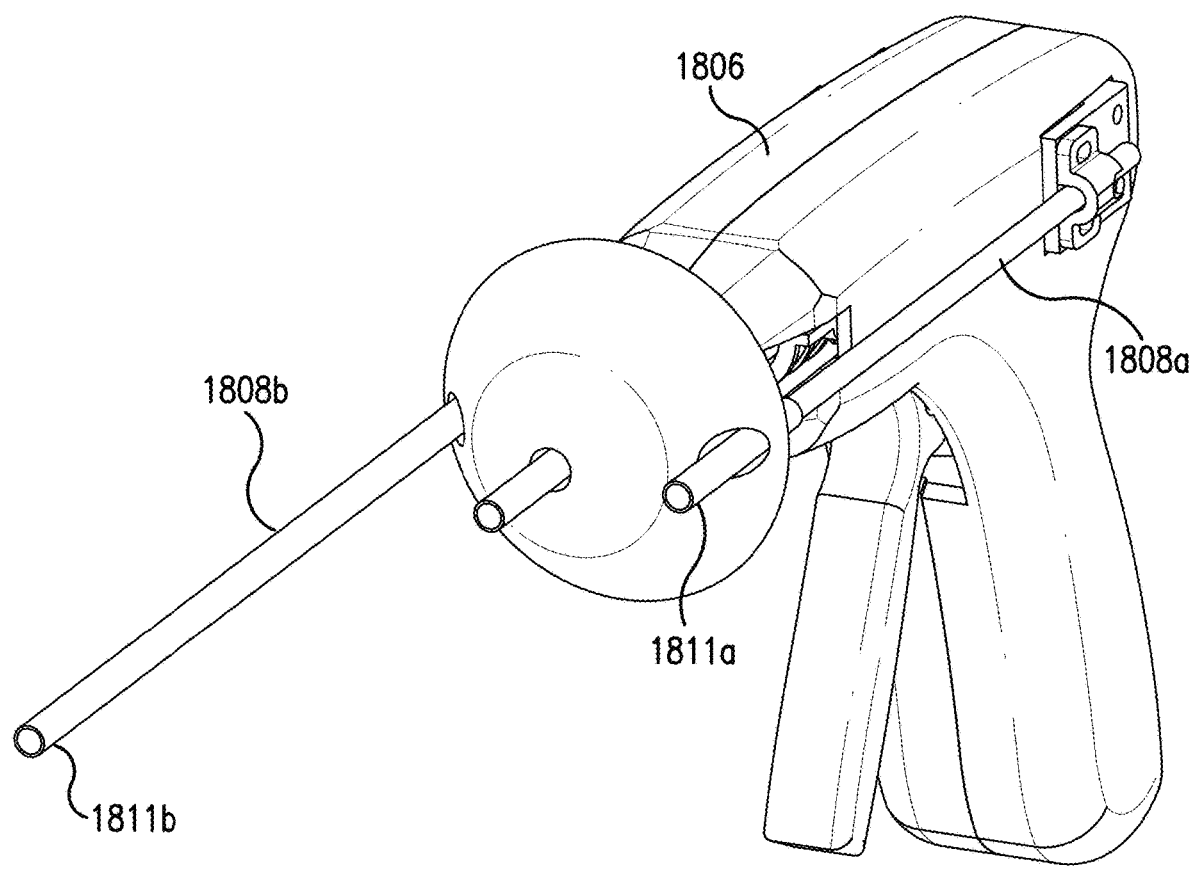
FIG. 18K is front perspective view of the fixation device of FIG. 18G with one arm in a retracted position.
Figure 18L:
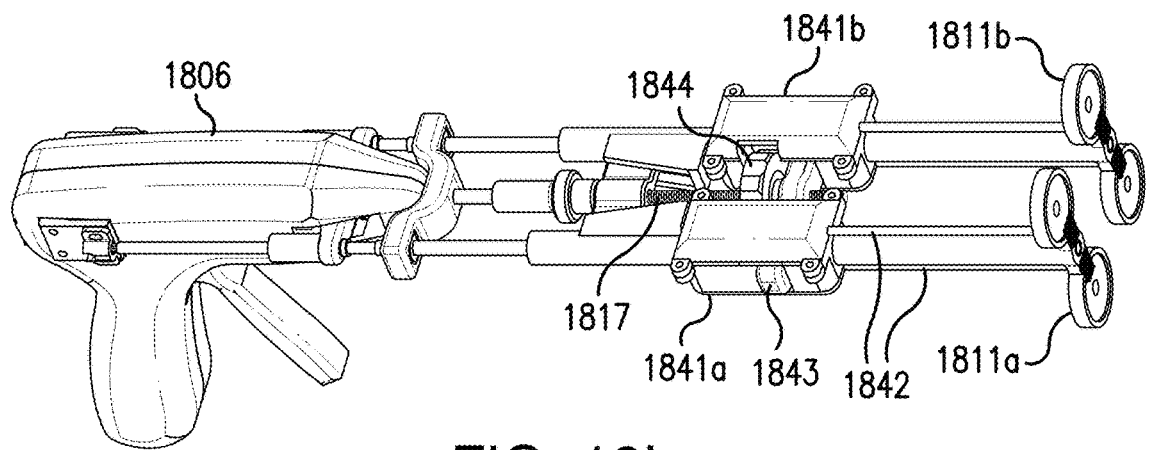
FIG. 18L is a side perspective view of a fixation device with first and second arms in accordance with an exemplary embodiment of the disclosed subject matter.
Figure 18M:
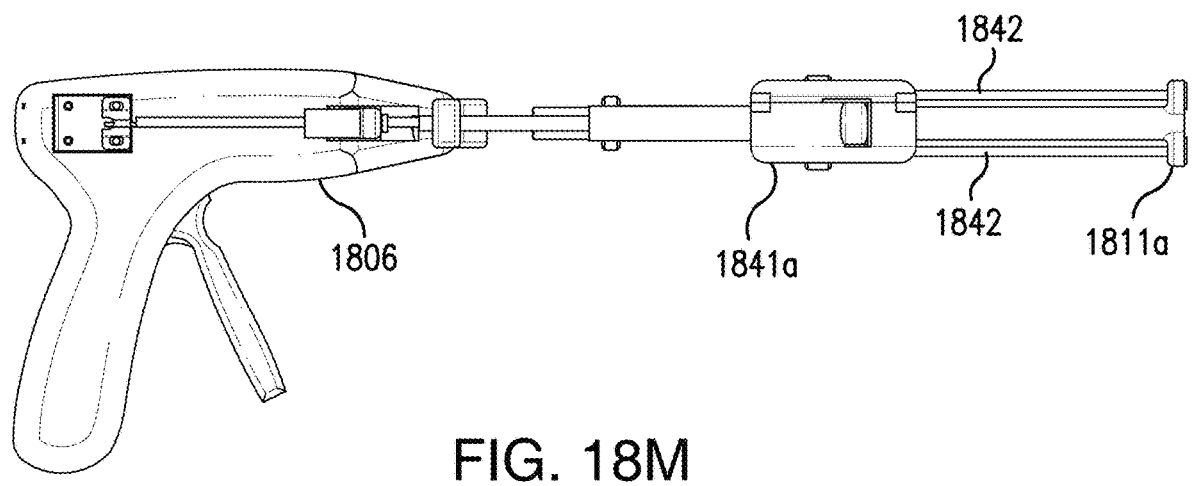
FIG. 18M is a side view of the fixation device of FIG. 18L.
Figure 18N:
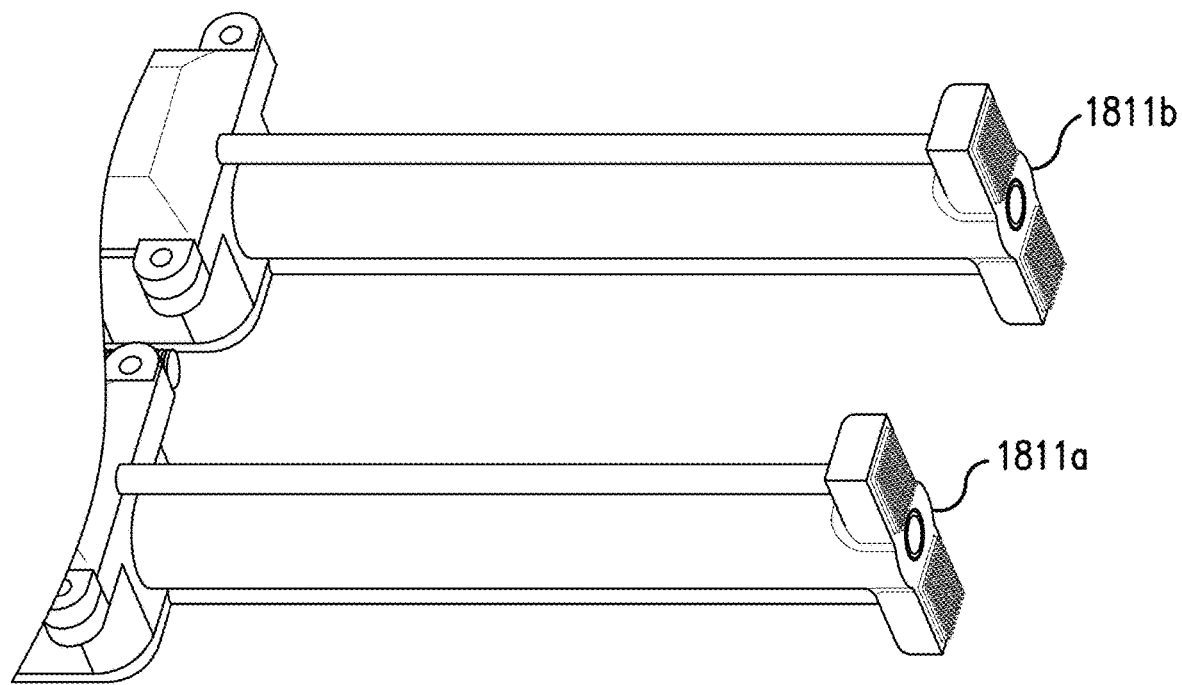
FIG. 18N is a partial perspective view of the fixation device of FIG. 18L with a rectangular distal end configuration.
Figure 18O:
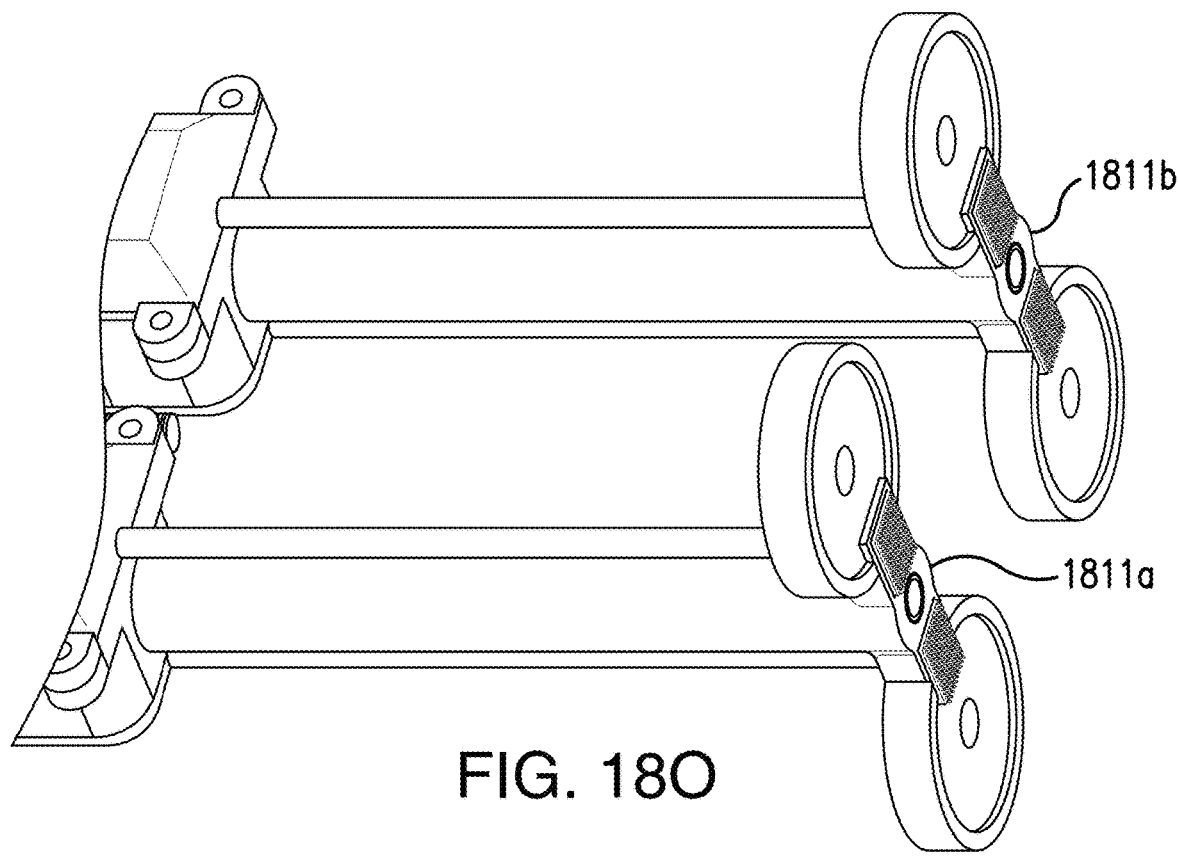
FIG. 18O is a partial perspective view of the fixation device of FIG. 18L with a circular distal end configuration in accordance with an exemplary embodiment of the disclosed subject matter.

In accordance with another aspect of the disclosed subject matter, and as embodied in the exemplary device of FIG. 18K, the spatial orientation of the first and second arms can further be controlled by optionally retracting arms proximate the housing. For example, first arm 1808*a* can be retracted such that the distal end 1811*a* of the first arm is proximate the housing 1806 while the distal end 1811*b* of the second arm 1808*b* remains extended for engaging and affixing reinforcing material. The ability to retract one or more arms of the device can be used to precisely affix a single tack in a location on the reinforcing material, such as proximate a corner of the material.

In accordance with another aspect of the disclosed subject matter the one or more fixation elements can include materials with adhesive properties. For purpose of example, and as embodied in the exemplary device of FIGS. 18L and 18M, adhesive material can be deployed or dispensed from the distal ends of the first and second arms to affix reinforcing material on opposing sides of the fascial incision. For purpose of example, a reservoir 1841 can contain the adhesive material prior to deployment. As embodied herein, the reservoir can include a first reservoir 1841*a* and a second reservoir 1841*b* mounted on the first and second arms respectively, such that the ability of the arms to move relative to one another is maintained. Alternatively, the reservoir can be separate from the device, or mounted to, or in, the housing 1806. As embodied herein, tubes 1842 can connect the reservoir 1841 to the distal ends 1811*a* and 1811*b* for dispensing adhesive material therefrom to affix reinforcing material. As embodied herein, a dial 1844 can be used to control the amount of adhesive material dispensed. Rotation of dial 1844 can cause the dial to move along threaded shaft 1817 to displace a plunger 1843 and dispense adhesive material from the distal ends 1811*a* and 1811*b*. The adhesive material can be any surgical grade material with suitable adhesive properties. For purpose of example, and not limitation, the adhesive material can include human, animal, and plant derived fibrin-based glues, synthetic materials, hemostatic glues, and mixtures and combinations thereof.

As embodied herein, fixation devices can be used with different fixation elements, both individually and in tandem. For purpose of example, affixation of the reinforcing material can include application of adhesive material and tacks with the same device. As further embodied herein, and as discussed in reference to the embodiment of FIGS. 5A-5Z, the distal ends 1811*a* and 1811*b* of the first and second arms can be coupled to the first and second arms 1808*a* and 1808*b*. This can allow the distal ends 1811*a* and 1811*b* to be selected based on surgical need. For example, and with reference to FIGS. 18N and 18O, distal ends of various sizes and shapes can be used. For example, smaller distal ends can be useful during procedures to reinforce smaller incisions and for patients with excess adipose tissue.

While reference has been made herein to a device with first and second arms, the devices and methods herein can include devices with any suitable number of arms. For example, and with reference to the embodiment of FIGS. 20A-20H, the device can further include third and fourth arms.

Figure 19A:
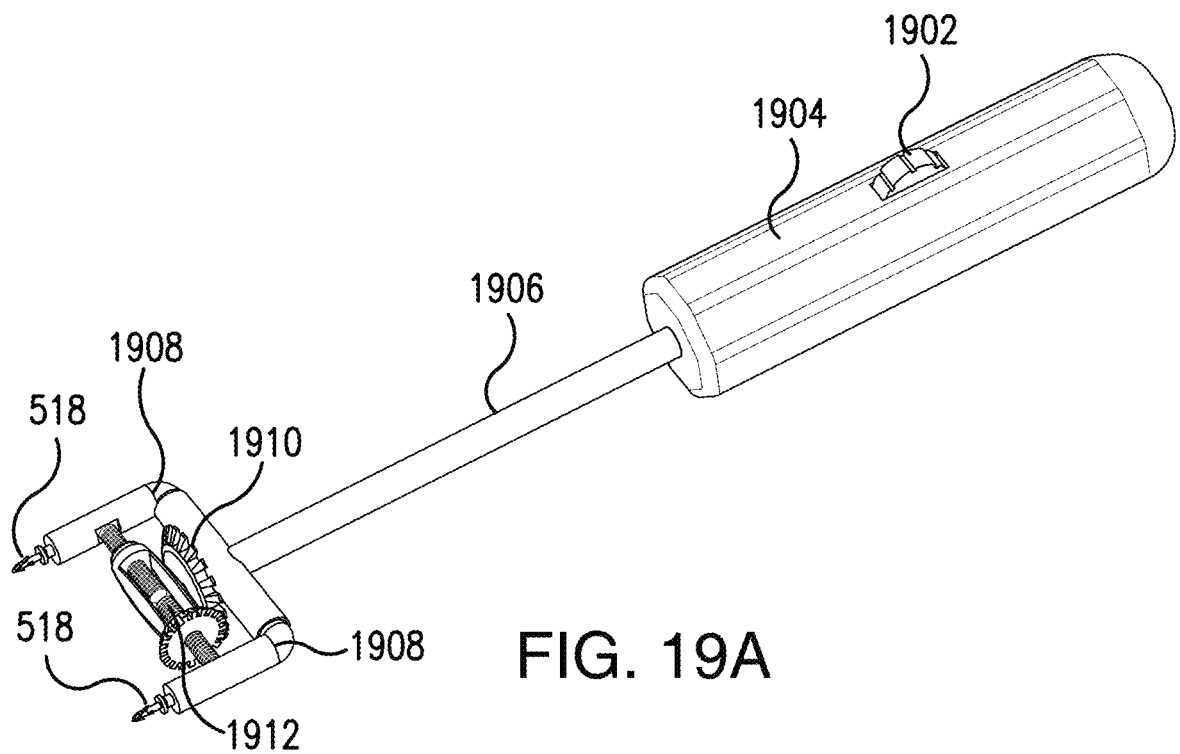
FIGS. 19A-19D illustrates diagrams of a mesh fixation device with a tensiometer in accordance with an exemplary embodiment of the disclosed subject matter.
Figure 19B:
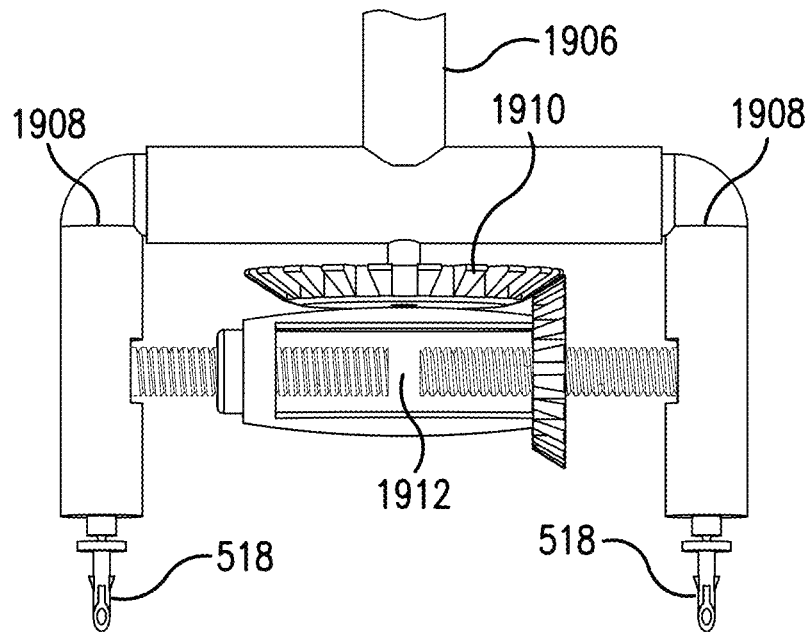
Figure 19C:
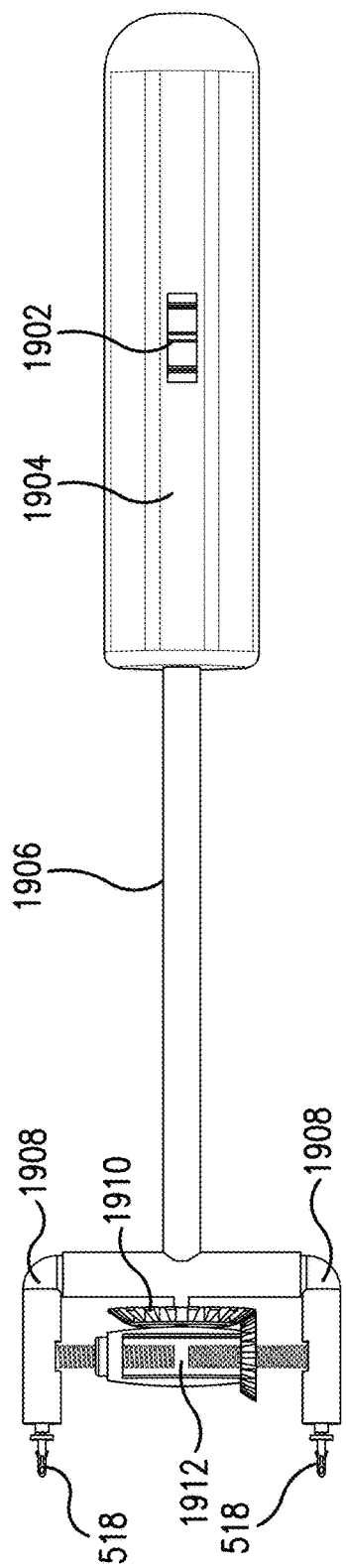

FIGS. 19A-19D illustrate an exemplary mesh fixation device with a tensiometer and spreading mechanism in accordance with another aspect of the disclosed subject matter. The exemplary embodiment depicted by FIG. 19A illustrates a dial 1902, a handle 1904, a housing 1906, a pair of arms 1908, a bevel gear 1910, a turnbuckle 1912, and a pair of tacks 518. The mesh fixation device can be held by the handle 1904. The housing 1906 can connect the handle 1904 to the arms 1908. The arms 1908 can be loaded with tacks 518. Additionally, the dial 1902 can be turned to activate the bevel gear 1910. The bevel gear 1910 can be activated to turn the turnbuckle 1912. The turnbuckle 1912 can be turned to increase or decrease the distance between the arms 1908, which can also control the tension in the mesh. FIG. 19C depicts a different view of the exemplary mesh fixation device in FIG. 19A.

Figure 19D:
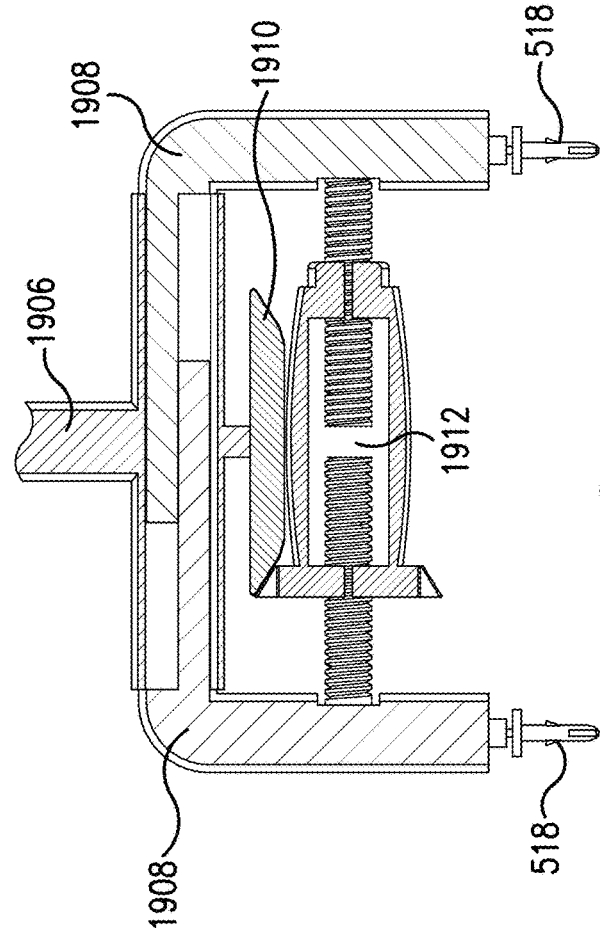

FIG. 19B depicts a magnified view of the lower portion of the exemplary mesh fixation device in FIG. 19A. FIG. 19B depicts a housing 1906, a pair of arms 1908, a bevel gear 1910, a turnbuckle 1912, and a pair of tacks 518. The housing 1906 can connect the lower portion of the device to the handle and dial. The arms 1908 can be loaded with tacks 518. The bevel gear 1910 can be activated by the dial to turn the turnbuckle 1912. The turnbuckle 1912 can be turned to increase or decrease the distance between the arms 1908, which can also control the tension applied to the mesh. FIG. 19D depicts a cross-sectional view of FIG. 19B. The housing 1906 can contain two arms 1908. The arms 1908 can move relative to each other in the housing 1906.

Figure 20C:
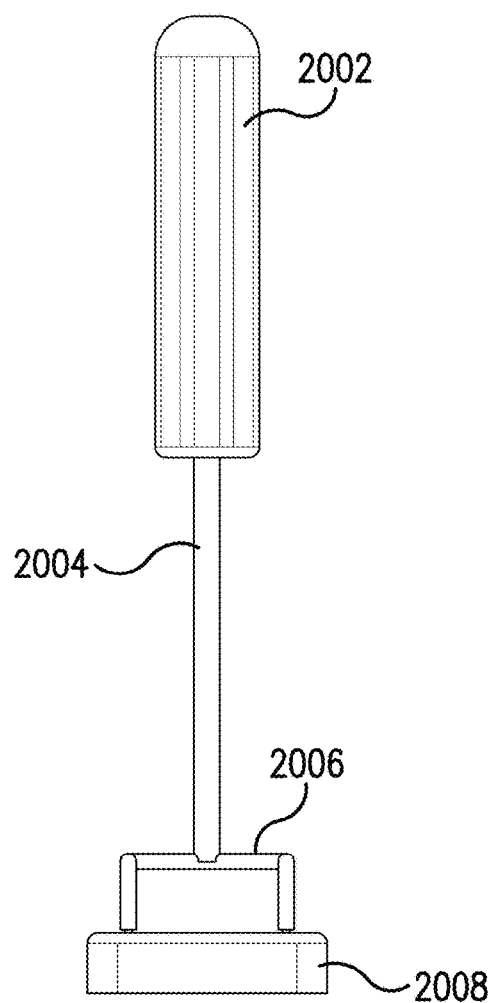
Figure 20D:
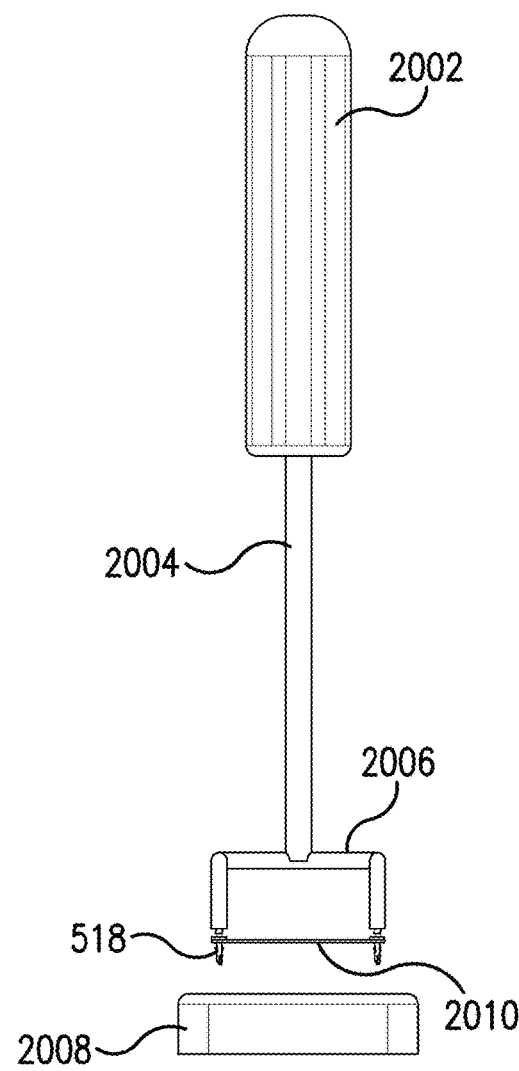
Figure 20E:
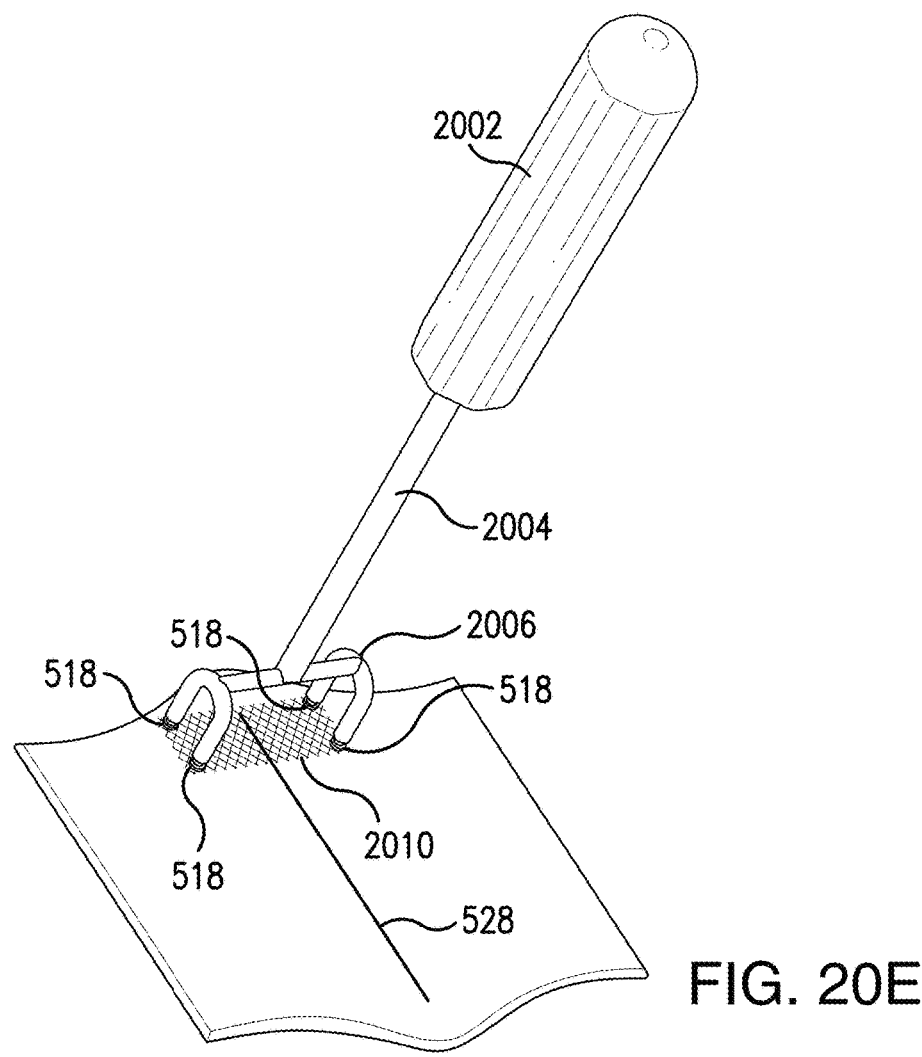
Figure 20F:
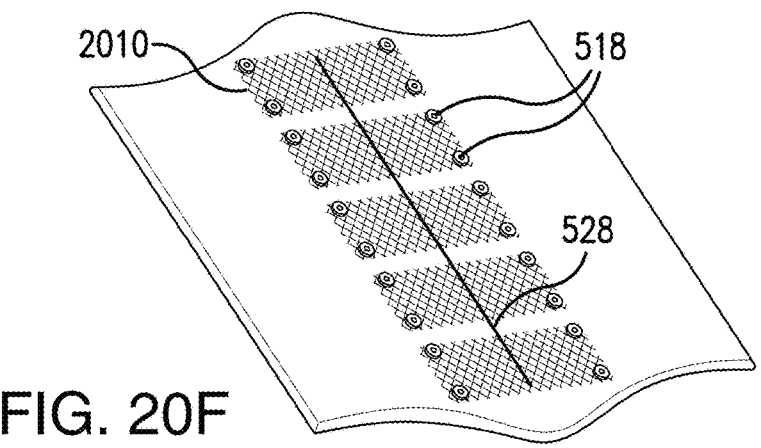

FIG. 20A-20F illustrate an exemplary procedure for fixing a mesh onto a fascia using an exemplary mesh fixation device. The exemplary embodiment depicted by FIG. 20A illustrates a mesh fixation device in proximity to a tray 2008. The tray can hold tacks 518 with an attached mesh 2010. The mesh fixation device can include a handle 2002, a shaft 2004, and an adapter 2006. The mesh fixation device can be held by the handle 2002. The shaft 2004 can connect the handle 2002 and the adapter 2006. The adapter 2006 can engage the tacks 518 and their attached mesh 2010. FIG. 20B depicts the mesh fixation device being aligned over the tray 2008. The tray can hold tacks with an attached mesh. The mesh fixation device can include pins 2012. The pins 2012 can engage the tacks. FIG. 20C depicts the mesh fixation device immersed in the tray 2008. FIG. 20D depicts the mesh fixation device being removed from the tray 2008. The pins can engage the tacks 518, such that the tacks 518 and their attached mesh 2010 can be pinned to the mesh fixation device. FIG. 20E depicts the mesh fixation device affixing a mesh 2010 using attached tacks 518 to a cover a sutured incision 528 on the fascia. The device can be aligned with the sutured incision 528. The device can then be lowered so the tacks 518 penetrate through the fascia. FIG. 20F depicts a sutured incision 528 covered with multiple (e.g., five) meshes 2010 that can be attached to tacks 518.

Figure 20G:
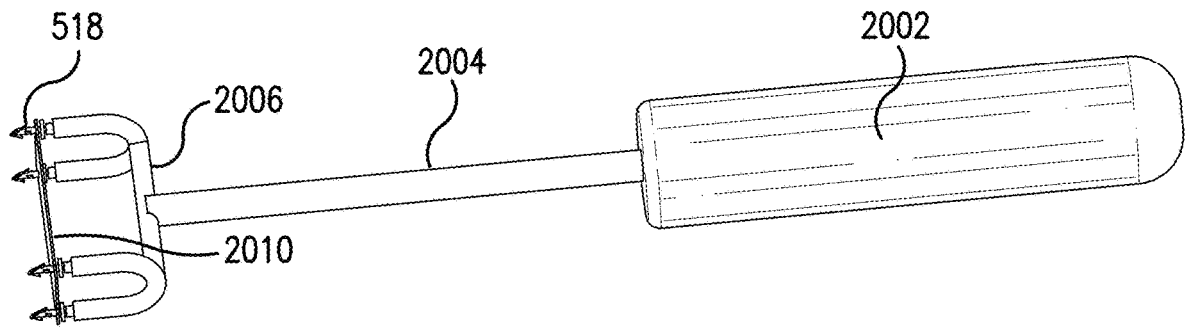
Figure 20H:
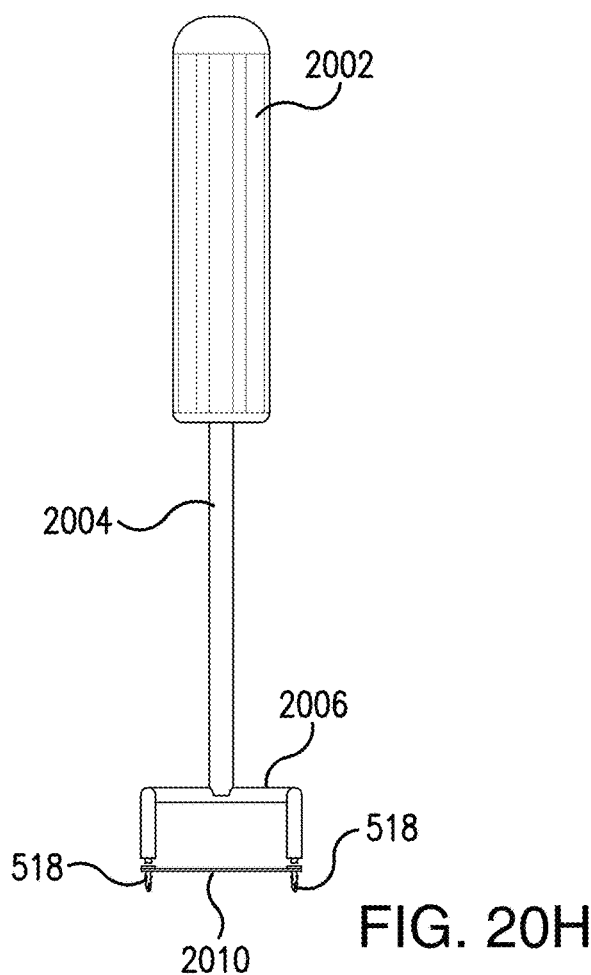

FIGS. 20G and 20H illustrate the various components of an exemplary mesh fixation device. The exemplary embodiment depicted by FIG. 20G illustrates a handle 2002, a shaft 2004, an adapter 2006, tacks 518, and a mesh 2010. The mesh fixation device can be held by the handle 2002. The shaft 2004 can connect the handle 2002 and the adapter 2006. The adapter 2006 can engage the tacks 518. The tacks 518 can hold a mesh 2010, which can be pre-tensioned. The device can also feature a tensiometer as illustrated in FIGS. 19A-19D. FIG. 20H depicts a different view of the exemplary mesh fixation device in FIG. 20G.

Figure 21A:
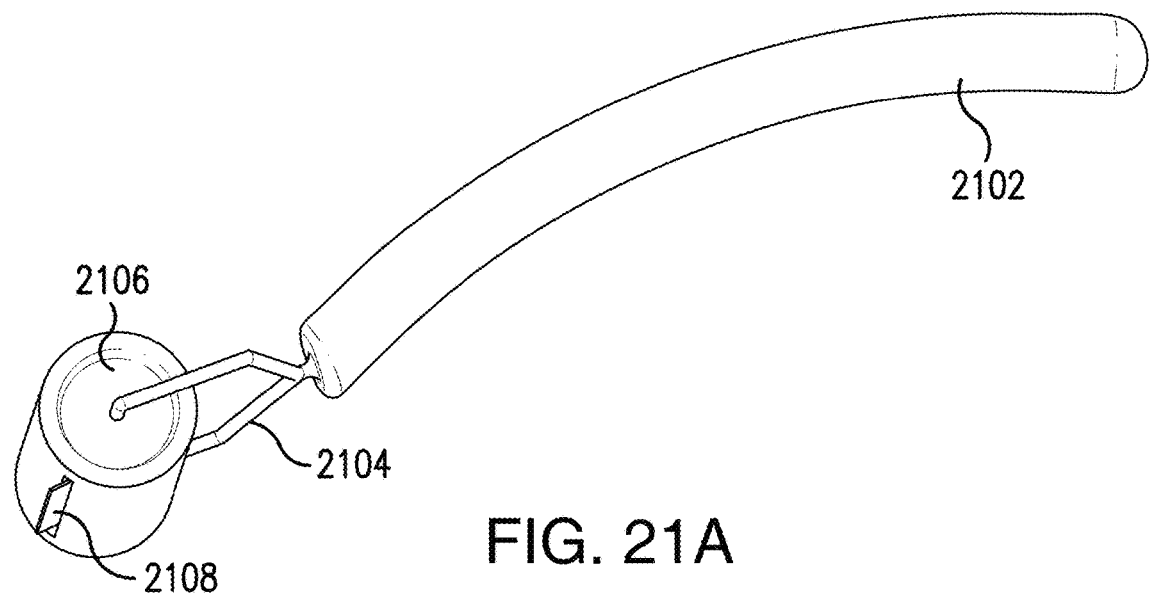
FIGS. 21A-21D illustrate diagrams of a mesh applicator configured to apply self-adhesive mesh in accordance with an exemplary embodiment of the disclosed subject matter.

FIG. 21A illustrates an exemplary mesh fixation device with self-adhesive mesh. The exemplary embodiment depicted by FIG. 21A illustrates a handle 2102, an adapter 2104, an application wheel 2106, and a self-adhesive mesh 2108. The handle 2102 can be held to use the mesh fixation device. The adapter 2104 can connect the handle 2102 to the application wheel 2106. The application wheel 2106 can house the self-adhesive mesh 2108, which can be released through a slit in the application wheel 2108. The application wheel 2106 can be rolled over the fascia to release the self-adhesive mesh.

Figure 21B:
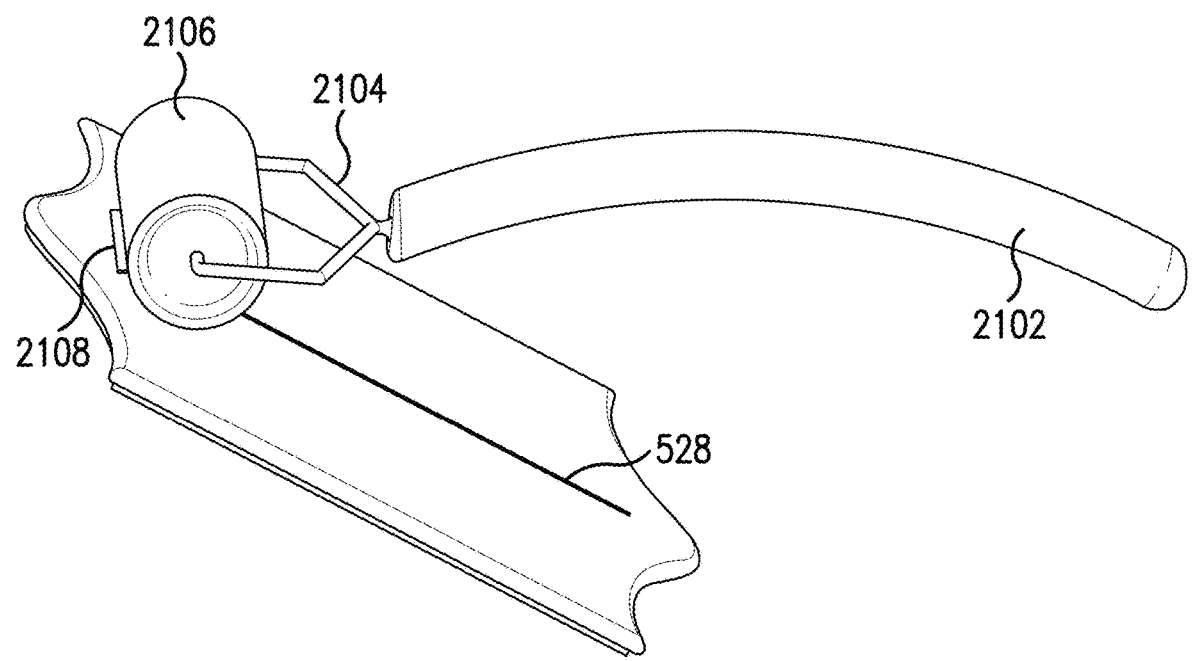
Figure 21C:
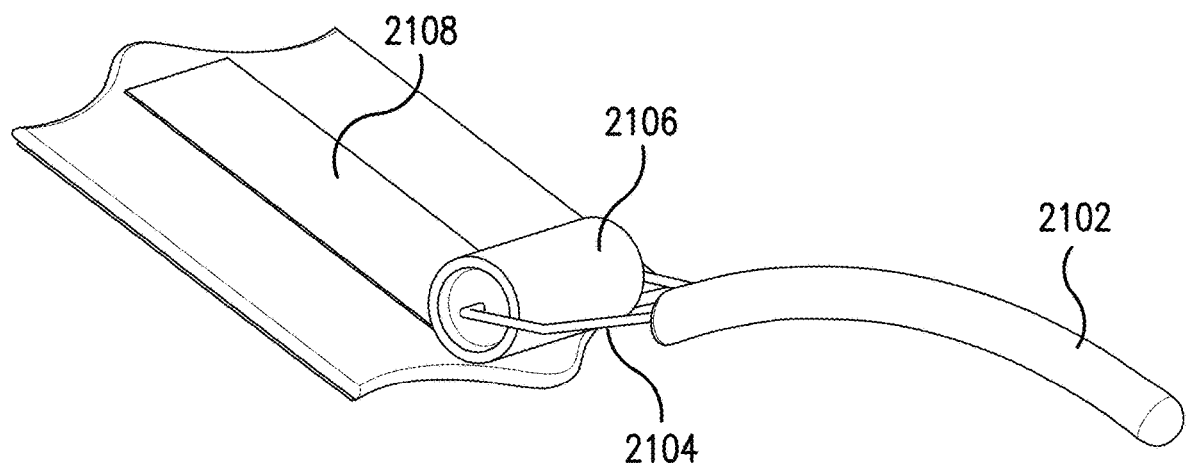

FIGS. 21B and 21C illustrate an exemplary mesh fixation device with self-adhesive mesh being rolled over a fascia. FIG. 21B depicts a sutured incision 526. The mesh fixation devices can include an application wheel 2106 and a self-adhesive mesh 2108. The application wheel 2106 can house the self-adhesive mesh 2108, which can be released through a slit in the application wheel 2106. The application wheel 2106 can be rolled over the fascia to release the self-adhesive mesh 2108. FIG. 21C depicts the sutured incision with self-adhesive mesh 2108 applied. The application wheel 2106 can be rolled over the sutured incision to release the self-adhesive mesh 2108 and cover the incision with the mesh 2108.

Figure 21D:
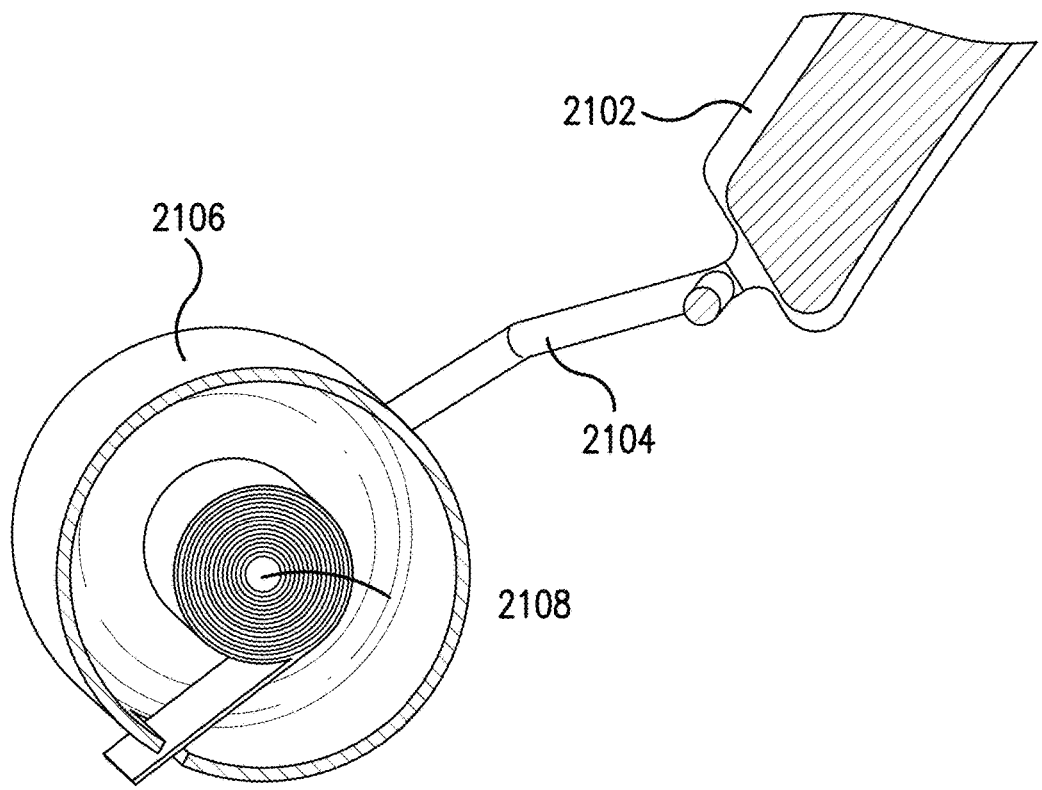

FIG. 21D illustrates a cross-sectional view of the exemplary mesh fixation device with self-adhesive mesh. The exemplary embodiment depicted by FIG. 21D illustrates an application wheel 2106 and a self-adhesive mesh 2108. The self-adhesive mesh 2108 can be rolled up and housed in the application wheel 2106. The self-adhesive mesh 2108 can be released through a slit in the application wheel 2106.

Figure 22A:
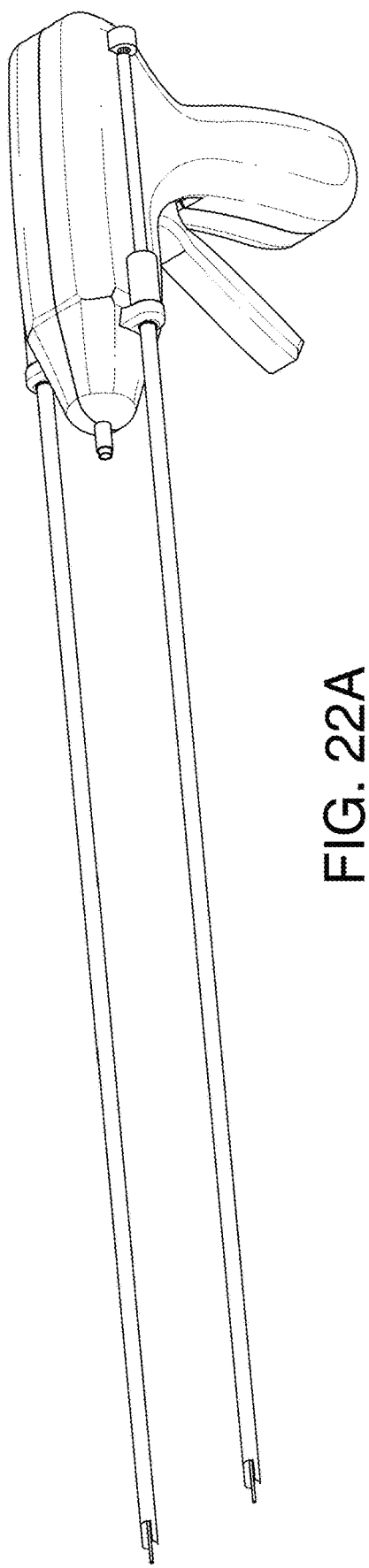
FIGS. 22A-22D illustrate diagrams of another double barrel tacker gun in accordance with an exemplary embodiment of the disclosed subject matter.
Figure 22B:
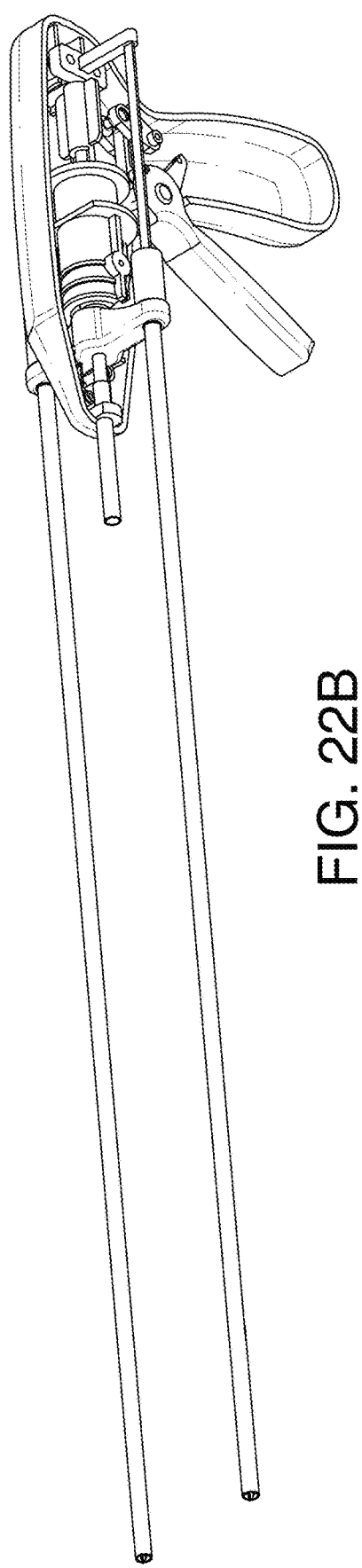
Figure 22C:
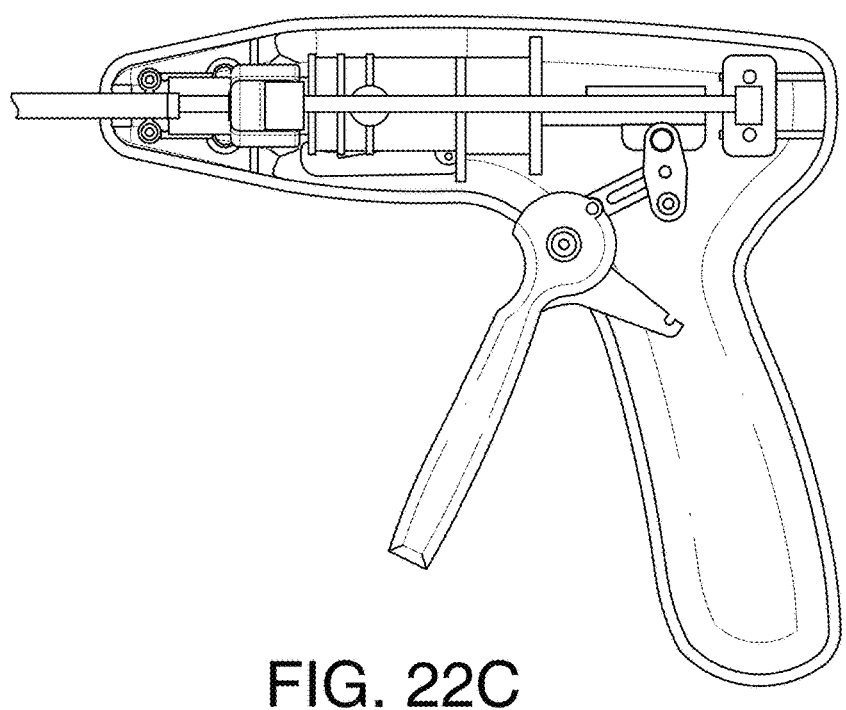
Figure 22D:
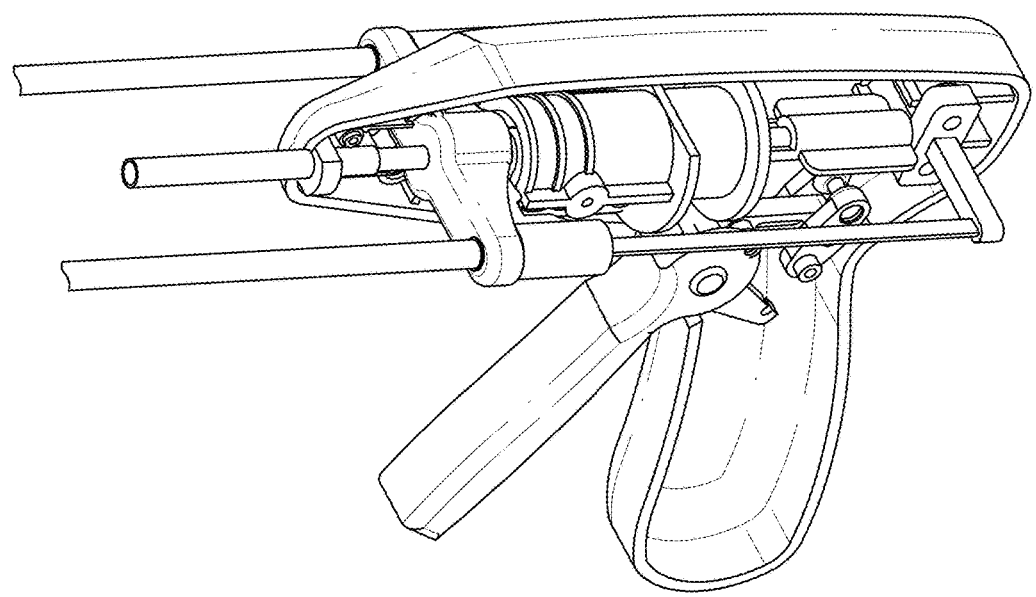

FIGS. 22A-22D illustrate multiple different views of an affixation device with first and second arms. The exemplary embodiment depicted by FIG. 22A illustrates that the length of the first and second arms, or barrels, can be selected for specific surgical needs. For purpose of example, and not limitation, the embodiment depicted by FIG. 22A has longer twin barrels compared to the embodiments depicted in FIGS. 18A-18O, and is hereinafter referred to as the double long barrel tacker gun. FIG. 22B illustrates the interior components of the double long barrel tacker gun of FIG. 22A. FIG. 22C and FIG. 22D different close up views of the housing, handle, and trigger portions of the double long barrel tacker gun depicted in FIG. 22A and FIG. 22B. The trigger can be depressed to fire two tacks simultaneously at a set distance from each other. The tacks can be housed inside of each barrel.

Figure 23:
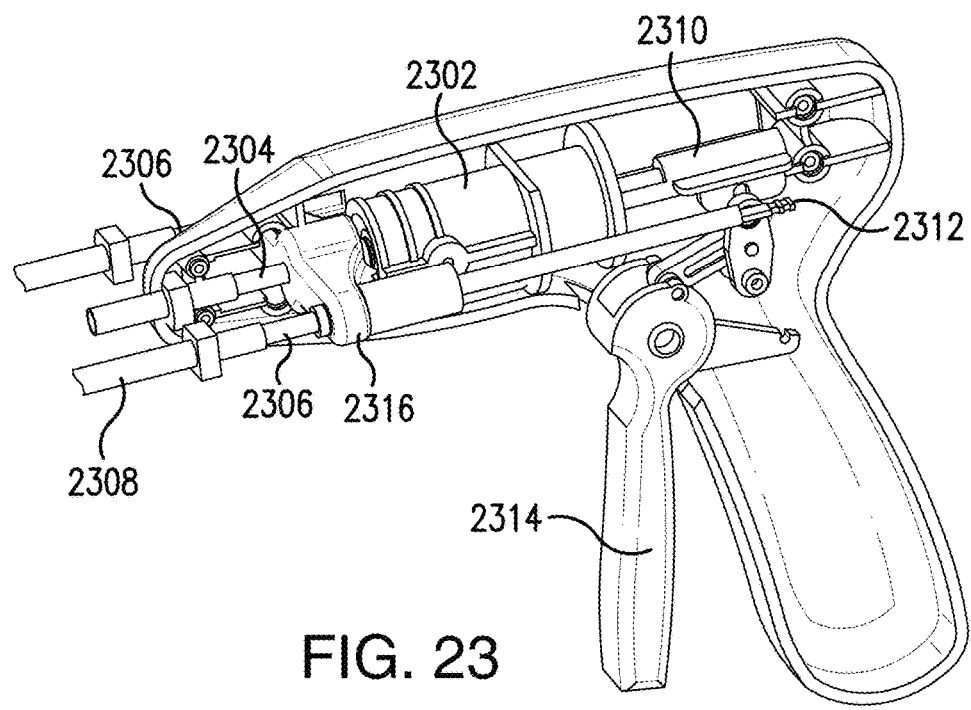
FIG. 23 illustrates a diagram of the components of the double barrel tacker gun shown in FIGS. 22A-22D in accordance with an exemplary embodiment of the disclosed subject matter.

FIG. 23 illustrates a diagram of the components of the double long barrel tacker gun shown in FIGS. 22A-22D. As illustrated in FIG. 23, the double long barrel tacker gun can include a housing 2302 that includes a firing mechanism which is illustrated in greater detail in FIG. 24. For purpose of example, and as shown in FIG. 23, the double long barrel tacker gun can include spring-loaded actuating center arm 2304, tack penetration arms 2306, the barrel housing 2308 in which tacks are stored, a connector bracket 2316, a trigger 2314, a tack advancing rod 2312, and a plunger 2310. As the trigger 2314 is pressed, the plunger 2310, which is connected to the trigger 22314 is advanced, can cause the tack advancing rod 2312 to advance. In some embodiments, the plunger 2310 can cause the spring-loaded mechanism inside housing 2302 to advance, via connector bracket 2316, the spring loaded actuating center arm 2304, the tack advancing rod 2312, and the tack penetration arms 2306. As the tack penetration arms 2306 and the tack advancing rod 2312 move forward, the barrel housing 2308 can also move forward and at least one tack stored in each of the two barrel housings 2308 can be deployed and the rest of the tacks in the barrel housing 2308 can advance forward as tack advancing rod 2312 pushes the remainder of the tacks stored inside the barrel housing 2308 forward.

Figure 24:
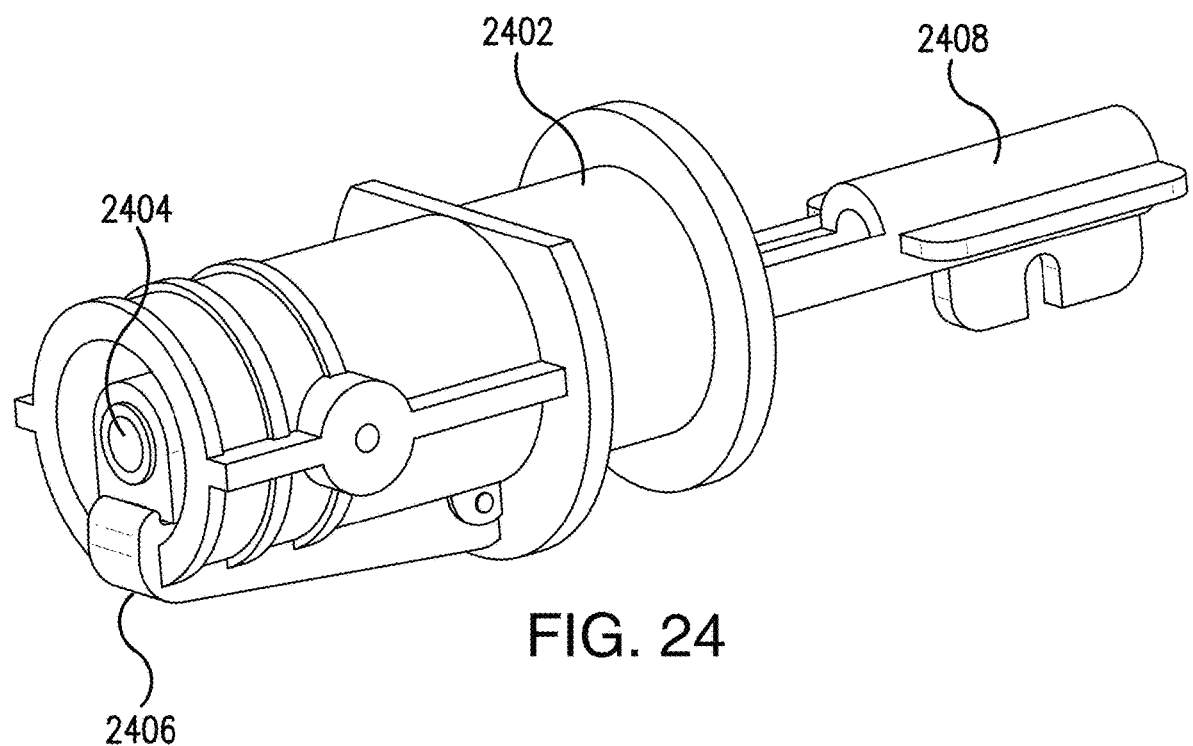
FIG. 24 illustrates a diagram of the spring loaded component of the double barrel tacker gun shown in FIGS. 22A-22D and FIG. 23 in accordance with an exemplary embodiment of the disclosed subject matter.
Figure 25A:
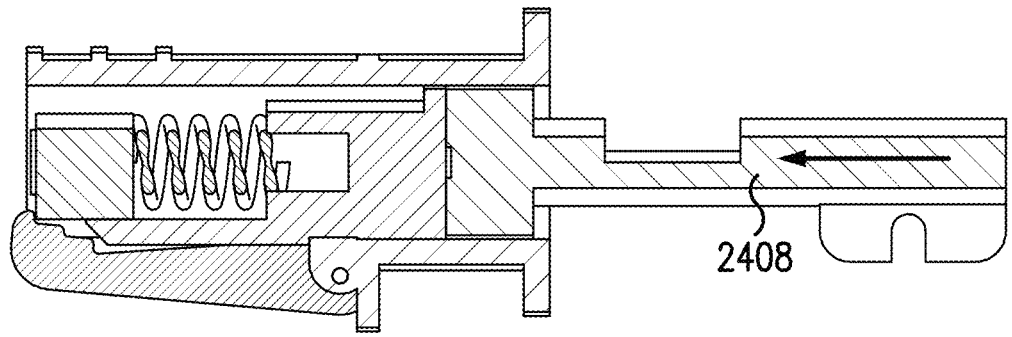
FIGS. 25A-25C illustrate diagrams of the spring loaded component of the double barrel tacker gun shown in FIG. 24 being activated in accordance with an exemplary embodiment of the disclosed subject matter.
Figure 25B:
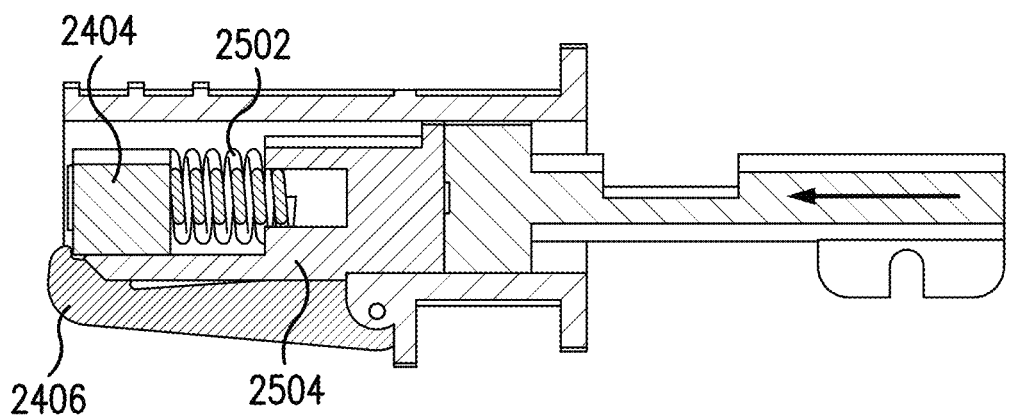
Figure 25C:
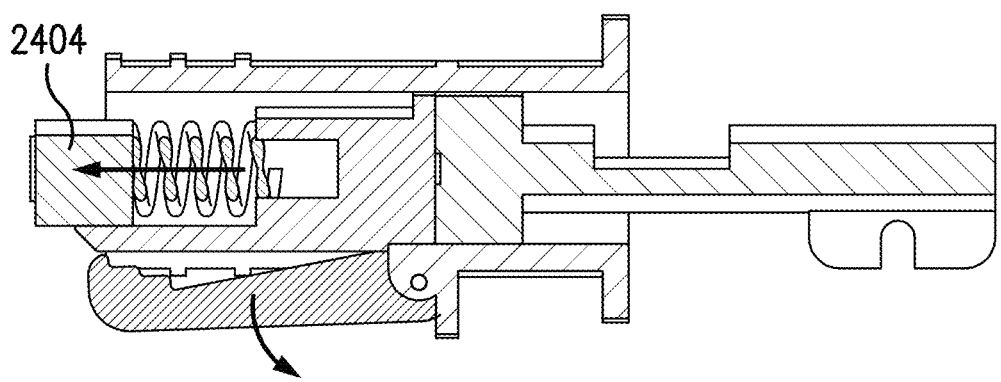

FIG. 24 illustrates a diagram of an exemplary firing mechanism including a spring-loaded component. For purpose of example, the spring loaded component can include a housing 2402, corresponding to housing 2302. The spring loaded component can also include a cam driver 2404, a cam lock 2406, and a plunger 2408, which corresponds to plunger 2310. FIGS. 25A-25C describe how the spring loaded component functions.

FIGS. 25A-25C illustrate diagrams of the spring loaded component of the double long barrel tacker gun shown in FIG. 24 being activated. As illustrated in FIG. 25A, pushing the trigger forward can cause the plunger 2408 to move forward. As illustrated in FIG. 25B, the cam driver 2404 can be held in cam lock 2406, allowing the spring 2502 to be compressed. As illustrated in FIG. 25C, as the plunger 2408 moves forward and pushes driver 2504, driver 2504 can push the cam lock 2406 out of the way, allowing the cam driver 2404 to release and fire forward.

Figure 26:
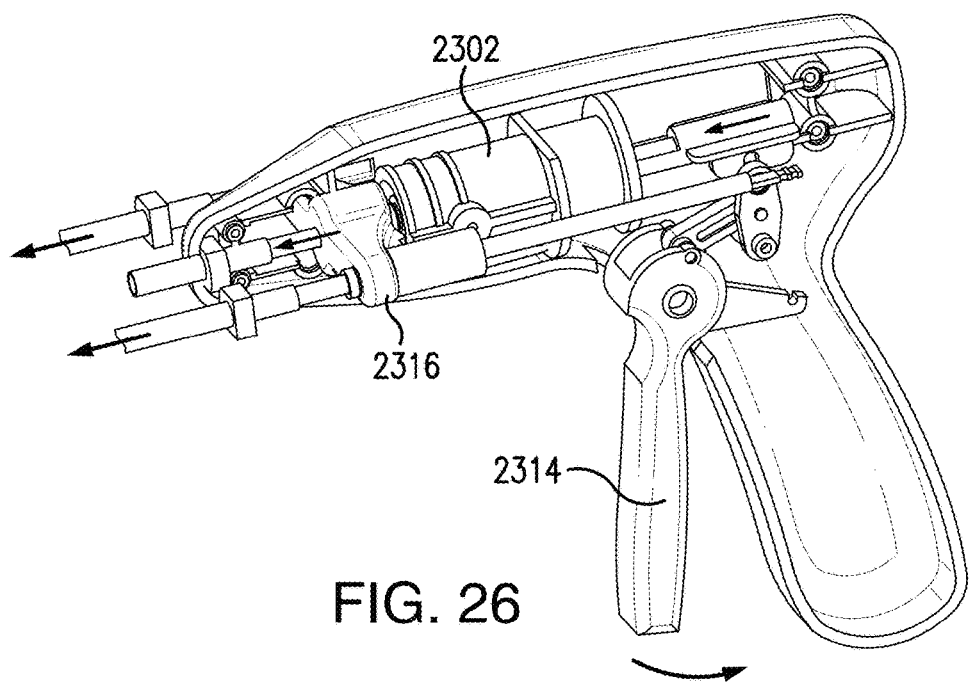
FIG. 26 illustrates a diagram depicting the function of the components of the double barrel tacker gun shown in FIGS. 22A-22D in accordance with an exemplary embodiment of the disclosed subject matter.

FIG. 26 illustrates a diagram depicting the function of the components of the double long barrel tacker gun shown in FIGS. 22A-22D. When the trigger 2314 is pulled and/or activated, trigger can push the plunger forward since the trigger is mechanically linked and/or coupled to the plunger. As the plunger moves forward, as illustrated in greater detail in FIGS. 25A-25C, the spring-loaded component can cause the spring to compress and eventually fire the cam driver. Once the cam lock is pushed out of the way and the spring releases, the spring-loaded actuating center arm 2304 can strike and/or advance forward, thereby creating an impact load. This impact load can be transferred to the tack penetration arms 2306 and tack advancing rod 2312 via the connector bracket 2316. Additionally, or alternatively, the firing mechanism can include pneumatic components and can generate impact loads using compressed gases, such as carbon dioxide.

Figure 27:
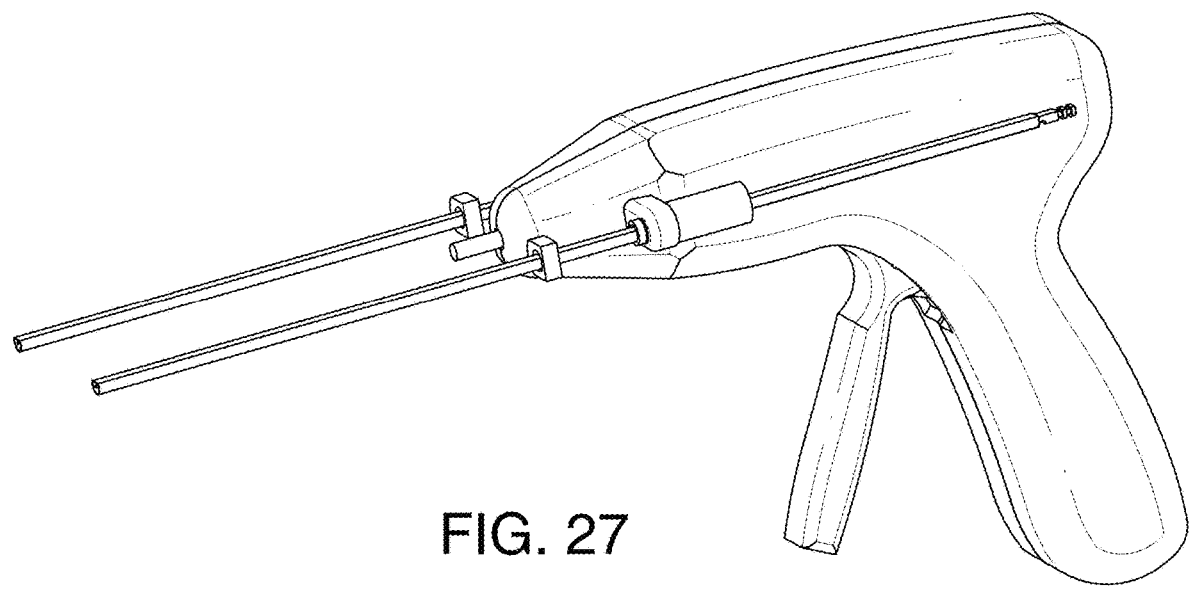
FIG. 27 illustrates a diagram of another double barrel tacker gun in accordance with an exemplary embodiment of the disclosed subject matter.

FIG. 27 illustrates a diagram of another double barrel tacker gun. The double barrel tacker gun of FIG. 27 can operate in a similar manner and provide the same functionality as that of the double long barrel tacker gun described above in FIGS. 22A-FIG. 26. However, the double barrel tacker gun of FIG. 27 can have shorter barrel lengths than the barrel housing 2308 of the double long barrel tacker gun described above in FIGS. 22A-FIG. 26. In some embodiments, the double barrel tacker gun of FIG. 27 and the double barrel tacker gun of FIG. 27 can operate in a similar manner.

FIGS. 28A-D illustrate diagrams of different views of a manual tacker with a tack retainer. FIG. 28A illustrates a side view of the manual tacker with a tack retainer 2804. As shown in FIG. 28A, the manual tacker can include a tack retainer 2804 that can retain a tack 2802, a neck 2806, a retainer sleeve 2808, a handle 2810 to disengage the retainer 2804 and a handle 2812 by which a user can grip and/or hold the manual tacker. FIG. 28B shows a top down view of the manual tack retainer approaching a fascia with a surgical mesh being used to cover the incision on which the manual tacker will place penetrating tack 2802 to secure the mesh to the fascia. FIG. 28C and FIG. 28D show enlarged views of the manual tack retainer showing close up views of the neck 2806, tack retainer 2804 and the tack 2802. As illustrated by FIGS. 28A-D the manual tacker can include telescoping fingers that can hold onto the tack 2802 in the manual tacker. In some embodiments, the retainer sleeve 2808 can allow the user of the manual tacker to securely hold on to the tack 2802 while having full spatial control of the manual tacker. In some embodiments, the user can affix the tack 2802 by manually pushing it through the mesh and/or fascia and then pull up on the retainer 2804 to disengage the tack 2802. In some embodiments, when the retainer 2804 is pulled up, the retainer 2808's arms can open, thereby releasing the tack 2802. In some embodiments, the geometry of the neck 2806 and the retainer sleeve 2808 can make the retainer 2804's arms spread open as the retainer 2804 is pulled upwards. In some embodiments, the tack 2802 can also be stabilized by a pin that goes through the length of the tack 2802.

Figure 29A:
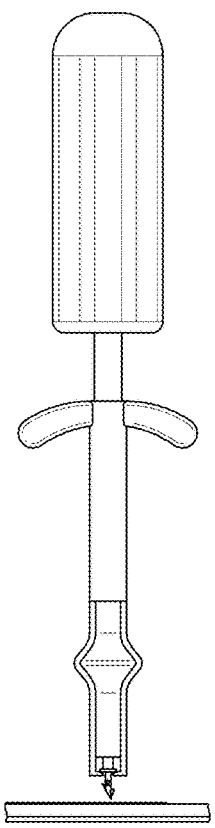
FIGS. 29A-E illustrate diagrams of a process by which the manual tacker with a tack retainer of FIGS. 28A-D engages with the mesh and fascia in accordance with an exemplary embodiment of the disclosed subject matter.
Figure 29B:
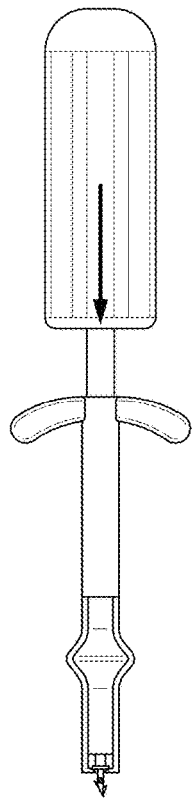
Figure 29C:
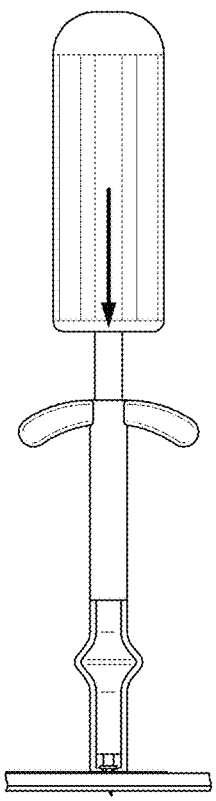
Figure 29D:
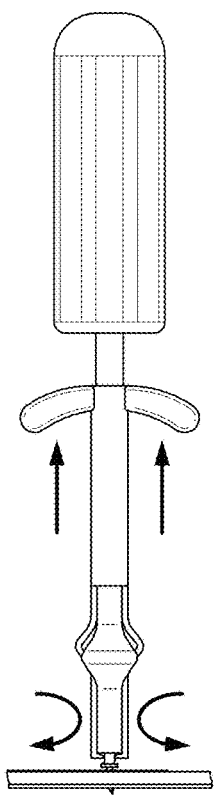
Figure 29E:
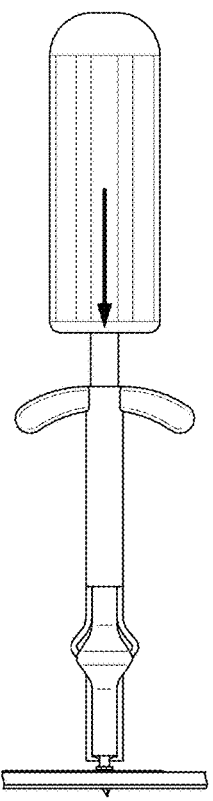

FIGS. 29A-E illustrate diagrams of a process by which the manual tacker with a tack retainer of FIGS. 28A-D engages with the mesh and fascia. As illustrated in FIG. 29A, the manual tacker can be positioned over the mesh and/or fascia. As illustrated in FIG. 29B, the manual tacker can be positioned to approach the mesh and/or fascia. As illustrated in FIG. 29C, the manual tacker can be pushed down on the mesh and/or fascia using the handle 2812. As illustrated in FIG. 29D, the retainer 2804 can be pulled up using the retainer handle 2810. As illustrated in FIG. 29E, the manual tacker can be continued to pushed down, using the handle 2812, to fully affix the tack 2802 onto the mesh and/or fascia.

Figure 29F:
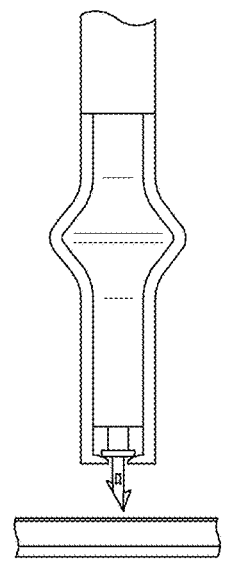
FIGS. 29F-J illustrate diagrams showing an enlarged version of a process by which the manual tacker with a tack retainer illustrated in FIGS. 29A-E by zooming in on the retainer portion of the manual tacker in accordance with an exemplary embodiment of the disclosed subject matter.
Figure 29G:
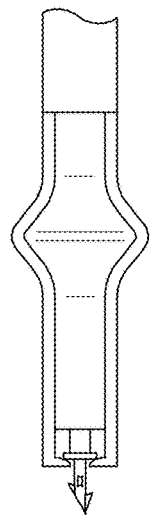
Figure 29H:
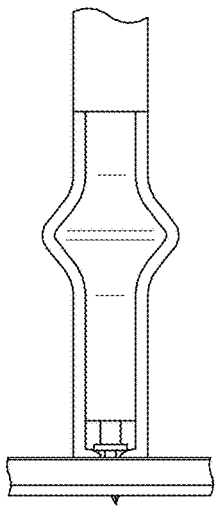
Figure 29I:
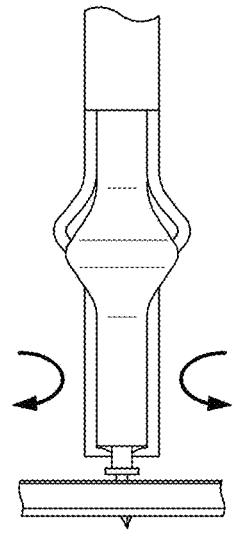
Figure 29J:
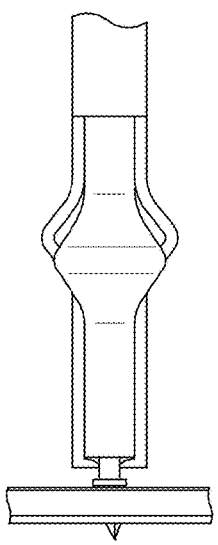

FIGS. 29F-J illustrate diagrams showing an enlarged version of a process by which the manual tacker with a tack retainer illustrated in FIGS. 29A-E by zooming in on the retainer portion of the manual tacker. For example, FIG. 29F is an enlarged version of FIG. 29A that is enlarged to show the retainer 2804, neck 2806, and tack 2802 in greater detail as the manual tacker is positioned over the mesh and/or fascia. FIG. 29G is an enlarged version of FIG. 29B that is enlarged to show the retainer 2804, neck 2806, and tack 2802 in greater detail as the manual tacker is positioned to approach the mesh and/or fascia. FIG. 29H is an enlarged version of FIG. 29C that is enlarged to show the retainer 2804, neck 2806, and tack 2802 in greater detail as the manual tacker is pushed down on the mesh and/or fascia. For example, FIG. 29I is an enlarged version of FIG. 29D that is enlarged to show the retainer 2804, neck 2806, and tack 2802 in greater detail as the retainer is pulled up using the retainer handle. FIG. 29J is an enlarged version of FIG. 29E that is enlarged to show the retainer 2804, neck 2806, and tack 2802 in greater detail as the manual tacker is continued to be pushed onto the mesh and/or fascia to fully affix the tack.

Figure 30:
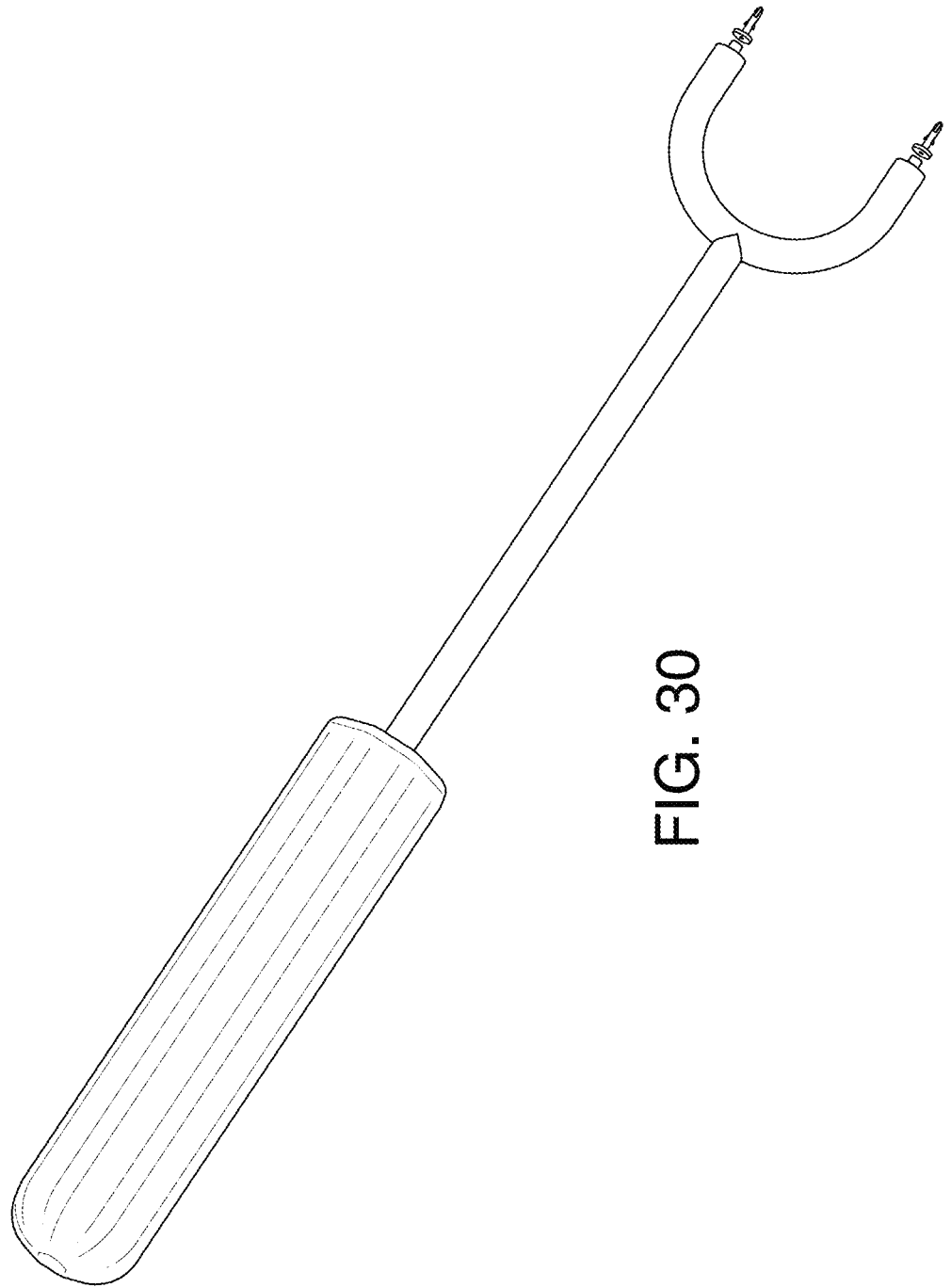
FIG. 30 illustrates a diagram of a double manual tacker in accordance with an exemplary embodiment of the disclosed subject matter.

FIG. 30 illustrates a diagram of a double manual tacker. As illustrated in FIG. 30, the retainer sleeve and tack retainer concept illustrated in FIGS. 28A-29J can be incorporated into the double manual tacker described in connection with FIGS. 1A-5Z above.

Figure 31A:
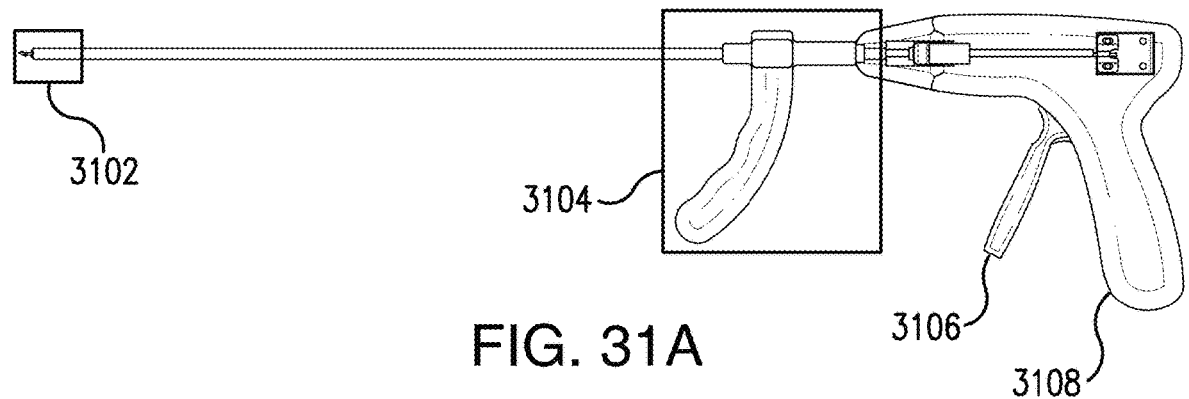
FIGS. 31A-E illustrate diagrams of different views of a two-stage tacker gun with a secondary handle in accordance with an exemplary embodiment of the disclosed subject matter.
Figure 31B:
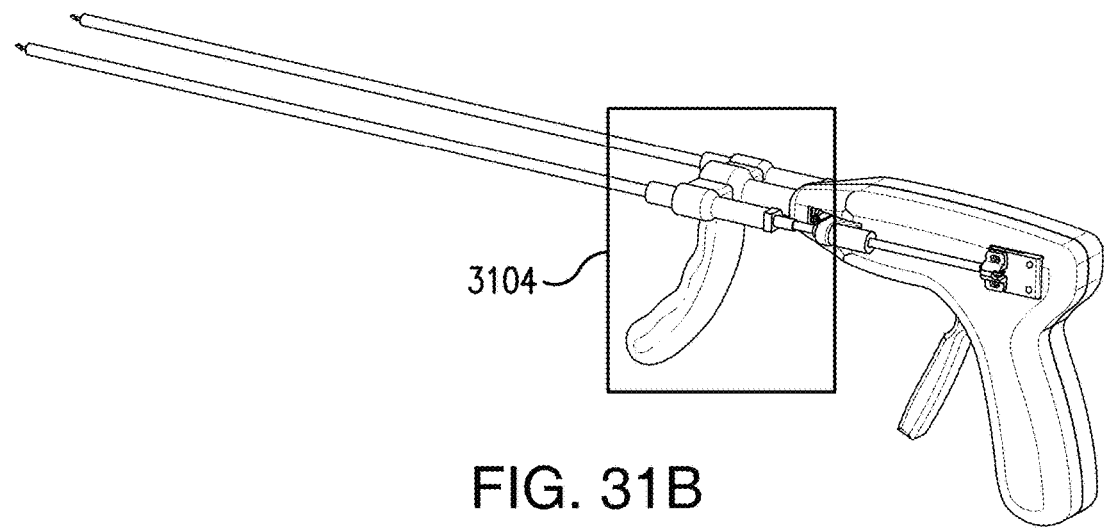
Figure 31C:
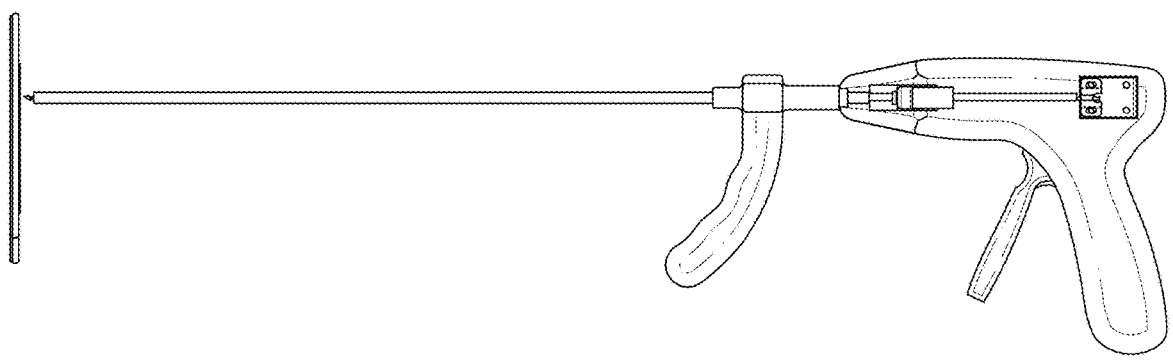
Figure 31D:
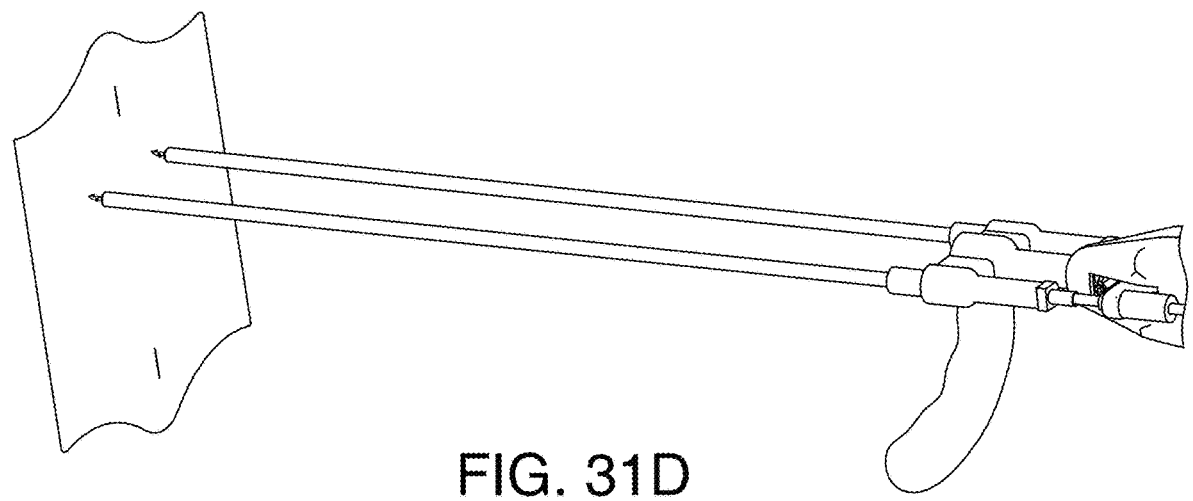
Figure 31E:
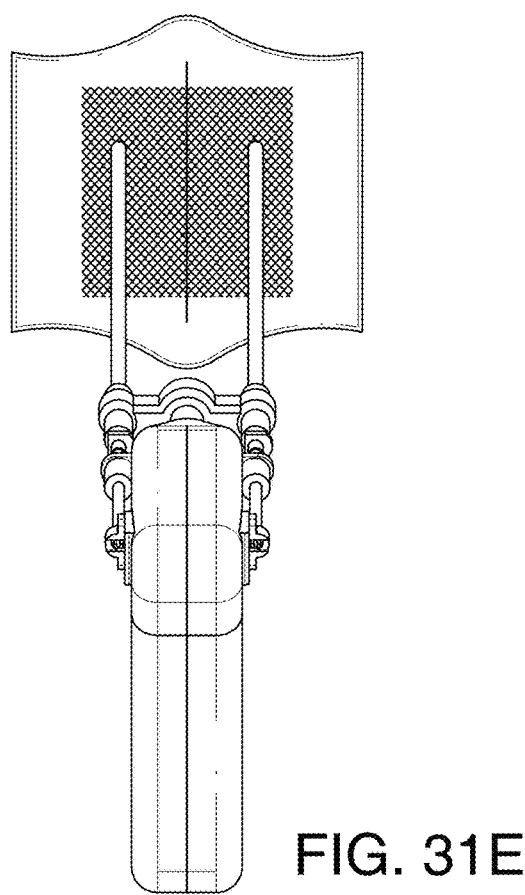

FIGS. 31A-E illustrate diagrams of different views of an exemplary embodiment of a fixation device in accordance with the disclosed subject matter having two arms and a secondary handle. For purpose of illustration, and as illustrated in FIG. 31A, the dual-arm fixation device can include a secondary handle 3104 which can be an ergonomically shaped to provide increased stability and control of the tacker gun. The dual-arm fixation device can also include an exposed tack 3102 for two-staged penetration of the mesh and/or fascia as shown in FIGS. 33A-37D. The first stage of the two-stage penetration process can be manually performed using the two-stage tacker gun and the second stage of the two-stage penetration process can be performed with a firing mechanism, such as a compressed spring. FIGS. 31B-E illustrate different views of the two-stage tacker gun. As embodied herein, the secondary handle 3104 can allow for the user to have more stability with the tacker gun and therefore have more control over the placement of the tack 3102. In some embodiments, the user can be able to use both of his/her hands to activate the two-stage tacker gun. For example, the primary handle 3108 with the trigger 3106 can be held by the user's first hand while the secondary and stabilizing handle 3104 can be held on the user's second hand.

Figure 32A:
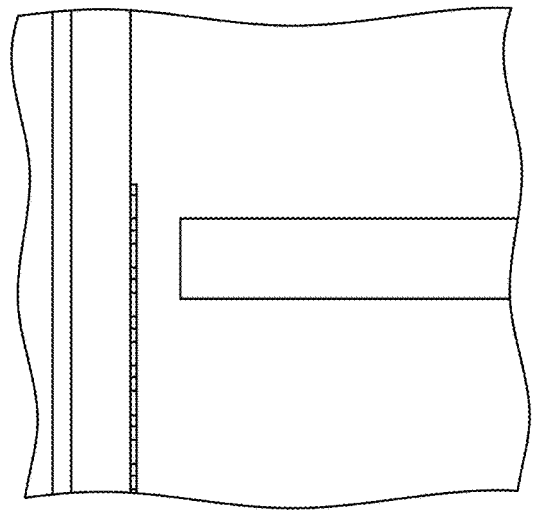
FIGS. 32A-B illustrate diagrams of different views of traditional tacker guns with an unexposed tack.
Figure 32B:
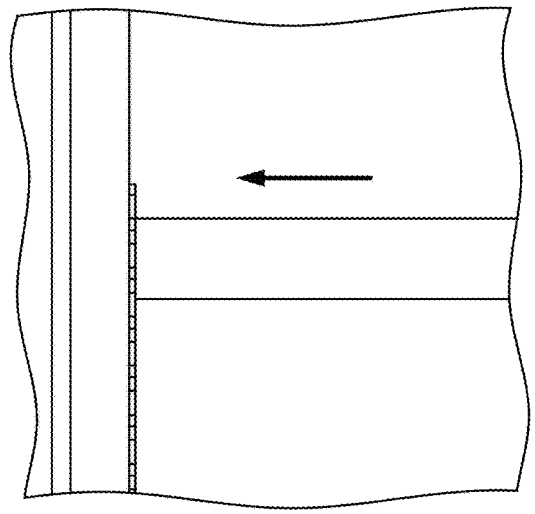

FIGS. 32A-B illustrate diagrams of different views of traditional tacker guns with an unexposed tack. Traditional tacker guns can experience difficulty in fully penetrating tacks through fascia when attempting to fire the tacks through a strip of mesh. Because traditional tacker guns make initial contact between the tacker gun and mesh by the tacker gun barrel (as illustrated in FIGS. 32A-B), traditional tacker guns can experience such difficulty in fully penetrating the tacks. As the user pushes the barrel of the traditional tacker gun onto the mesh/fascia before firing the tacker gun, the local tension in the mesh increases. This tensioned mesh can act as a barrier that makes it more difficult for the tack to penetrate through the mesh and/or fascia.

Figure 33A:
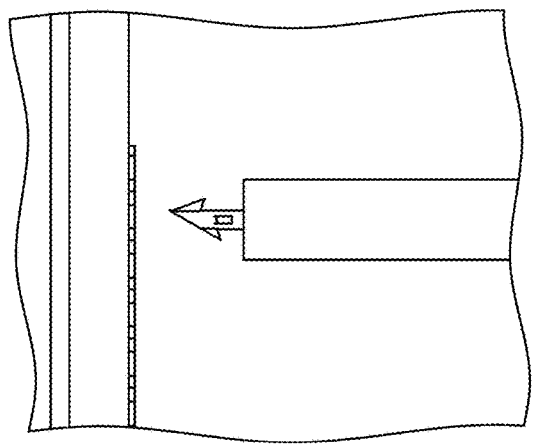
FIGS. 33A-B illustrate diagrams of different views of the two-stage tacker gun with an exposed tack in accordance with an exemplary embodiment of the disclosed subject matter.
Figure 33B:
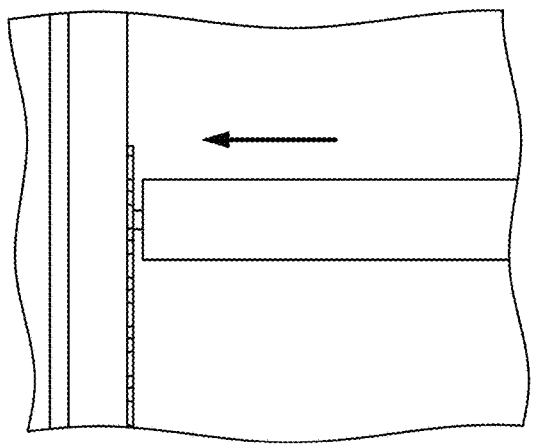

FIGS. 33A-B illustrate diagrams of different views of the two-stage tacker gun with an exposed tack. Unlike the fixation device illustrated in FIGS. 32A-B, the disclosed two-stage penetrating tacker gun uses an exposed tack 3102 as illustrated in FIGS. 33A-B. Since the tack 3102 is exposed (as seen in FIGS. 32A-B), the tack can make contact with the mesh first and therefore begin penetrating through the mesh and through the fascia. In some embodiments, exposing the tack can allow for a two-staged penetration process. The first stage of the two-staged penetration process can include manually pushing the tack though using the tacker gun and the second stage of the two-staged process can include pulling the trigger(s) to "kick" the tack in further, thereby fully penetrating the exposed tack in the fascia.

Figure 34A:
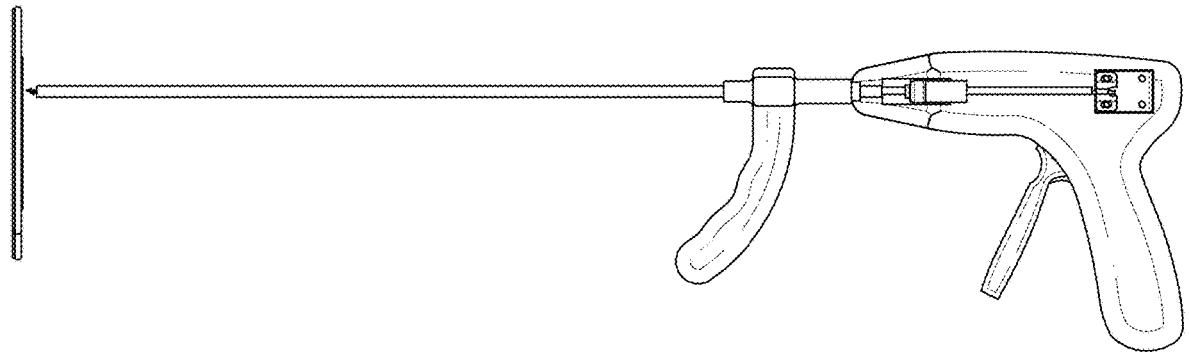
FIGS. 34A-C illustrate diagrams of a two-stage penetration process by which the two-stage tacker gun with an exposed tack can deploy a tack to penetrate the fascia in accordance with an exemplary embodiment of the disclosed subject matter.
Figure 34B:
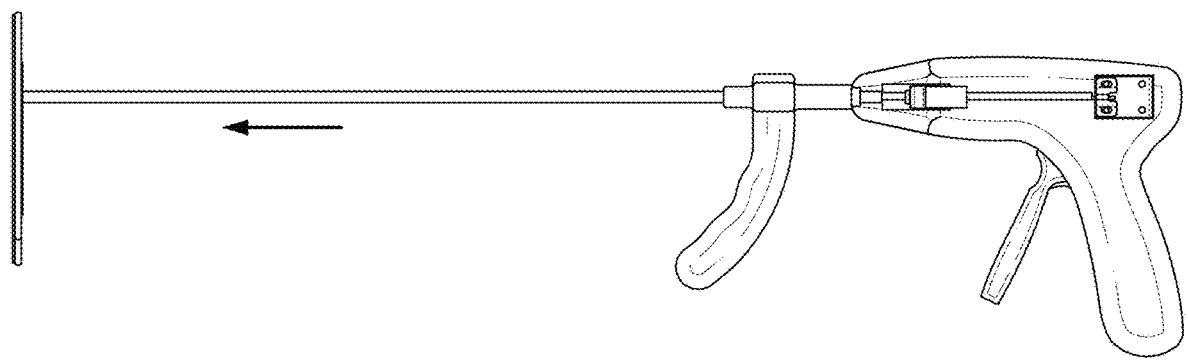
Figure 34C:
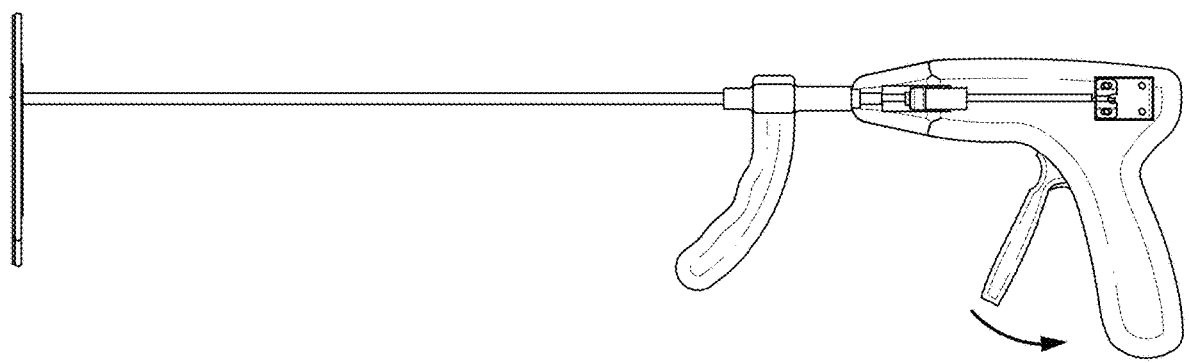

FIGS. 34A-C illustrate diagrams of a two-stage penetration process by which the two-stage tacker gun with an exposed tack can deploy a tack to penetrate the fascia. As shown in FIG. 34A, the tacker gun can be positioned in a desired location with respect to the fascia and/or the mesh. FIG. 34B illustrates the first stage (e.g., the manual penetration stage) of the two-staged penetration process in which the tacker gun is manually pushed to initialize penetration of the exposed tack 3102 into the mesh and/or fascia. FIG. 34C illustrates the second stage (e.g., the spring-mediated penetration stage) of the two-staged penetration process in which the trigger(s) are pulled to fire the tack through the mesh and/or fascia and complete penetration.

Figure 35A:
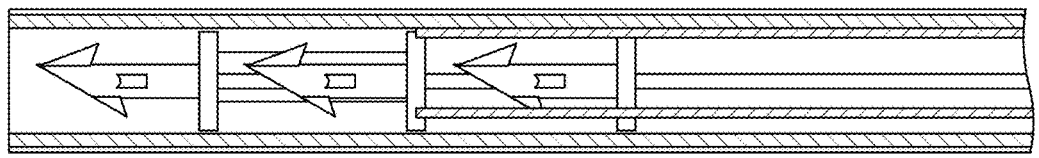
FIG. 35A illustrates a diagram of a cross section of the unexposed tack in the two stage penetration process in accordance with an exemplary embodiment of the disclosed subject matter.
Figure 35B:
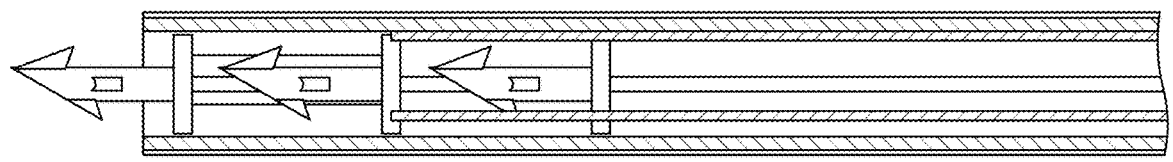
FIG. 35B illustrates a diagram of a cross section of the exposed tack in the two stage penetration process in accordance with an exemplary embodiment of the disclosed subject matter.

FIG. 35A illustrates a diagram of a cross section of the unexposed tack in the first stage of the two-stage penetration process. As illustrated in FIG. 35A, prior to the first stage, the tack is unexposed as it is resting within a barrel of the tacker gun. FIG. 35B illustrates a diagram of a cross section of the exposed tack in the two-stage penetration process. As illustrated in FIG. 35B, in the second stage, the tack is exposed as it is pushed out of the barrel of the tacker gun.

Figure 36A:
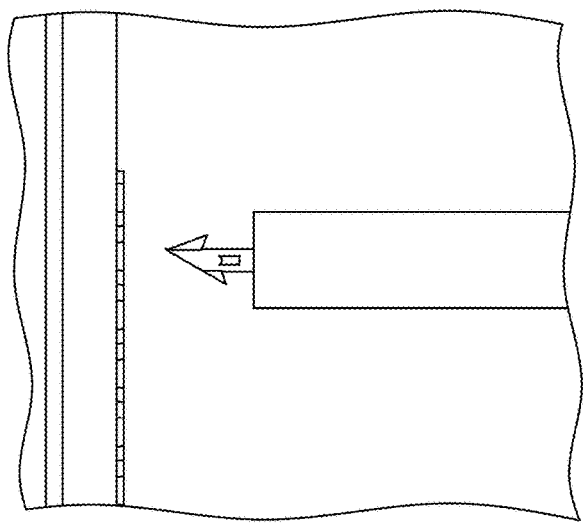
FIGS. 36A-D illustrate diagrams of a process by which the two-stage tacker gun with an exposed tack performs tack penetration in accordance with an exemplary embodiment of the disclosed subject matter.
Figure 36B:
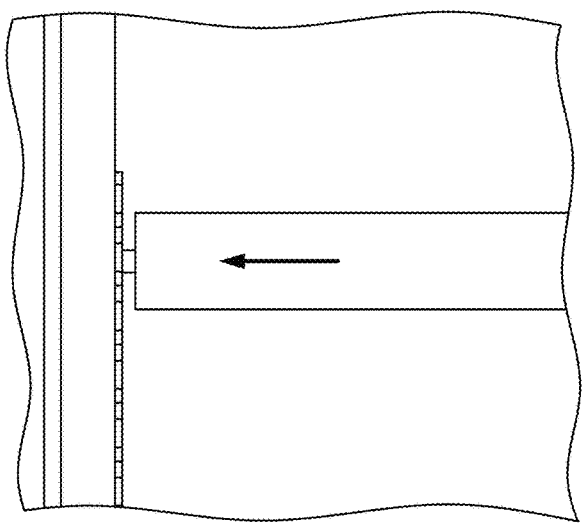
Figure 36C:
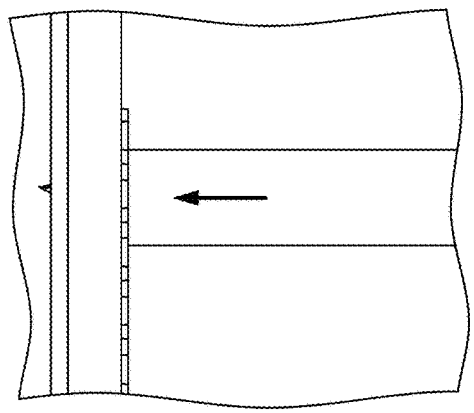
Figure 36D:
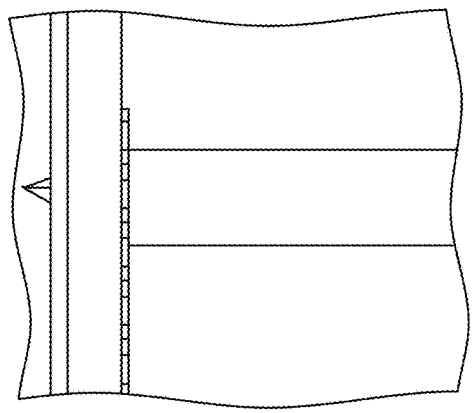

FIGS. 36A-D illustrate diagrams of a process by which the two-stage tacker gun with an exposed tack performs tack penetration. As illustrated in FIG. 36A, the tack can be positioned with respect to the fascia and/or mesh in the first (e.g., manual stage) stage of the two-stage penetration process. As illustrated in FIG. 36B, the tacker gun can be manually pushed to push the tack into the fascia and/or mesh. As illustrated in FIG. 36C, the tacker gun can be continued to be pushed up against the fascia and/or mesh with the exposed tack penetrating the fascia and/or mesh in the second stage (e.g., spring-mediation penetration stage) of the two-stage penetration process. As illustrated in FIG. 36D, the trigger(s) of the tacker gun can be pulled to complete tack penetration.

Figure 37A:
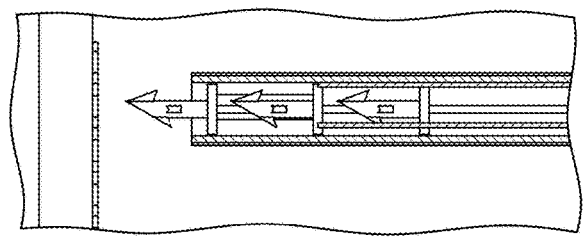
FIGS. 37A-D illustrate cross-sectional diagrams of a process by which the two-stage tacker gun with an exposed tack performs tack penetration shown in FIGS. 36A-D in accordance with an exemplary embodiment of the disclosed subject matter.
Figure 37B:
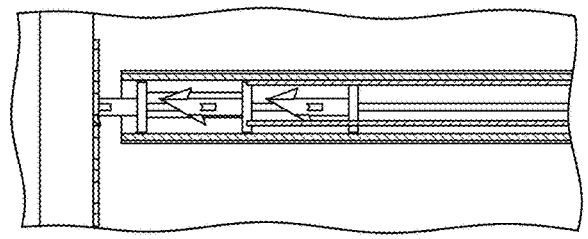
Figure 37C:
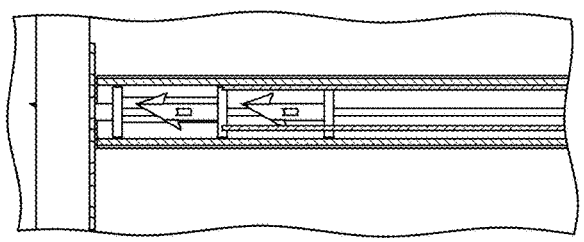
Figure 37D:
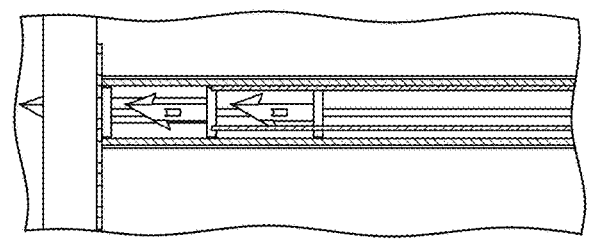

FIGS. 37A-D illustrate cross-sectional diagrams of the process by which the two-stage tacker gun with an exposed tack performs tack penetration shown in FIGS. 36A-D. For example, FIG. 37A illustrates the cross-sectional view of the tacker gun barrel of FIG. 36A, FIG. 37B illustrates the cross-sectional view of the tacker gun barrel of FIG. 36B, FIG. 37C illustrates the cross-sectional view of the tacker gun barrel of FIG. 36C, and FIG. 37D illustrates the cross-sectional view of the tacker gun barrel of FIG. 36D.

The affixation devices and methods of the disclosed subject matter have demonstrated desirable performance characteristics not achieved by conventional affixation devices and methods. For example, the devices and methods of affixing reinforcing material in accordance with the disclosed subject matter can allow surgeons to apply the necessary force to achieve tissue penetration during mesh onlay procedures while minimizing risk to the bowel. By engaging arms on opposing sides of a fascial incision, the fascia can be placed in tension as a surgeon applies downward force to affix reinforcing material. The ability to engage fascia on opposing sides of the fascial incision can allow for greater application of force. Additionally, the ability to control the spatial orientation of the affixation device arms can provide surgeons with greater flexibility to access surgical sites and spatially control and tension reinforcing materials during mesh onlay procedures.

Figure 38:
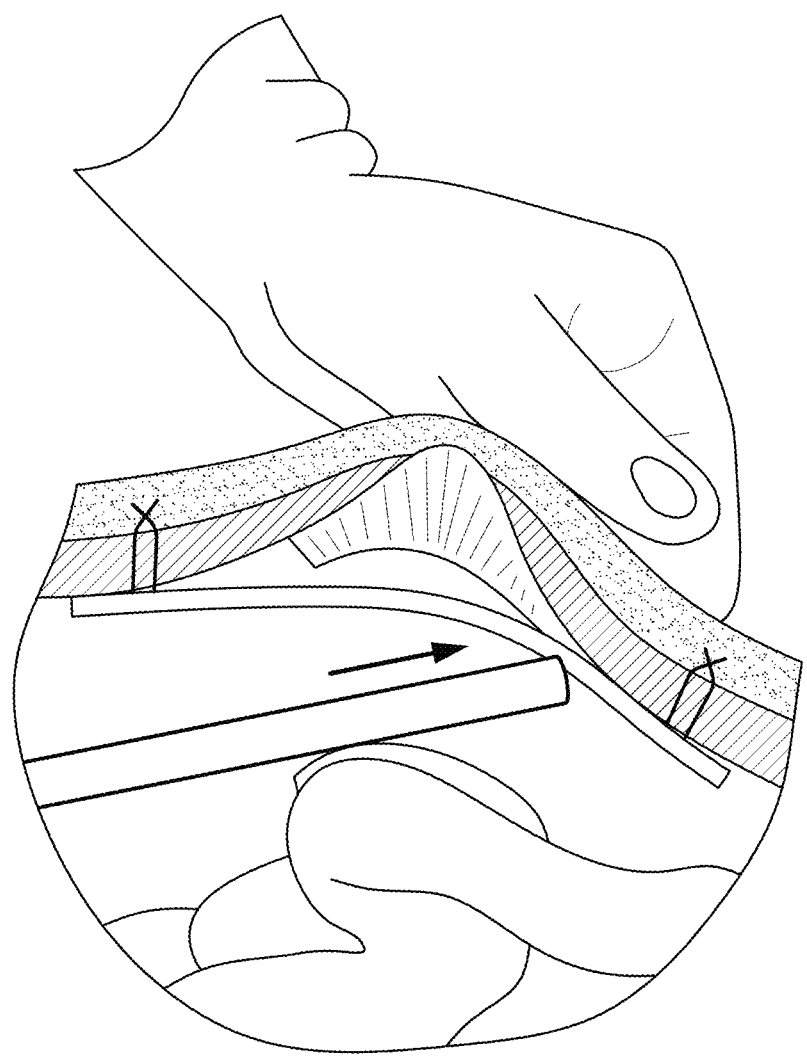
FIG. 38 illustrates a traditional laparoscopic mesh placement procedure.
Figure 39:
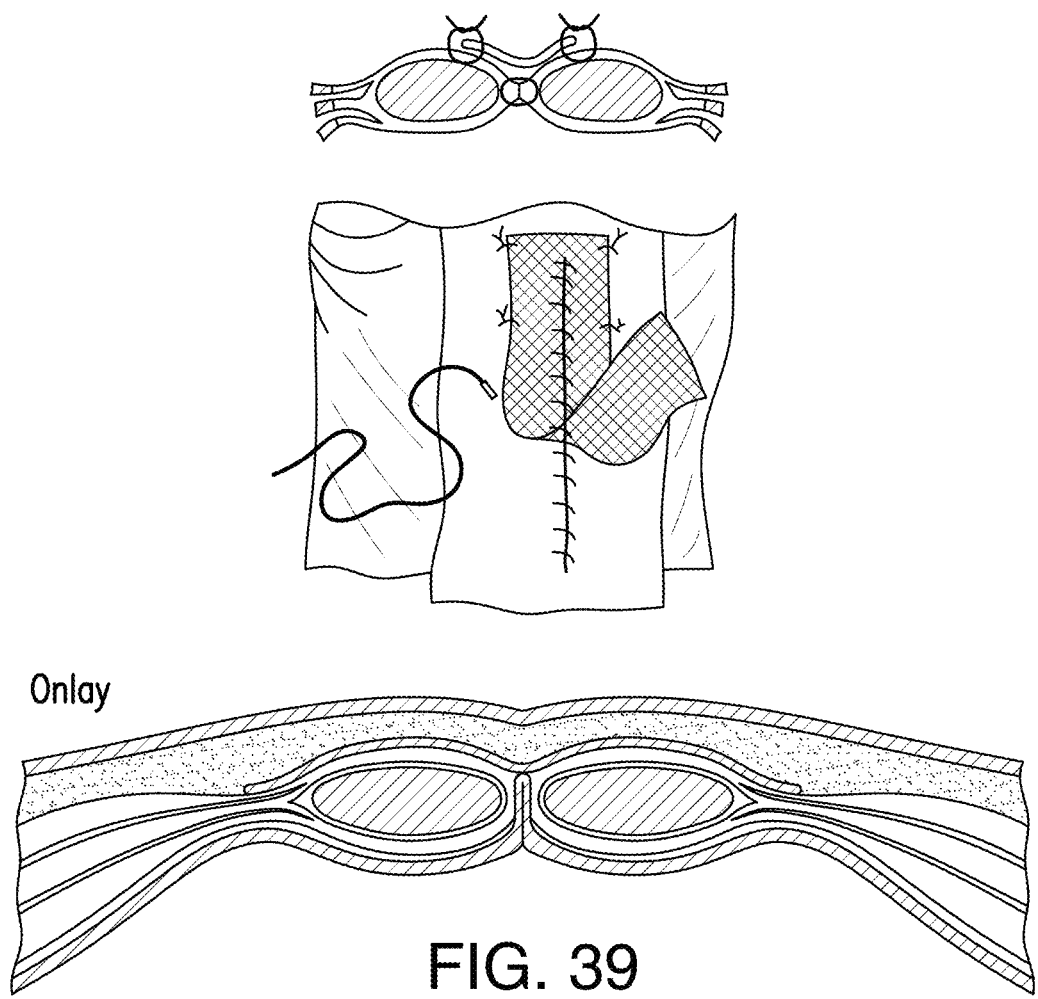
FIG. 39 illustrates exemplary reinforcement material placement during a mesh onlay procedure.

Additional force can be required to securely affix mesh during mesh onlay procedures as compared to laparoscopic procedures. During laparoscopic procedures for abdominal incision reinforcement, the reinforcing material is tacked upwards (away from the body), as depicted in FIG. 38, allowing the surgeon to apply a counteracting force to the fascia during mesh affixation. By contrast, and with reference to FIG. 39, during mesh onlay procedures the mesh is tacked onto the abdominal wall (inwards towards the body). As such, the surgeon cannot counteract the force required to affix reinforcing material to the fascia. Traditional devices for affixing reinforcing material during mesh onlay affixation procedures, such as single arm devices, can cause the fascia to buckle inwards towards the interior of the body and the bowel, which creates risk of injury to the bowels and other interior organs.

Although the embodiments herein are described primarily with reference to the affixation of mesh constructs, one of skill in the art will appreciate that the disclosed subject matter can also include affixation of other reinforcing materials, such as tissue, in a similar manner. One of skill in the art will recognize that the devices and methods of the disclosed subject matter can be used with permanent synthetic absorbable or non-absorbable reinforcing materials, biologic materials, or bio-absorbable materials or a hybrid material formed from components of each. Other applications intended to fall within the scope of the disclosed subject matter include, for purpose of illustration and not limitation, reinforcement and re-contouring of the fascia after rectus fascia plication for abdominoplasty (using mesh), and tendon or joint repair, where tendon can be controlled and affixed with an applicator so as to re-affix or reconstruct the tendon or joint capsule.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A method for onlay fixation of reinforcing material to a fascial incision in an abdominal wall to reinforce and augment closures thereof, comprising:

positioning a reinforcing material over the fascial incision;

engaging the reinforcing material with an applicator having first and second arms, each arm including a proximal end proximate a handle and a distal end, the first arm distal end and the second arm distal end each including a releasable coupling configured to engage the reinforcing material, wherein the distal end of the first arm is spaced from the distal end of the second arm such that the applicator engages with the reinforcing material on opposing sides of the fascial incision; and affixing the reinforcing material to an anterior of abdominal wall fascia with tacks by applying force to the tacks with the distal ends of the first and second arms in a direction extending away from the housing such that the tacks penetrate the fascia on opposing sides of the fascial incision.

2. The method of claim 1, further comprising applying a lateral tension to the reinforcing material by increasing a distance between opposing sides of the reinforcing material from a first distance to a second distance.

3. The method of claim 2, wherein the lateral tension is applied by increasing a distance between the distal end of the first arm and the distal end of the second arm from a first distance to a second distance after engaging the reinforcing material with the applicator.

4. The method of claim 3, wherein the applicator includes a spreading mechanism that controls the distance between the distal end of the first arm and the distal end of the second arm.

5. The method of claim 2, wherein the tacks are curvilinear in shape and the distance between opposing sides of the reinforcing material is increased as the curvilinear tacks penetrate the fascia.

6. The method of claim 2, wherein applying a lateral tension further comprises adjusting the tension to a desired tension using a tensiometer.

7. The method of claim 1, wherein affixing the reinforcing material includes using a firing mechanism to apply an impact load to the tacks such that the tacks penetrate the fascia.

8. The method of claim 1, wherein two or more tacks penetrate the fascia simultaneously.

9. The method of claim 1, further comprising controlling a distance between the first and second arms such that the tacks can be affixed at varying distances from one another.

10. The method of claim 1, wherein tacks are housed within the first arm and the second arm, and affixing the reinforcing material includes releasing tacks from the first arm and the second arm.

11. The method of claim 10, wherein tacks are stored in a stacked manner such that a second tack is automatically ready to penetrate the fascia after a first tack is released from either the first arm or second arm during affixation.

12. The method of claim 1, wherein affixing the reinforcing material includes penetrating the fascia with tacks on opposing sides of the fascial incision at a first location and a second location disposed at a predetermined distance along the fascial incision from the first location.

13. The method of claim 1, wherein the reinforcing material comprises mesh.

14. The method of claim 1, wherein the reinforcing material is mechanically anchored over a primary repair of the fascial incision such that the reinforcing material decreases a tension across the primary repair.

15. The method of claim 14, wherein the primary repair comprises sutures.

16. The method of claim 1, wherein the reinforcing material is affixed to the facial incision after incisional access to the abdomen during an index abdominal surgical procedure.

17. The method of claim 3, wherein the releasable couplings apply at least 1 lbf of lateral tension to the reinforcing material.

* * * * *